US012594122B2

(12) United States Patent
Piron et al.

(10) Patent No.: US 12,594,122 B2
(45) Date of Patent: *Apr. 7, 2026

(54) CONTEXT AWARE SURGICAL SYSTEMS AND METHODS VIA HYPERSPECTRAL IMAGE ANALYSIS TO CONFIGURE A DEVICE DURING MEDICAL PROCEDURE

(71) Applicant: SYNAPTIVE MEDICAL INC., Toronto (CA)

(72) Inventors: Cameron Piron, Toronto (CA); Michael Wood, Toronto (CA); Gal Sela, Toronto (CA); Joshua Richmond, Toronto (CA); Murugathas Yuwaraj, Markham (CA); Stephen McFadyen, Toronto (CA); Alex Panther, Toronto (CA); Nishanthan Shanmugaratnam, Scarborough (CA); William Lau, Toronto (CA); Monroe M. Thomas, Toronto (CA); Wes Hodges, London (CA); Simon Alexander, Toronto (CA); David Gallop, Toronto (CA)

(73) Assignee: Synaptive Medical Inc.

( * ) Notice: Subject to any disclaimer, the term of this patent is extended or adjusted under 35 U.S.C. 154(b) by 940 days.

This patent is subject to a terminal disclaimer.

(21) Appl. No.: 17/649,561

(22) Filed: Feb. 1, 2022

(65) Prior Publication Data

US 2022/0151702 A1     May 19, 2022

Related U.S. Application Data

(63) Continuation of application No. 15/644,134, filed on Jul. 7, 2017, now Pat. No. 11,272,984, which is a
(Continued)

(51) Int. Cl.
A61B 34/10 (2016.01)
A61B 1/00 (2006.01)
(Continued)

(52) U.S. Cl.
CPC .......... A61B 34/10 (2016.02); A61B 1/00059 (2013.01); A61B 1/00149 (2013.01);
(Continued)

(58) Field of Classification Search
CPC . A61B 34/10; A61B 1/00059; A61B 1/00149; A61B 1/045; A61B 6/5247;
(Continued)

(56) References Cited

PUBLICATIONS

Piron, Cameron et al., "Context Aware Surgical Systems and Methods via Hyperspectral Image Analysis to Configure a Device During Medical Procedure," U.S. Appl. No. 15/644,134, filed Jul. 7, 2017, Notice of Allowance issued.
(Continued)

*Primary Examiner* — Serkan Akar

(57) ABSTRACT

Systems and methods involving a control and processing system interfaceable with a device, a tracking system, and a data storage device, the control and processing system having a processor configured by a set of instructions storable in relation to a nontransient memory device to: identify the at least one device, via the tracking system operating with at least one of an electromagnetic system and a radiofrequency (RF) system, during a medical procedure; obtain an image of a region of interest associated with the medical procedure; process the image to identify a context measure associated with a current state of the medical procedure; obtain a parameter for adaptively configuring the device during the medical procedure, the parameter customizable based on the context measure, the parameter providable for the device according to a prioritized list, and the device reverting to a default configuration when another device is removed from the region of interest; and configure the device according to the parameter.

10 Claims, 40 Drawing Sheets

Related U.S. Application Data continuation of application No. 14/771,643, filed as application No. PCT/CA2014/050265 on Mar. 14, 2014, now Pat. No. 9,788,906.

(60) Provisional application No. 61/924,993, filed on Jan. 8, 2014, provisional application No. 61/818,255, filed on May 1, 2013, provisional application No. 61/818,280, filed on May 1, 2013, provisional application No. 61/818,223, filed on May 1, 2013, provisional application No. 61/818,325, filed on May 1, 2013, provisional application No. 61/801,282, filed on Mar. 15, 2013, provisional application No. 61/801,530, filed on Mar. 15, 2013, provisional application No. 61/801,746, filed on Mar. 15, 2013, provisional application No. 61/800,911, filed on Mar. 15, 2013, provisional application No. 61/800,787, filed on Mar. 15, 2013, provisional application No. 61/801,143, filed on Mar. 15, 2013, provisional application No. 61/800,695, filed on Mar. 15, 2013, provisional application No. 61/800,155, filed on Mar. 15, 2013.

(51) Int. Cl.

| | |
|---|---|
| A61B 1/045 | (2006.01) |
| A61B 6/00 | (2024.01) |
| A61B 6/03 | (2006.01) |
| A61B 8/08 | (2006.01) |
| A61B 8/13 | (2006.01) |
| A61B 18/14 | (2006.01) |
| A61B 34/00 | (2016.01) |
| A61B 34/20 | (2016.01) |
| A61B 90/00 | (2016.01) |
| A61B 90/30 | (2016.01) |
| A61B 90/90 | (2016.01) |
| A61B 90/94 | (2016.01) |
| A61B 90/96 | (2016.01) |
| A61B 90/98 | (2016.01) |
| G06T 7/00 | (2017.01) |
| G06T 7/70 | (2017.01) |
| G06T 11/00 | (2006.01) |
| A61B 34/30 | (2016.01) |
| A61B 90/50 | (2016.01) |

(52) U.S. Cl.
CPC ............ *A61B 1/045* (2013.01); *A61B 6/5247* (2013.01); *A61B 34/20* (2016.02); *A61B 90/30* (2016.02); *A61B 90/90* (2016.02); *A61B 90/94* (2016.02); *A61B 90/96* (2016.02); *A61B 90/98* (2016.02); *G06T 7/0012* (2013.01); *G06T 7/70* (2017.01); *G06T 11/003* (2013.01); *A61B 6/03* (2013.01); *A61B 8/0808* (2013.01); *A61B 8/0841* (2013.01); *A61B 8/13* (2013.01); *A61B 18/14* (2013.01); *A61B 2034/2055* (2016.02); *A61B 2034/2065* (2016.02); *A61B 2034/252* (2016.02); *A61B 2034/256* (2016.02); *A61B 34/30* (2016.02); *A61B 2090/306* (2016.02); *A61B 2090/3618* (2016.02); *A61B 2090/373* (2016.02); *A61B 2090/3735* (2016.02); *A61B 2090/374* (2016.02); *A61B 2090/3762* (2016.02); *A61B 2090/378* (2016.02); *A61B 2090/3983* (2016.02); *A61B 90/50* (2016.02); *G06T 2207/10081* (2013.01); *G06T 2207/10088* (2013.01); *G06T 2207/10104* (2013.01); *G06T 2207/10132* (2013.01); *G06T 2207/30016* (2013.01)

(58) Field of Classification Search
CPC ......... A61B 34/20; A61B 90/30; A61B 90/90; A61B 90/94; A61B 90/96; A61B 90/98; A61B 6/03; A61B 8/0808; A61B 8/0841; A61B 8/13; A61B 18/14; A61B 34/30; A61B 90/50; A61B 2034/2055; A61B 2034/2065; A61B 2034/252; A61B 2034/256; A61B 2090/306; A61B 2090/3618; A61B 2090/373; A61B 2090/3735; A61B 2090/374; A61B 2090/3762; A61B 2090/378; A61B 2090/3983; G06T 7/0012; G06T 7/70; G06T 11/003; G06T 2207/10081; G06T 2207/10088; G06T 2207/10104; G06T 2207/10132; G06T 2207/30016

See application file for complete search history.

(56) References Cited

PUBLICATIONS

Piron, Cameron et al., "Context Aware Surgical Systems for Intraoperatively Configuring Imaging Devices", U.S. Appl. No. 14/771,643, filed Aug. 31, 2015, now U.S. Pat. No. 9,788,906, issued Oct. 10, 2017.

GROSS RESECTION
TOOL IDENTIFIED IN
SURGICAL FIELD

FINE RESECTION
TOOL IDENTIFIED IN
SURGICAL FIELD

| Identified Medical Instrument | Camera Configuration Parameters |
|---|---|
| Suction Device | Reduce shutter speed, reduce gain, and reduce sensitivity; rationale: significant fluid is likely in the surgical field producing surface glare that will saturate the camera |
| Resection Device | Increase gain and sensitivity; rationale: as resection is being performed the optical system will be at a high zoom factor reducing the light reaching the camera, and increase in camera gain and sensitivity will improve image contrast |
| Electrocautery Device | Color saturation to emphasize red wavelengths; rationale: instrument likely being used for cauterization of bleeding vessels, thus significant blood is likely in the surgical field, emphasizing red wavelengths will improve image contrast |
| Suction and Resection Devices | Maintain shutter speed, gain, and sensitivity; rationale: while significant fluid is likely in the surgical field producing surface glare, the system will likely be at high zoom and require the additional image gain and sensitivity |
| Suction and Electrocautery Devices | Color saturation to emphasize red wavelengths; rationale: tools likely being used for cauterization of bleeding vessels, thus significant blood is likely in the surgical field, emphasizing red wavelengths will improve image contrast |
| Resection and Electrocautery Devices | Color saturation to emphasize red wavelengths; rationale: tools likely being used for cauterization of bleeding micro-vessels, thus significant blood is likely in the surgical field, emphasizing red wavelengths will improve image contrast |

FIG. 5C

| Identified Medical Instrument | Imaging Optics Assembly Configuration Parameters |
|---|---|
| Suction Device | Cross imaging optics polarization with illumination optics polarization; rationale: significant fluid is likely in the surgical field producing surface glare that will obscure surgical field, crossed polarizers will eliminate this glare |
| Resection Device | Increase zoom; rationale: as microresection is being performed the optical system should be at a higher zoom to better visualize the resection |
| Electrocautory Device | Cross imaging optics polarization with illumination optics polarization; rationale: significant fluid (blood) is likely in the surgical field producing surface glare that will obscure surgical field including the bleeding vessels, crossed polarizers will eliminate this glare |
| Suction and Resection Devices | Cross imaging optics polarization with illumination optics polarization and increase zoom; rationale: significant fluid is likely in the surgical field producing surface glare that will obscure surgical field, crossed polarizers will eliminate this glare, and an increase in zoom will aid in visualization of microresection |
| Suction and Electrocautory Devices | Cross imaging optics polarization with illumination optics polarization; rationale: significant fluid (blood) is likely in the surgical field producing surface glare that will obscure surgical field including the bleeding vessels, crossed polarizers will eliminate this glare |
| Resection and Electrocautory Devices | Cross imaging optics polarization with illumination optics polarization and increase zoom; rationale: significant fluid is likely in the surgical field producing surface glare that will obscure surgical field, crossed polarizers will eliminate this glare, and an increase in zoom will aid in visualization of microresection |

FIG. 5D

| Identified Medical Instrument | Illuminator Configuration Parameters |
|---|---|
| Suction Device | Set illumination angle to be non-perpendicular with imaging plane; rationale: significant fluid is likely in the surgical field producing surface glare that will obscure surgical field, the illumination being non-perpendicular with imaging plane will eliminate the majority of this glare |
| Resection Device | Increase intensity; rationale: as microresection is being performed the optical system should be at a higher zoom to better visualize the resection, increasing the intensity accordingly increase the light reaching the camera and improve contrast and resolution |
| Electrocautory Device | Set illumination angle to be non-perpendicular with imaging plane and increase intensity of red wavelengths; rationale: significant fluid is likely in the surgical field producing surface glare that will obscure surgical field, the illumination being non-perpendicular with imaging plane will eliminate the majority of this glare, increasing the red wavelengths will increase overall light levels as these wavelengths are not absorbed by blood |
| Suction and Resection Devices | Set illumination angle to be non-perpendicular with imaging plane and increase light intensity; rationale: significant fluid is likely in the surgical field producing surface glare that will obscure surgical field, the illumination being non-perpendicular with imaging plane will eliminate the majority of this glare, as microresection is being performed the optical system should be at a higher zoom to better visualize the resection, increasing the intensity will increase the light reaching the camera and improve contrast and resolution |
| Suction and Electrocautory Devices | Set illumination angle to be non-perpendicular with imaging plane and increase intensity of red wavelengths; rationale: significant fluid is likely in the surgical field producing surface glare that will obscure surgical field, the illumination being non-perpendicular with imaging plane will eliminate the majority of this glare, increasing the red wavelengths will increase overall light levels as these wavelengths are not absorbed by blood |
| Resection and Electrocautory Devices | Set illumination angle to be non-perpendicular with imaging plane, increase light intensity, and increase intensity of red wavelengths; rationale: significant fluid is likely in the surgical field producing surface glare that will obscure surgical field, the illumination being non-perpendicular with imaging plane will eliminate the majority of this glare, as microresection is being performed the optical system should be at a higher zoom to better visualize the resection, increasing the intensity will increase the light reaching the camera and improve contrast and resolution, increasing the red wavelengths will increase overall light levels as these wavelengths are not absorbed by blood |

FIG. 5E

| Identified Medical Instrument | Illuminator Focusing Optics Configuration Parameters |
|---|---|
| Suction Device | Cross illumination polarization with imaging optics polarizer; rationale: significant fluid is likely in the surgical field producing surface glare that will obscure surgical field, crossed polarizers will eliminate this glare |
| Resection Device | Decrease spot illumination spot size; rationale: as resection is being performed the optical system will be at a high zoom factor reducing the light reaching the camera, reducing the spot size will increase the light reaching the camera |
| Electrocautory Device | Cross illumination polarization with imaging optics polarizer; rationale: significant fluid (blood) is likely in the surgical field producing surface glare that will obscure surgical field, crossed polarizers will eliminate this glare |
| Suction and Resection Devices | Cross illumination polarization with imaging optics polarizer and decrease illumination spot size; rationale: significant fluid (blood) is likely in the surgical field producing surface glare that will obscure surgical field, crossed polarizers will eliminate this glare, as microresection is being performed the optical system will be at a high zoom factor reducing the light reaching the camera, reducing the spot size will increase the light reaching the camera |
| Suction and Electrocautory Devices | Cross illumination polarization with imaging optics polarizer; rationale: significant fluid (blood) is likely in the surgical field producing surface glare that will obscure surgical field, crossed polarizers will eliminate this glare |
| Resection and Electrocautory Devices | Cross illumination polarization with imaging optics polarizer and decrease illumination spot size; rationale: significant fluid (blood) is likely in the surgical field producing surface glare that will obscure surgical field, crossed polarizers will eliminate this glare, as microresection is being performed the optical system will be at a high zoom factor reducing the light reaching the camera, reducing the spot size will increase the light reaching the camera |

FIG. 5F

| Identified Medical Instrument | Camera Configuration Parameters |
|---|---|
| Instrument 1 | Configuration parameter set 1 |
| Instrument 2 | Configuration parameter set 2 |
| Instrument 3 | Configuration parameter set 3 |
| Instrument 4 | Configuration parameter set 4 |
| Instrument 5 | Configuration parameter set 5 |
| Instrument 6 | Configuration parameter set 6 |

FIG. 5G

| Identified Medical Instrument | Camera Configuration Parameters |
|---|---|
| Suction Device | Reduce shutter speed, reduce gain, and reduce sensitivity; rationale: significant fluid is likely in the surgical field producing surface glare that will saturate the camera |
| Resection Device | Increase gain and sensitivity; rationale: as microresection is being performed the optical system will be at a high zoom factor reducing the light reaching the camera, and increase in camera gain and sensitivity will improve image contrast |
| Electrocautery Device | Color saturation to emphasize red wavelengths; rationale: instrument likely being used for cauterization of bleeding vessels, thus significant blood is likely in the surgical field, emphasizing red wavelengths will improve image contrast |
| Suction and Resection Devices | Maintain shutter speed, gain, and sensitivity; rationale: while significant fluid is likely in the surgical field producing surface glare, the system will likely be at high zoom and require the additional image gain and sensitivity |
| Suction and Electrocautery Devices | Color saturation to emphasize red wavelengths; rationale: tools likely being used for cauterization of bleeding vessels, thus significant blood is likely in the surgical field, emphasizing red wavelengths will improve image contrast |
| Resection and Electrocautery Devices | Color saturation to emphasize red wavelengths; rationale: tools likely being used for cauterization of bleeding micro-vessels, thus significant blood is likely in the surgical field, emphasizing red wavelengths will improve image contrast |
| No instrument identified | Increase gain and sensitivity; rationale: the most likely procedure being performed and the one where the camera configuration is most important is when the surgeon is performing resection and needs Ideal tissue contrast for differentiation. Therefore as resection is being performed the optical system will be at a high zoom factor reducing the light reaching the camera, and increase in camera gain and sensitivity will improve image contrast |

FIG. 5H

| Procedure Name | Identified Medical Instrument | Camera Configuration Parameters |
|---|---|---|
| Port Based Tumor Resection | Suction Device | Reduce shutter speed, reduce gain, and reduce sensitivity; rationale: significant fluid is likely in the surgical field producing surface glare that will saturate the camera |
| Port Based Tumor Resection | Resection Device | Increase gain and sensitivity; rationale: as resection is being performed the optical system will be at a high zoom factor reducing the light reaching the camera, and increase in camera gain and sensitivity will improve image contrast |
| Port Based Tumor Resection | Electrocautory Device | Color saturation to emphasize red wavelengths; rationale: instrument likely being used for cauterization of bleeding vessels, thus significant blood is likely in the surgical field, emphasizing red wavelengths will improve image contrast |
| Port Based Tumor Resection | Suction and Resection Devices | Maintain shutter speed, gain, and sensitivity; rationale: while significant fluid is likely in the surgical field producing surface glare, the system will likely be at high zoom and require the additional image gain and sensitivity |
| Port Based Tumor Resection | Suction and Electrocautory Devices | Color saturation to emphasize red wavelengths; rationale: tools likely being used for cauterization of bleeding vessels, thus significant blood is likely in the surgical field, emphasizing red wavelengths will improve image contrast |
| Port Based Tumor Resection | Resection and Electrocautory Devices | Color saturation to emphasize red wavelengths; rationale: tools likely being used for cauterization of bleeding micro-vessels, thus significant blood is likely in the surgical field, emphasizing red wavelengths will improve image contrast |
| Port Based Clot Removal | Port | Camera will zoom to maximize view of distal end of the port Rationale: to assist the surgeon in locating the clot once in the surgical area of interest within the brain |
| Port Based Clot Removal | Suction device | Color saturation to emphasize red wavelengths; rationale: For clot removal surgery (caused by a Intracranial hemorrhage) the suction device is used to remove excess blood from the surgical site of interest. Therefore when the suction device is used in port based clot removal surgery the system knows the site will be occluded by a lot of blood. To improve visibility the colour saturation configuration of the camera is adjusted to emphasize red wavelengths |
| Lumbar Microscopic Discectomy and Decompression | Retractor | Increase gain and sensitivity; rationale: as the nerve is being retracted the optical system will be at a high zoom factor reducing the light reaching the camera, and increase in camera gain and sensitivity will improve image contrast allowing the surgeon to more easily differentiate the nerve tissue from other tissue within the surgical area of interest at the distal end of the port |
| Lumbar Microscopic Discectomy and Decompression | Pituitary Forceps and Retractor | Color saturation to emphasize spinal bone; rationale: in this stage of the surgery the fragmented bone is being removed from the surgical site of interest, with optimal contrast for viewing bone the surgeon will be able to more effectively remove all of the fragmented bone without leaving smaller less visible pieces behind. |
| Lumbar Microscopic Discectomy and Decompression | Irrigation Cannula | Reduce shutter speed, reduce gain, and reduce sensitivity; rationale: During this step in the procedure pressurized liquid is used to dislodge any remaining herniated disc fragments from the area. As such significant fluid is likely in the surgical field producing surface glare that will saturate the camera |

FIG. 5I

| Identified Medical Instrument | Procedure Phase | System Configuration Parameters |
|---|---|---|
| Pointer Tool | Craniotomy (2100) | Follow pointer tool for confirmation of drilling boundaries |
| Scalpel | Craniotomy (2100) | UI overlays cuts to be made on skull of patient based on registration of 3D rendered MRI scan of patients brain and patients brain |
| Neurosurgical Drill | Craniotomy (2100) | UI reconfigures and provides information on how deep the drill is into the skull |
| Ultrasound Imaging device | Cannulation (2110) | UI reconfigures to show Ultrasound view |
| Introducer and Port | Cannulation (2110) | Robotic arm is reconfigured to move imaging device approximately orthogonal to cannulation location to show graduation marks on introducer as its inserted into the brain |
| Resection Tool | Gross Resection (2120) | The system configures the imaging device to simultaneously capture visible light and scans for fluorescence imaging as well as glare |
| Resection Tool and Surgical Forceps | Gross Resection (2120) | The system configures the imaging device to simultaneously capture visible light and scans for fluorescence imaging as well as glare |
| Electrocautory Device | Bleeding Management (2130) | The system configures the imaging device to begin NIR imaging to provide more light penetration through the blood and consequently more ability to see through to the occluded surgical area of interest |
| Resection Tool and Pointer Tool Mounted with Raman Probe | Fine Resection (2140) | The system configures the imaging device to begin Polarization Sensitive Imaging to provide better information of structural surfaces at the surgical site of interest. To prevent the surgeon from accidentally damaging vital neural tracts |

FIG. 5J

| Identified Medical Instrument | Robotic Arm Configuration Parameters |
|---|---|
| Neurosurgical Drill | The robotic arm will align the camera to view the drilling area, at the maximum distance it can safely reach from the drilling area. (in a typical surgery this may be 40-60cm) <br> rationale: during the craniotomy when the drilling of the skull is performed the surgeon normally does not utilize the scope for viewing while the drilling is being done, and hence removal of the scope from around the surgical space will result in less occlusion of the surgeons view. |
| Introducer (Obturator) | The robotic arm will align the external scope to provide a orthogonal view as the introducer is cannulated <br> rationale: this orthogonal view provides the external scope the ability to view the graduation marks on the side of the introducer as it is cannulated into the brain, providing the depth that the introducer is inserted before |
| Port | The robotic arm will align the external scope to provide a coaxial view of the surgical area of interest at the distal end of the port <br> rationale: so that the surgeon has an enhanced view of the surgical area of interest where the surgery is being performed |
| Introducer (Obturator) and Port | The robotic arm will align the external scope to provide a orthogonal view as the introducer is cannulated <br> rationale: this orthogonal view provides the external scope the ability to view the graduation marks on the side of the introducer as it is cannulated into the brain, providing the depth that the introducer is inserted before <br> note: when the port and introducer are both recognized the presence of the introducer implies the cannulation process is occurring. |
| Neurosurgical Drill | The robotic arm will align the camera to view the drilling area, at the maximum distance it can safely reach from the drilling area. (in a typical surgery this may be 40-60cm) <br> rationale: during the craniotomy when the drilling of the skull is performed the surgeon normally does not utilize the scope for viewing while the drilling is being done, and hence removal of the scope from around the surgical space will result in less occlusion of the surgeons view. |
| Introducer (Obturator) | The robotic arm will align the external scope to provide a orthogonal view as the introducer is cannulated <br> rationale: this orthogonal view provides the external scope the ability to view the graduation marks on the side of the introducer as it is cannulated into the brain, providing the depth that the introducer is inserted before |

FIG. 5K

| Identified Medical Instrument | User Interface Configuration Parameters |
|---|---|
| Suction Device | UI configures to display a control section which changes the suction force of the suction device |
| Port and Resection Device | UI configures to provide an option to turn on various imaging modes for tumor differentiation: these would be represented as buttons some examples being Raman probe, Hyperspectral imaging, Polarization Sensitive imaging, NIR imaging, OCT imaging, PSOCT imaging. rationale: when resecting a tumor it is important to avoid resecting healthy brain tissue as this can cause unnecessary loss of function for the patient |
| Introducer (obtruator) | UI configures to display any potential tracts the introducer may come into contact with during insertion into the brain, it would also provide a display of force felt by the distal tip and sides of the port as well as sound an alarm if this force exceeded a threshold. rationale: Determining the amount of force felt by the introducer during the penetration of the brain and its tissue, can be an important factor. This force sensor can help determine the density of the tumor when it is approached which can assist the surgeon by helping to adjust their trajectory in the case of a tumor role. In addition the force sensor can also help a surgeon to determine if too much damage would be caused if they were to penetrate at a particular point. |
| Port and Therapeutic device | UI configures to display information about the tumor that has been resected during that surgery, and also displays information on previously resected tumors of similar makeup and the effects of various solutions on them. The UI also configures to display and provide an option to choose any potential therapeutic solutions which could be potentially delivered by the therapeutic device to the remaining tumor tissue or any mixture of therapeutic solutions. rationale: Unique tumors may require unique solutions, therefore having information on tumors and their reaction to various types of therapeutic solutions and mixtures of those solutions can assist the surgeon in being more effective in providing therapy to the patient. |
| Pointer Device | UI configures to display a wide-field camera view of the surgical area of interest and the registered preoperative image of the patients anatomy of interest. rationale: before beginning surgery it is important to confirm correct registration of the preoperative images to assure the correct trajectory is taken to access the tumor. This is done by touching points on the patient and making sure they're correctly located on the preoperative image data. note: since there is no port detected it can be assumed that we are in a pre-surgical state and the reason is |
| Pointer device and port | UI configures to provide a view of the distal end of the port as acquired by the external scope and a cursor which follows the tip of the pointer tool when it occludes the view of the distal end of the port. The cursor is used when prompted by the surgeon to outline an area that needs to be zoomed up on or stored by the system. rationale: The pointer device when used in combination with the port can be used to identify surgical areas of interest to the system by the user. These areas of interest may require a greater zoom or a different type of imaging modality to satisfactorily complete the surgery. |

INTRAOPERATIVELY OBTAIN IMAGE(S) OF
REGION OF INTEREST                                                 500

PROCESS IMAGE(S) TO OBTAIN CONTEXT
MEASURE ASSOCIATED WITH CURRENT
STATE OF MEDICAL PROCEDURE                                         505

OBTAIN CONFIGURATION PARAMETER(S)
ASSOCIATED WITH CONTEXT MEASURE                                    510

CONFIGURE DEVICE BASED ON CONTEXT
PARAMETER(S)                                                       515

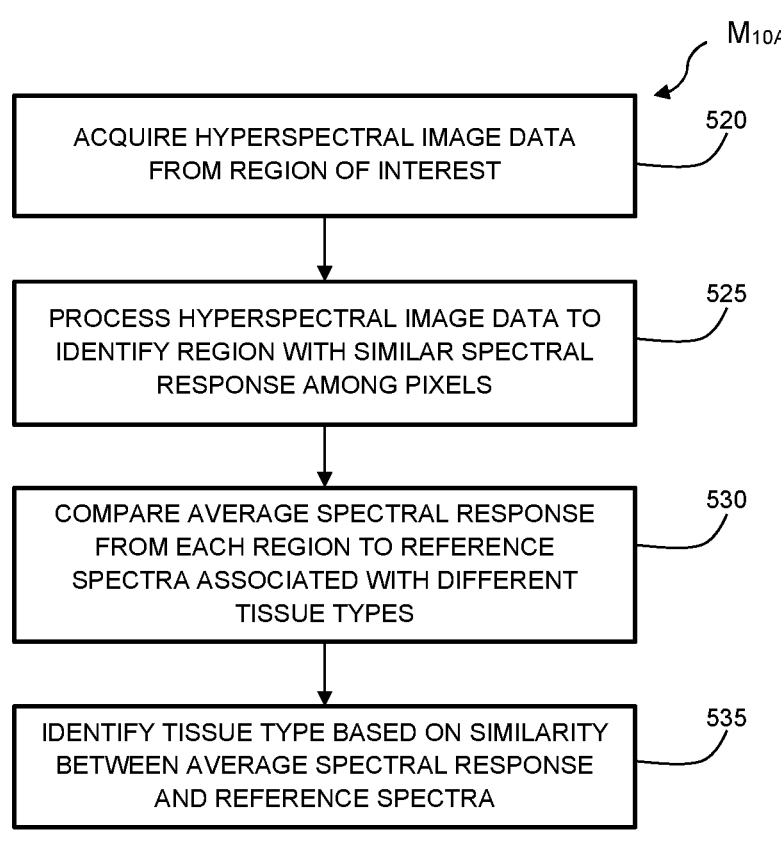

M₁₀ₐ

| | 520 |
|---|---|
| ACQUIRE HYPERSPECTRAL IMAGE DATA FROM REGION OF INTEREST | |

| | 525 |
|---|---|
| PROCESS HYPERSPECTRAL IMAGE DATA TO IDENTIFY REGION WITH SIMILAR SPECTRAL RESPONSE AMONG PIXELS | |

| | 530 |
|---|---|
| COMPARE AVERAGE SPECTRAL RESPONSE FROM EACH REGION TO REFERENCE SPECTRA ASSOCIATED WITH DIFFERENT TISSUE TYPES | |

| | 535 |
|---|---|
| IDENTIFY TISSUE TYPE BASED ON SIMILARITY BETWEEN AVERAGE SPECTRAL RESPONSE AND REFERENCE SPECTRA | |

FIG. 10A

| Tissue Type | Illuminator Configuration Parameters |
|---|---|
| Brain White Matter | To enhance light penetration: increase illumination power at visible wavelengths above 500 nm, to enhance surface contrast: decrease illumination power at visible wavelengths bellow 500 nm |
| Brain Grey Matter | To enhance light penetration: increase illumination power at visible wavelengths above 550 nm, to enhance surface contrast: decrease illumination power at visible wavelengths bellow 550 nm |
| Muscle | To enhance light penetration: increase illumination power at visible wavelengths above 600 nm, to enhance surface contrast: decrease illumination power at visible wavelengths bellow 600 nm |

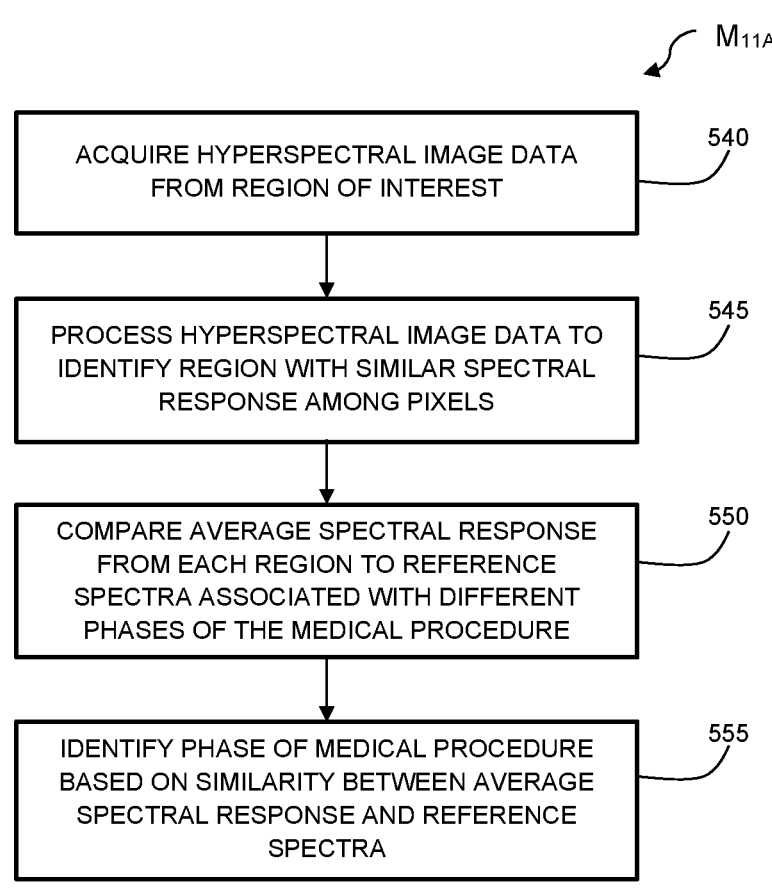

ACQUIRE HYPERSPECTRAL IMAGE DATA
FROM REGION OF INTEREST                    540

PROCESS HYPERSPECTRAL IMAGE DATA TO
IDENTIFY REGION WITH SIMILAR SPECTRAL
RESPONSE AMONG PIXELS                      545

COMPARE AVERAGE SPECTRAL RESPONSE
FROM EACH REGION TO REFERENCE
SPECTRA ASSOCIATED WITH DIFFERENT
PHASES OF THE MEDICAL PROCEDURE            550

IDENTIFY PHASE OF MEDICAL PROCEDURE
BASED ON SIMILARITY BETWEEN AVERAGE
SPECTRAL RESPONSE AND REFERENCE
SPECTRA                                    555

FIG. 11A

| Phase of Medical Procedure | Camera Configuration Parameters |
|---|---|
| Craniotomy | Zoomed Out |
| Cannulation | Oriented almost orthogonal to port with introducer, and zoomed in on the graduation marks as the port with introducer is inserted into brain through dura. |
| Gross Resection | Zoomed in on circumference of port opening. With the focus optimized for all of the tissue at the distal end of the port |
| Fine Resection | Zoomed in on tip of tool, down the port, on tissue being resected. In addition the focus of the camera will be on the tissue being resected and not the entire image. |

WHILE OBTAINING FIRST IMAGES WITH FIRST IMAGING MODALITY, INTERMITTENTLY OBTAIN SECOND IMAGE(S) WITH SECOND IMAGING MODALITY

610

PROCESS SECOND IMAGES AND CALCULATE IMAGE MEASURE ASSOCIATED WITH SECOND IMAGING MODALITY

615

DOES IMAGE MEASURE SATISFY PRE-SELECTED CRITERION?

NO

YES

620

INCREASE RATE OF ACQUISITION OF SECOND IMAGES

M₁₃ᵦ

622

INTERMITTENTLY OBTAIN IMAGE(S) WITH IMAGING MODALITY

624

PROCESS IMAGES AND CALCULATE IMAGE MEASURE ASSOCIATED WITH IMAGING MODALITY

626

DOES IMAGE MEASURE SATISFY PRE-SELECTED CRITERION?

NO

YES

628

INCREASE RATE OF ACQUISITION OF IMAGES $M_{17}$

732

OBTAIN WHITE LIGHT IMAGES

734

PROCESS WHITE LIGHT IMAGE(S) AND
CALCULATE IMAGE MEASURE ASSOCIATED
WITH PRESENCE OF GLARE IN WHITE LIGHT
IMAGES

736

DO ONE OR MORE
IMAGE REGIONS HAVE
AN INTENSITY
EXCEEDING A PRE-
SELECTED THRESHOLD?

NO

YES

738

ACQUIRE IMAGES WITH CROSS-POLARIZATION
IMAGING MODALITY

1900

2500

2501 a processor, configured by a set of instructions storable in relation to a nontransient memory device, to: identify the at least one device, via the tracking system operating with at least one of an electromagnetic system and a radiofrequency (RF) system, during a medical procedure; obtain at least one image of a region of interest associated with the medical procedure; process the at least one image to identify a context measure associated with a current state of the medical procedure; obtain at least one parameter for adaptively configuring the at least one device during the medical procedure, the at least one parameter customizable based on the context measure, the at least one parameter providable for the at least one device according to a prioritized list, and the at least one device reverting to a default configuration when at least one other device is removed from the region of interest; and configure the at least one device according to the at least one parameter.

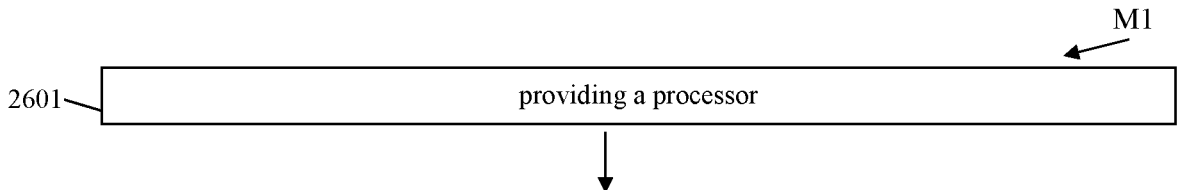

2601 — providing a processor

2602 configuring the processor by a set of instructions storable in relation to a nontransient memory device to: identify the at least one device, via the tracking system operating with at least one of an electromagnetic system and a radiofrequency (RF) system, during a medical procedure; obtain at least one image of a region of interest associated with the medical procedure; process the at least one image to identify a context measure associated with a current state of the medical procedure; obtain at least one parameter for adaptively configuring the at least one device during the medical procedure, the at least one parameter customizable based on the context measure, the at least one parameter providable for the at least one device according to a prioritized list, and the at least one device reverting to a default configuration when at least one other device is removed from the region of interest; and configure the at least one device according to the at least one parameter

FIG. 26

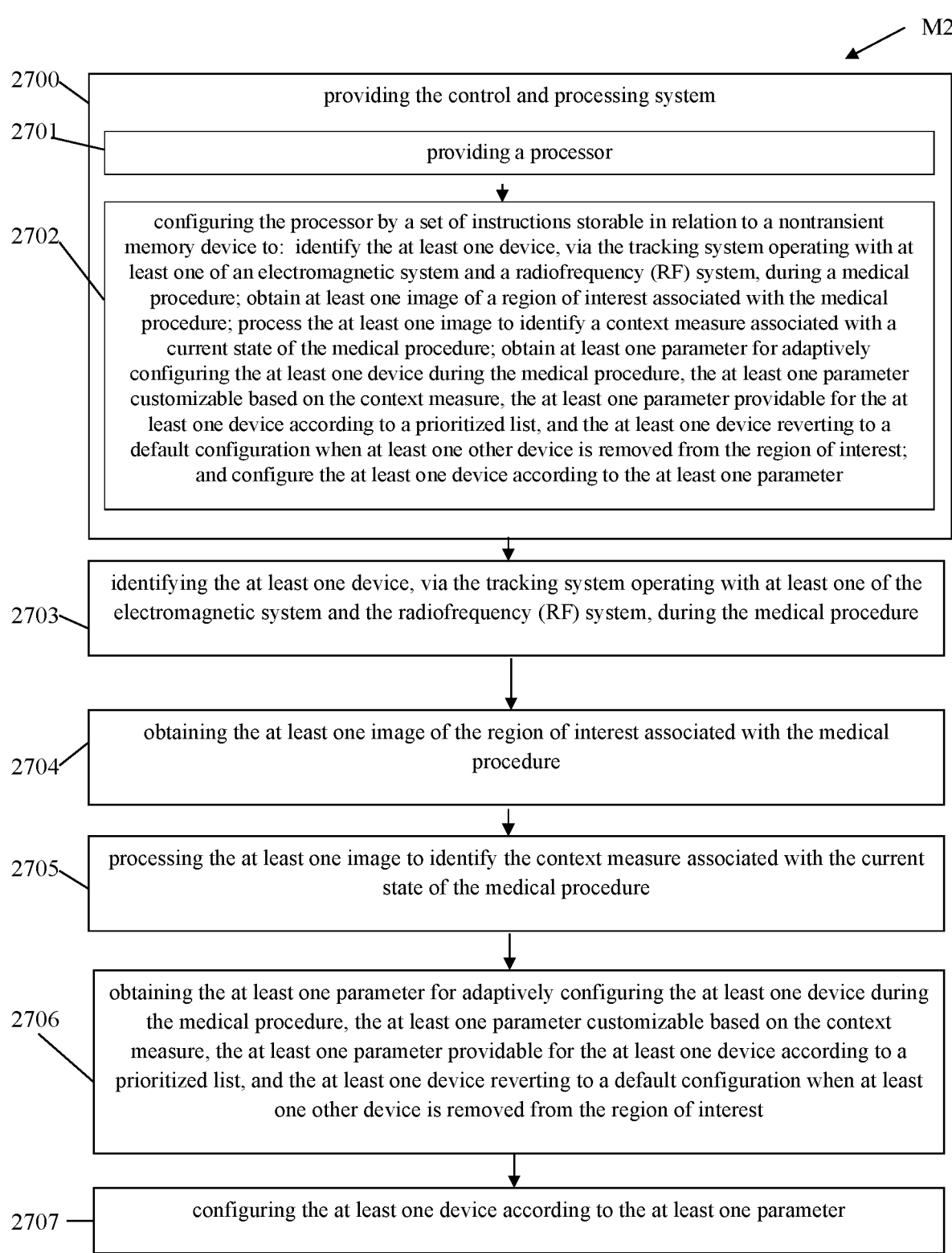

M2

2700 — providing the control and processing system

2701 — providing a processor

2702 — configuring the processor by a set of instructions storable in relation to a nontransient memory device to: identify the at least one device, via the tracking system operating with at least one of an electromagnetic system and a radiofrequency (RF) system, during a medical procedure; obtain at least one image of a region of interest associated with the medical procedure; process the at least one image to identify a context measure associated with a current state of the medical procedure; obtain at least one parameter for adaptively configuring the at least one device during the medical procedure, the at least one parameter customizable based on the context measure, the at least one parameter providable for the at least one device according to a prioritized list, and the at least one device reverting to a default configuration when at least one other device is removed from the region of interest; and configure the at least one device according to the at least one parameter 2703 — identifying the at least one device, via the tracking system operating with at least one of the electromagnetic system and the radiofrequency (RF) system, during the medical procedure 2704 — obtaining the at least one image of the region of interest associated with the medical procedure 2705 — processing the at least one image to identify the context measure associated with the current state of the medical procedure 2706 — obtaining the at least one parameter for adaptively configuring the at least one device during the medical procedure, the at least one parameter customizable based on the context measure, the at least one parameter providable for the at least one device according to a prioritized list, and the at least one device reverting to a default configuration when at least one other device is removed from the region of interest 2707 — configuring the at least one device according to the at least one parameter

FIG. 27

CONTEXT AWARE SURGICAL SYSTEMS AND METHODS VIA HYPERSPECTRAL IMAGE ANALYSIS TO CONFIGURE A DEVICE DURING MEDICAL PROCEDURE

CROSS-REFERENCE TO RELATED APPLICATIONS

This document is a continuation application, claiming the benefit of, and priority to: U.S. patent application Ser. No. 15/644,134, titled "CONTEXT AWARE SURGICAL SYSTEMS AND METHODS VIA HYPERSPECTRAL IMAGE ANALYSIS TO CONFIGURE A DEVICE DURING MEDICAL PROCEDURE," and filed on Jul. 7, 2017, U.S. patent application Ser. No. 14/771,643, titled "CONTEXT AWARE SURGICAL SYSTEMS FOR INTRAOPERA-TIVELY CONFIGURING IMAGING DEVICES," and filed on Aug. 31, 2015, International Patent Application No. PCT/CA2014/050265, titled "CONTEXT AWARE SURGI-CAL SYSTEMS," and filed on Mar. 14, 2014, U.S. Provi-sional Application Ser. No. 61/801,530, titled "SYSTEMS, DEVICES AND METHODS FOR PLANNING, IMAG-ING, AND GUIDANCE OF MINIMALLY INVASIVE SURGICAL PROCEDURES," and filed on Mar. 15, 2013, U.S. Provisional Application Ser. No. 61/800,695, titled "EXTERNAL VIDEO SCOPE FOR PORT-BASED SUR-GICAL PROCEDURES," and filed on Mar. 15, 2013, U.S. Provisional Application Ser. No. 61/800,787, titled "POLARIZED LIGHT IMAGING DEVICE," and filed on Mar. 15, 2013, U.S. Provisional Application Ser. No. 61/800,911, titled "HYPERSPECTRAL IMAGING DEVICE," and filed on Mar. 15, 2013, U.S. Provisional Application Ser. No. 61/801,746, titled "INSERT IMAGING DEVICE," and filed on Mar. 15, 2013, U.S. Provisional Application Ser. No. 61/801,143, titled "INSERTABLE MAGNETIC RESO-NANCE IMAGING COIL PROBE FOR MINIMALLY INVASIVE CORRIDOR-BASED PROCEDURES," and filed on Mar. 15, 2013, U.S. Provisional Application Ser. No. 61/801,282, titled "SYSTEMS AND METHODS FOR PATHOLOGY TRACKING," and filed on Mar. 15, 2013, U.S. Provisional Application Ser. No. 61/800,155, titled "PLANNING, NAVIGATION AND SIMULATION SYS-TEMS AND METHODS FOR MINIMALLY INVASIVE THERAPY," and filed on Mar. 15, 2013, U.S. Provisional Application Ser. No. 61/818,255, titled "INSERT IMAG-ING DEVICE" and filed on May 1, 2013, U.S. Provisional Application Ser. No. 61/818,325, titled "INSERTABLE MAGNETIC RESONANCE IMAGING COIL PROBE FOR MINIMALLY INVASIVE CORRIDOR-BASED PROCEDURES," and filed on May 1, 2013, U.S. Provi-sional Application Ser. No. 61/818,280, titled "SYSTEMS, DEVICES AND METHODS FOR PLANNING, IMAG-ING, AND GUIDANCE OF MINIMALLY INVASIVE SURGICAL PROCEDURES," and filed on May 1, 2013, U.S. Provisional Application Ser. No. 61/818,223, titled "IMAGING ASSEMBLY FOR ACCESS PORT-BASED MEDICAL PROCEDURES," and filed on May 1, 2013, and U.S. Provisional Application Ser. No. 61/924,993, titled "PLANNING, NAVIGATION AND SIMULATION SYS-TEMS AND METHODS FOR MINIMALLY INVASIVE THERAPY," and filed on Jan. 8, 2014, all of which are hereby incorporated herein by reference in their entirety.

FIELD

The present disclosure generally relates to image-guided medical procedures.

BACKGROUND

In the field of surgery, imaging and imaging guidance is becoming a more significant component of clinical care, from diagnosis of disease, monitoring of the disease, plan-ning of the surgical approach, guidance during the procedure and follow-up after the procedure is complete, or as part of a multi-faceted treatment approach. Integration of imaging data in the surgical suite has become common-place for neurosurgery, wherein brain tumors are typically excised through an open craniotomy approach that is guided by imaging. The data that is typically used consists of CT scans with associated contrast (iodinated contrast) and MRI scans with associated contrast (gadolinium contrast). Systems provide a way to register the imaging data sets together; and registration methods provide a way of translating the three dimensional imaging space to the three dimensional space of the patient, tracking instruments relative to the patient, and associating imaging data by way of an external hardware system, such as a mechanical arm, a radio-frequency, or optical tracking device.

SUMMARY

Systems and methods are provided in which devices, that are employed during a medical procedure, are adaptively configured during the medical procedure, based on input or feedback that is associated with the current state, phase, or context of the medical procedure, in accordance with embodiments of the present disclosure. In some example embodiments, the input is obtained via the identification of one or more medical instruments present within a region of interest; and this input is employed to determine configu-ration parameters for configuring the device. In other example embodiments, the input is based on the image-based detection of a measure that is associated with the phase or context of the medical procedure; and this input may be employed to adaptively control the device, based on the inferred context or phase of the medical procedure. In other embodiments, images from one imaging modality are employed to adaptively switch to another imaging modality.

Accordingly, in one aspect, a computer implemented method of adaptively and intraoperatively configuring a device used during a medical procedure is provided, the method comprising: identifying a medical instrument during the medical procedure; obtaining one or more customized configuration parameters for adaptively configuring the device during the medical procedure, where the customized configuration parameters are selected based on the identity of the medical instrument; and configuring the device according to the customized configuration parameters.

In another aspect, a system for adaptively and intraop-eratively configuring a device used during a medical proce-dure is provided, the system comprising: a data storage device comprising customized configuration parameters for adaptively configuring one or more devices during the medical procedure; a control and processing system inter-faced with the device and the data storage device, said control and processing system comprising one or more processors and memory coupled to said one or more pro-cessors, said memory storing instructions, which, when executed by said one or more processors, causes said one or more processors to perform operations comprising: identi-fying a medical instrument during the medical procedure; obtaining, from the data storage device, one or more cus-tomized configuration parameters for adaptively configuring the device during the medical procedure, where the customized configuration parameters are customized based on the identity of the medical instrument; and configuring the device according to the customized configuration parameters.

In another aspect, a computer implemented method of adaptively configuring a device used during a medical procedure is provided, the method comprising: obtaining one or more images of a region of interest associated with the medical procedure; processing the one or more images to identify a context measure associated with the current state of the medical procedure; obtaining one or more customized configuration parameters for adaptively configuring the device during the medical procedure, where the customized configuration parameters are customized based on the context measure; and configuring the device according to the customized configuration parameters.

In another aspect, a system for adaptively and intraoperatively configuring a device used during a medical procedure is provided, comprising: a data storage device comprising customized configuration parameters for adaptively configuring one or more devices during the medical procedure; a control and processing system interfaced with the device and the data storage device, said control and processing system comprising one or more processors and memory coupled to said one or more processors, said memory storing instructions, which, when executed by said one or more processors, causes said one or more processors to perform operations comprising: obtaining one or more images of a region of interest associated with the medical procedure; processing the one or more images to identify a context measure associated with the current state of the medical procedure; obtaining one or more customized configuration parameters for adaptively configuring the device during the medical procedure, where the customized configuration parameters are customized based on the context measure; and configuring the device according to the customized configuration parameters.

In another aspect, a computer implemented method of adaptively controlling a first imaging modality and a second imaging modality during a medical procedure is provided, the method comprising: while obtaining first images with the first imaging modality, intermittently obtaining one or more second images with the second imaging modality; processing the second images to calculate, for a plurality of regions within the second images, an image measure associated with the second imaging modality; and in the event that the image measure for one or more regions is within a pre-selected range, increasing the rate of acquisition of the second images.

In another aspect, a system for adaptively controlling one or more imaging devices during a medical procedure is provided, the system comprising: a control and processing system interfaced with the one or more imaging devices, said control and processing system comprising one or more processors and memory coupled to said one or more processors, said memory storing instructions, which, when executed by said one or more processors, causes said one or more processors to perform operations comprising: obtaining first images with a first imaging modality and intermittently obtaining one or more second images with a second imaging modality; processing the second images to calculate, for a plurality of regions within the second images, an image measure associated with the second imaging modality; and in the event that the image measure for one or more regions is within a pre-selected range, increasing the rate of acquisition of the second images.

In another aspect, a computer implemented method of adaptively controlling one or more imaging devices during a medical procedure is provided, the method comprising: obtaining one or more first images with a first imaging modality; processing the first images to calculate, for a plurality of regions within the first images, an image measure associated with the suitability of a second imaging modality; in the event that the image measure for one or more regions lies within a pre-selected range, acquiring one or more second images with the second imaging modality.

In another aspect, a system for adaptively controlling one or more imaging devices during a medical procedure is provided, the system comprising: a control and processing system interfaced with the one or more imaging devices, said control and processing system comprising one or more processors and memory coupled to said one or more processors, said memory storing instructions, which, when executed by said one or more processors, causes said one or more processors to perform operations comprising: obtaining one or more first images with a first imaging modality; processing the first images to calculate, for a plurality of regions within the first images, an image measure associated with the suitability of a second imaging modality; in the event that the image measure for one or more regions lies within a pre-selected range, acquiring one or more second images with the second imaging modality.

In another aspect, a method of performing adaptive illumination while performing optical imaging during a medical procedure is provided, the method comprising: determining the field of view of an optical imaging device employed during the medical procedure; determining configuration parameters of an illumination source for improving the homogeneity of illumination within the field of view; configuring the illumination source according to the configuration parameters.

In another aspect, a system for performing adaptive illumination while performing optical imaging during a medical procedure is provided, the system comprising: a control and processing system interfaced with the optical imaging device and the illumination source, said control and processing system comprising one or more processors and memory coupled to said one or more processors, said memory storing instructions, which, when executed by said one or more processors, causes said one or more processors to perform operations comprising: determining the field of view of an optical imaging device employed during the medical procedure; determining configuration parameters of an illumination source for improving the homogeneity of illumination within the field of view; configuring the illumination source according to the configuration parameters.

A further understanding of the functional and advantageous aspects of the present disclosure is realized by reference to the following detailed description and drawings.

BRIEF DESCRIPTION OF THE DRAWINGS

Embodiments of the present disclosure are described, by way of examples only, with reference to the several figures of the drawings, in which:

FIG. 5C is a table illustrating configuration data associating configuration parameters for a camera with the identity of various medical instruments;

FIG. 5D is a table illustrating configuration data associating configuration parameters for an imaging optics assembly with the identity of various medical instruments;

FIG. 5E is a table illustrating configuration data associating configuration parameters for an illuminator with the identity of various medical instruments;

FIG. 5F is a table illustrating configuration data associating configuration parameters for illuminator focusing optics with the identity of various medical instruments;

FIG. 5G is a table illustrating configuration data associating configuration parameters for a camera with a ranked list of medical instruments;

FIG. 5H is a table illustrating configuration data associating configuration parameters for a camera with the identity of various medical instruments, including configuration parameters associated with the absence of a detected medical instrument;

FIG. 5I is a table illustrating configuration data associating configuration parameters for a camera with the identity of various medical instruments, wherein the configuration parameters are further associated with the type of medical procedure being performed;

FIG. 5J is a table illustrating configuration data associating configuration parameters for a camera with the identity of various medical instruments, wherein the configuration parameters are further associated with the phase of the medical procedure;

FIG. 5K is a table illustrating configuration data associating configuration parameters for a robotic arm with the identity of various medical instruments;

FIG. 5L is a table illustrating configuration data associating configuration parameters for a user interface with the identity of various medical instruments;

FIG. 10A is a flow chart illustrating a method of performing tissue identification via hyperspectral imaging;

FIG. 10B is a table illustrating configuration data that associates configuration parameters for illuminators with one or more tissue types;

FIG. 11A is a flow chart illustrating a method of identifying the phase of a medical procedure based on hyperspectral imaging;

FIG. 11B is a table illustrating configuration data that associates configuration parameters for a camera with the phase of a medical procedure;

FIG. 25 is a schematic diagram illustrating a control and processing system for adaptively configuring at least one device used during a medical procedure;

FIG. 26 is a flow diagram illustrating a method of providing a control and processing system for adaptively configuring at least one device used during a medical procedure; and FIG. 27 is a flow diagram illustrating a method of adaptively configuring at least one device used during a medical procedure by way of a control and processing system.

DETAILED DESCRIPTION

Figure 1:
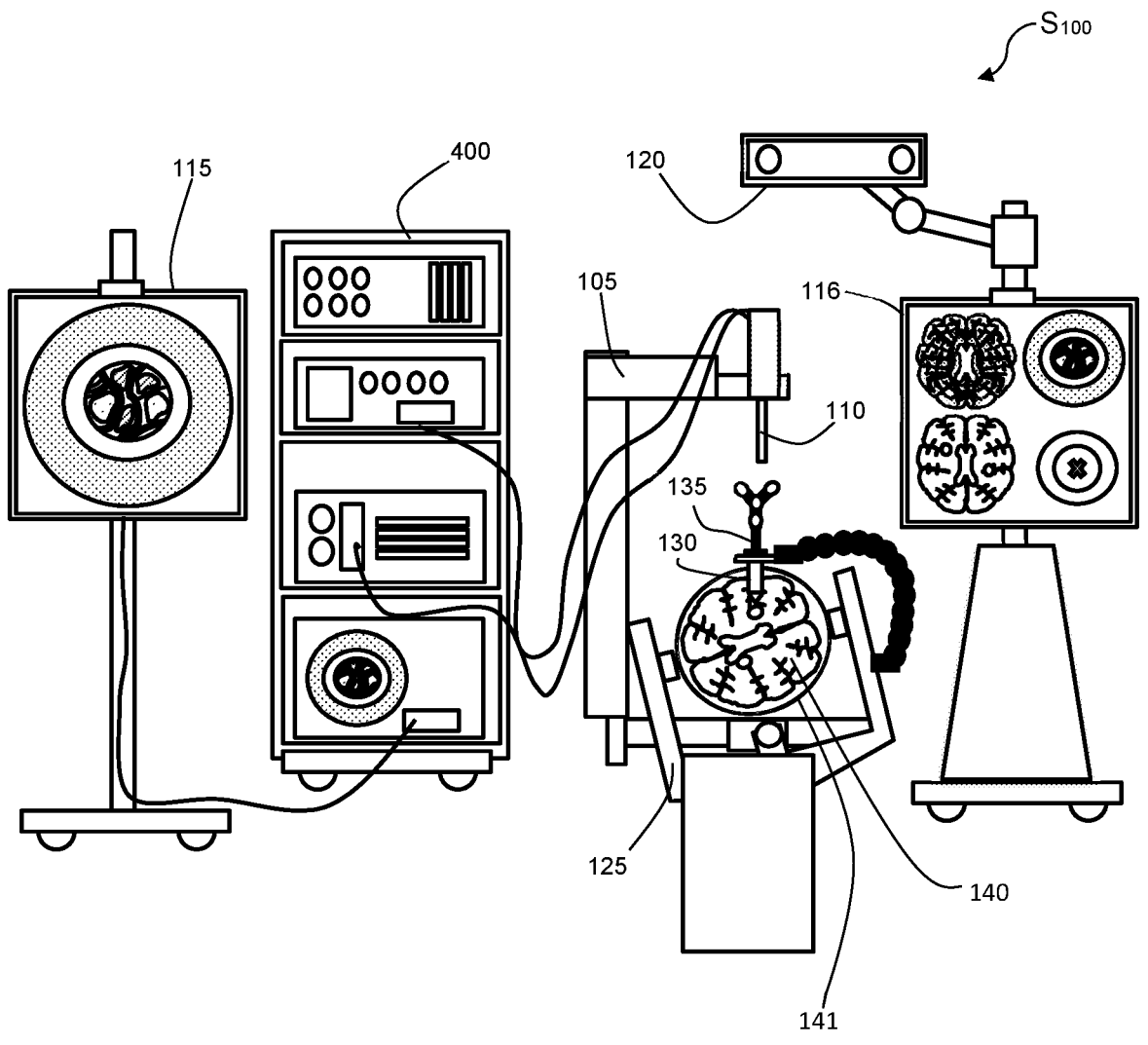
FIG. 1 is a diagram illustrating an automated system for a minimally-invasive neurological surgical procedure employing an access port.

Various embodiments and aspects of the present disclosure will be described with reference to details below discussed. The following description and drawings are illustrative of the present disclosure and are not to be construed as limiting the present disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" as well as variations thereof denote the specified features, steps, or components that are included. These terms are not to be interpreted to exclude the presence of other features, steps, or components.

As used herein, the term "exemplary" denotes "serving as an example, instance, or illustration," and should not be construed as preferred or advantageous over other configurations disclosed herein.

As used herein, the terms "about" and "approximately" are intended to cover variations that may exist in the upper and lower limits of the ranges of values, such as variations in properties, parameters, and dimensions. In one non-limiting example, the terms "about" and "approximately" denote plus or minus 10 percent or less.

Unless defined otherwise, all technical and scientific terms used herein are intended to have the same meaning as commonly understood to one of ordinary skill in the art. Unless otherwise indicated, such as through context, as used herein, the following terms are intended to have the following definitions:

As used herein, the phrase "medical instrument" refers to a tool, instrument, or other implement that is employed during a medical procedure. A medical instrument may be provided in various forms, such as, but not limited to, a handheld, or robotically positioned, tool, or a component that is attached to, or inserted into, a patient during a surgical or medical procedure. Non-limiting examples of medical instruments include, but are not limited to, scalpels, bi-polar devices, suction devices, cutting devices, clamping devices, access ports, imaging devices, spectroscopy devices, and suturing tools.

As used herein, the phrase "operator" refers to a user, medical practitioner, surgeon, imaging technician, other individual, or a group of individuals that is/are involved in operating medical instruments, devices, and equipment during a medical procedure.

As used herein, the phrase "tracking system" refers to a system configured to track the position and/or orientation of one or more objects, such as locations on a patient and/or surgical instruments. In some embodiments, the tracking system may be configured to track the position and/or orientation of an imaging device, such as an optical camera. A tracking system may also be employed to track the position and/or orientation of an access port or other component that is attached to, or inserted into, a patient or subject. In one example, a tracking system may employ a pair of infrared cameras to track the position and orientation of active or passive infrared spheres (fiducial markers) attached to one or more objects, such as the Polaris® system from NDI.

As used herein, the phrase "navigation system" refers to a system that processes and spatially registers pre-operative image data to an interoperative reference frame and that displays the position and orientation of one or more tracked items relative to the pre-operative image data. A navigation system may interface with, or include, a tracking system, in order to track the items. In some example implementations, hardware associated with the navigation system may include a computer system, a display, and a tracking system.

As used herein, the phrase "phase of the medical procedure" refers to a given step, or set of sequential steps, within a medical procedure. In another example, a phase of a medical procedure need not be a given step, or set of sequential steps, in a procedure, but may relate to the use of a specific tool, or set of tools, within a given step of a medical procedure.

As used herein the phrase "intraoperative" refers to an action, process, method, event, or step that occurs or is carried out during at least a portion of a medical procedure. Intraoperative, as defined herein, is not limited to surgical procedures and may refer to other types of medical procedures, such as diagnostic and therapeutic procedures.

As used herein, the phrase "access port" refers to a cannula, conduit, sheath, port, tube, or other structure that is insertable into a subject, in order to provide access to internal tissue, organs, or other biological substances. In some embodiments, an access port may directly expose internal tissue, for example, via an opening or aperture at a distal end thereof, and/or via an opening or aperture at an intermediate location along a length thereof. In other embodiments, an access port may provide indirect access, via one or more surfaces that are transparent, or partially transparent, to one or more forms of energy or radiation, such as, but not limited to, electromagnetic waves and acoustic waves.

Presently, many devices that are employed during a medical procedure are controlled independently of the actions that are being performed during the procedure. For example, lighting systems typically operate in an independent manner, e.g., without receiving any controlling input that is associated with the current phase or context of a medical procedure. In another example, external imaging devices, such as endoscopes, are usually independently activated and independently controlled by an operator while a medical procedure is being performed.

Several embodiments of the present disclosure provide systems and methods in which devices, employed during a medical procedure, are adaptively and dynamically configured and/or controlled during the medical procedure, based on input or feedback that is associated with the current phase or context of the medical procedure. In some example embodiments, the input is obtained via the identification of one or more medical instruments present within a region of interest, such as a surgical field; and this input is employed to determine configuration parameters for configuring the device. In other example embodiments, the input is based on the image-based detection of a measure associated with the phase or context of the medical procedure, and this input is employed to adaptively control the device based on the inferred context or phase of the medical procedure. In still other embodiments, images from one imaging modality are employed to adaptively switch to another imaging modality. These and other example embodiments are below described in detail.

Referring to FIG. 1, this diagram illustrates an example automated system $S_{100}$ for performing various embodiments of the present disclosure, providing a non-limiting example pertaining to a minimally-invasive neurological surgical procedure employing an access port. The example automated system includes an automated robotic arm 105, which supports an optical video scope 110 (and associated illumination), a video display 115 for displaying a video image from optical video scope 110, a navigation display 116 for providing a navigation user interface, a tracking device 120 for tracking various medical instruments within the surgical field, and a control and processing unit 400 for controlling various devices, such as the robotic arm 105, and providing surgical navigation. A patient's head 141 is held in place by a head holder 125. An access port 130 and an introducer 135 (having fiducial markers attached thereto) are inserted into the head 141. The introducer 135 is received within access port 130 and tracked by using the tracking device 120, e.g., of a tracking system.

Still referring to FIG. 1, the position of the patient may be initially determined and/or continuously tracked intraoperatively by the tracking device 120, e.g., of the tracking system. A set of preoperative images, associated with the anatomy of interest of the patient, are obtained prior to surgery. These images are intraoperatively registered to the patient, for example, by way of surface matching, sets of known touch points (tip of nose, temple, ears) and/or fiduciary markings that are identified on the patient and in the associated images. These points or surfaces are registered to the tracking coordinate frame through a defined registration process. Once registered, medical instruments, and the associated patient images are tracked in real-time, and shown in various manners on a computer monitor.

Still referring to FIG. 1, the example automated system is configured for implementation in minimally invasive brain surgery, using an access port 130, to provide a conduit within the head 141, allowing access to internal brain tissue of the brain 140 (FIG. 2) for surgical, therapeutic, or diagnostic applications. An access port 130, e.g., an intracranial access port, is employed in neurological procedures in order to provide access to internal tissue pathologies, such as tumors. One example of an intracranial access port is the BrainPath® surgical access port, provided by NICO®, which is inserted into the brain 140 via an obturator, e.g., the introducer 135, with an atraumatic tip in the brain 140. Such an access port 130 is employed during a surgical procedure, e.g., by inserting the access port 130, via the obturator, e.g., the introducer 135, that is received within the access port 130, to access an internal surgical site.

Figure 2:
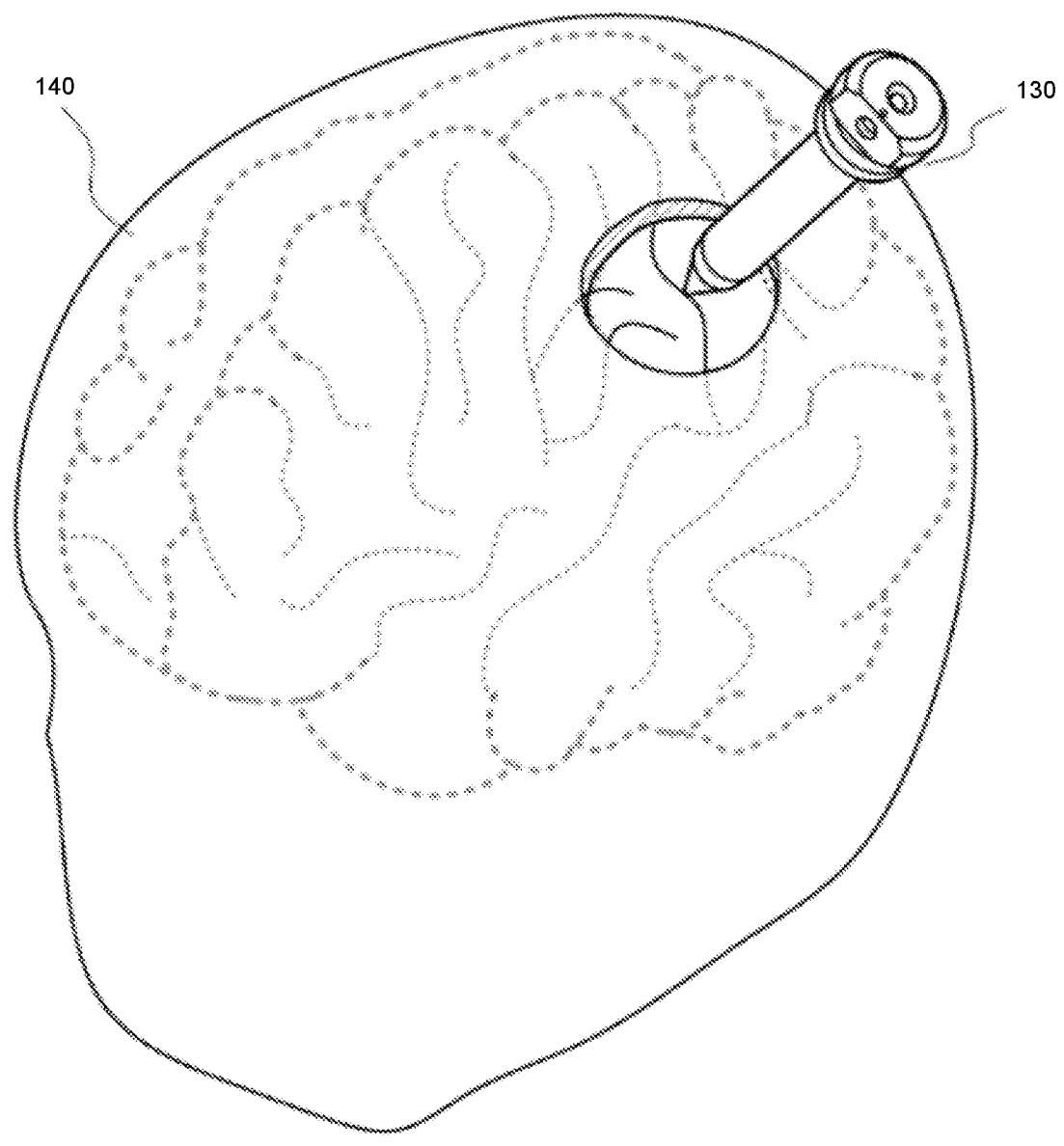
FIG. 2 is a diagram illustrating a human brain into which an access port has been inserted, thereby establishing an open conduit for providing access to tissue within the brain.

Referring to FIG. 2, this diagram illustrates the use of an access port 130, showing the brain 140, e.g., a human brain, into which the access port 130 has been inserted, thereby establishing an open conduit providing access to tissue deep within the brain 140, in accordance with an embodiment of the present disclosure. Surgical instruments may then be inserted within the lumen of the access port 130 in order to perform surgical, diagnostic or therapeutic procedures, such as resecting tumors as necessary. This approach allows a surgeon, or robotic surgical system, to perform a surgical procedure involving tumor resection in which the residual tumor remaining after is minimized, while also minimizing the trauma to the intact white and grey matter of the brain 140. In such procedures, trauma may occur, for example, due to contact with the access port 130, stress to the brain matter, unintentional impact with surgical devices, and/or accidental resection of healthy tissue. For example, access port based procedures are employed for other surgical interventions for other anatomical regions, such as, but not limited to, spine, knee, and any other region of the body that will benefit from the use of the access port 130 or small orifice to access the interior of the human body.

Referring back to FIG. 1, in order to introduce the access port 130 into the brain 140, the introducer 135 with an atraumatic tip is positioned within the access port 130 and employed to position the access portion within the head 141. The introducer 135 (or the access port 130) comprises fiducial markers for tracking. These fiducial markers may be passive or active fiducial markers, such as reflective spheres for passive infrared detection via an optical camera, or, for example, pick-up coils in the case of an electromagnetic tracking system. The fiducial markers are detected by the tracking device 120, e.g., of the tracking system, and their respective positions are inferred by tracking software which may reside within the tracking system, or may reside, for example, within the control and processing unit 400. Once the access port 130 is inserted into the brain 140, the introducer 135 is removed to allow for access to the tissue through the central opening of access port 130. However, once the introducer 135 is removed, the access port 130 can no longer be directly tracked in real time, wherein fiducial markers are not attached to the access port 130. In order to track the position and the orientation of the access port 130, the access port 130 is indirectly and intermittently tracked by a pointer tool having fiducial markers that are detectable by the tracking device 120, e.g., of the tracking system.

Still referring back to FIG. 1, although the example system relates to a neurosurgical procedure, the systems and methods described herein are not intended to be limited to neurosurgical procedures or port-based procedures and may be employed for a wide range of medical procedures. Examples of other types of medical procedures including orthopedic, trauma, gastrological, cardiac, gynecological, abdominal, ENT, oral and maxillofacial, urological, dental, and other surgical, diagnostic, or therapeutic medical procedures. While many of the example embodiments described herein employ external imaging, such as imaging with an external video scope, various internal imaging devices, such as endoscopic or catheter imaging devices, may additionally or alternatively be employed. Embodiments of the present disclosure may be employed within, or adapted to, procedures employing telesurgical or shared-control systems.

Referring back to FIGS. 1 and 2 and ahead to FIGS. 3-24, in many of the example embodiments below described, each medical device, e.g., each medical instrument, that is to be tracked may have fiducial markers attached thereto, e.g., passive or active fiducial markers, such as reflective spheres or active LED lighting emitted from at least three points on a medical instrument, so that the position and orientation of the instrument can be determined. In one example implementation, the fiducial markers are employed to determine a reference position on medical instrument, such as a central point, and an axis of the medical instrument (such as a longitudinal axis of a tool). In some embodiments, the identification of one or more medical instruments, as described above, is employed to adaptively or dynamically provide configuration parameters for controlling one or more devices, e.g., medical devices, that are employed within a medical procedure. A "configuration parameter," as used herein, refers to a parameter for adjusting the configuration of a device, e.g., medical device, as opposed to an instruction or signal that is employed to activate (turn on) the device, e.g., medical device.

Referring back to FIGS. 1 and 2 and ahead to FIGS. 3-24, this method of actively determining configuration parameters for a device, e.g., medical device, is to be contrasted with methods in the related art in which a device is activated, or powered on, based on the identification of a surgical tool. Such an "activating" method is disclosed in US Patent Application Publication No. US 2014/0006049 (de la Barrera et al.). One example disclosed in US 2014/0006049 involves automatically activating a suction device when the suction device is identified near a surgical incision.

Referring back to FIGS. 1 and 2 and ahead to FIGS. 3-24, merely activating a device, e.g., medical device, based on the identification of a tool, is often insufficient. Specifically, many devices that are employed during a medical procedure are not configured merely in a simple binary manner. Such devices have more complex states than simply being either in an "on" state or in an "off" state. Many devices that are employed during a medical procedure are operated according to a set of configuration parameters. Accordingly, in some example embodiments of the present disclosure, a device employed during a medical procedure is dynamically controlled via selection of configuration parameters that are intraoperatively determined, e.g., customized, based on the identification of a medical instrument. In some embodiments, the medical instrument need not be tracked by the tracking system, provided that the medical instrument can be identified.

Figure 3:
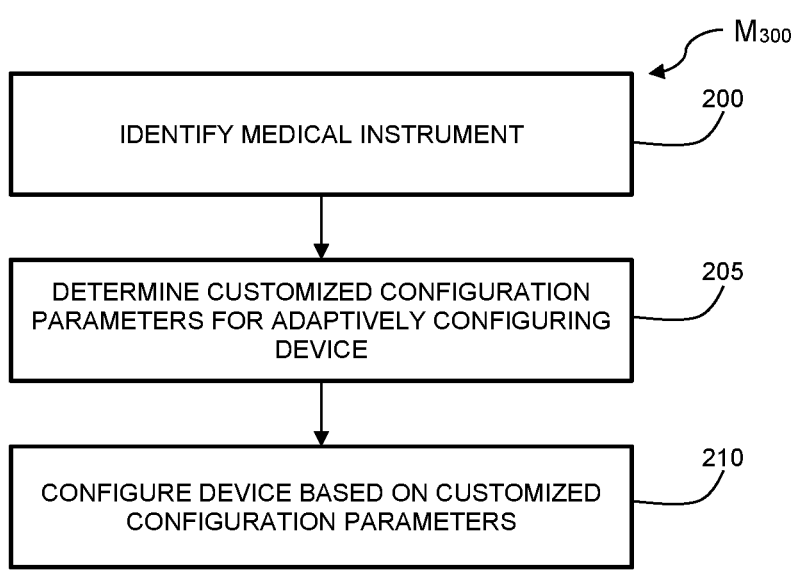
FIG. 3 is a flow chart illustrating a method of intraoperatively determining parameters, such as configuration parameters, for a device, based on the intraoperative identification of a medical instrument.

Referring to FIG. 3, this flow chart illustrates a method $M_{300}$ of intraoperatively determining configuration parameters for a device, based on the intraoperative identification of a medical instrument, in accordance with an embodiment of the present disclosure. At step 200, a medical instrument is intraoperatively identified, as below described. The identity of the medical instrument is then employed to determine customized configuration parameters for adaptively and intraoperatively configuring at least one device. The configuration parameters are obtained from pre-selected configuration data associating customized configuration parameters for one or more devices with the identities of different medical instruments. In step 210, the customized configuration parameters are employed to adaptively configure the device during the medical procedure. For example, the configuration parameters are employed to generate suitable commands, transmitted from the control and processing unit 400 to a device, to be executed by the device firmware for reconfiguring the device.

Figure 4:
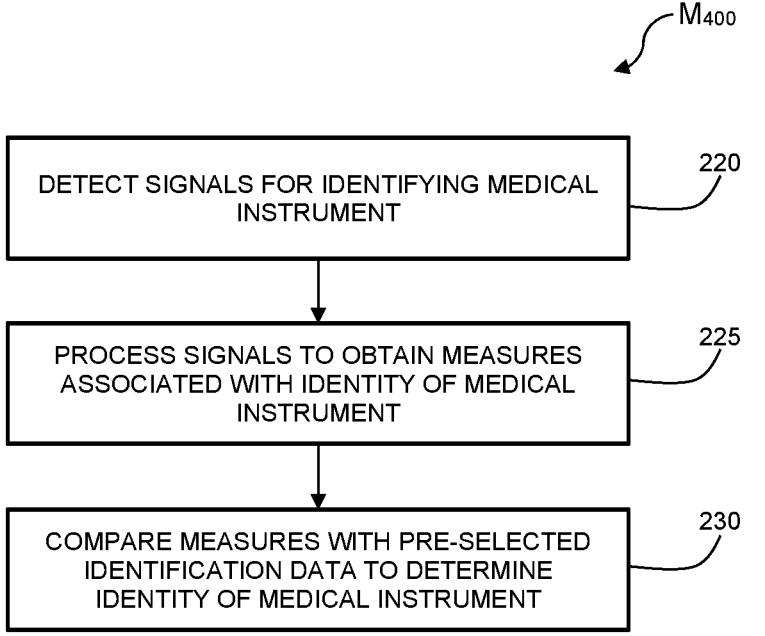
FIG. 4 is a flow chart illustrating a method of identifying a medical instrument.

Referring to FIG. 4, this flow chart illustrates a method $M_{400}$ of identifying a medical instrument, in accordance with an embodiment of the present disclosure. The identification of the medical instrument is performed, for example, as follows. In step 220, one or more signals associated with the medical instrument are detected. The signals are, for example, images showing the medical instrument and/or fiducial markers attached to the medical instrument, optical signals emitted from markers attached to the medical instrument, e.g., pulses from an active fiducial marker, and RFID signals emitted from RFID tags attached to the medical instrument. These signals are processed to obtain one or more identification measures associated with the identity of the medical instrument, such as an RFID tag value, e.g., a code associated with an optical pulse sequence, as shown in step 225. The identity of the medical instrument is then obtained, as shown in step 230, by comparing the identification measures with pre-selected identification data, wherein the pre-selected identification data associates the identities of a plurality of medical instruments with various measures. The identification data is provided in the form of a database, look-up table, or other data structure that is accessed by the control and processing unit 400 to identify the medical instrument.

Still referring to FIG. 4, in one example embodiment, the identity of a medical instrument is determined based on a unique spatial arrangement of fiducial markers attached to the medical instrument. In such a case, the detected signal comprises a signal relating to stereoscopic images obtained by the tracking system. The stereoscopic images that are processed determine the positions of passive fiducial markers attached to the medical instrument. The measures associated with the identity of the medical instrument are obtained as the relative distances (and/or angles) between the fiducial markers. These measures are compared to a look-up table that correlates the identities of different medical instruments with different relative marker distances or angles. The table entry, having relative marker distances or angles that match the calculated measures, provides a determination of the identity of the medical instrument.

Still referring to FIG. 4, in another example implementation, a medical instrument is identified, based on marker geometry, e.g., using passive optical systems. For example, a medical instrument is identified by the size and/or shape of the fiducial markers. In such a case, the identification data correlates the geometry of the fiducial markers with the identities of various medical instruments. In other example implementations, a medical instrument employs active fiducial markers. The characteristics of the active fiducial markers are employed to identify the medical instrument. For example, active fiducial markers comprise pulsed optical devices, such as light emitting diodes, wherein the pulsed pattern is employed to identify a medical instrument. The associated identification data comprises information, for a plurality of different medical instruments, correlating the characteristic of the active fiducial markers, e.g., a pulse sequence, with the identity of each medical instrument.

Still referring to FIG. 4, in another example, glyphs, barcodes, and other symbolic, graphic, or textual markers are employed to identify a medical instrument. For example, one or two-dimensional barcodes are employed to provide detectable information identifying a medical instrument. In such a case, the identification data correlates the graphical symbol, a code, or other information extractable from the graphical symbol, with the identities of various medical instruments. In other example embodiments, electromagnetic and/or radiofrequency (RF) systems are employed to identify and/or differentiate medical instruments based on an electrical trigger, rather than geometry constraints. For example, a medical instrument may be identified based on radio-frequency identification (RFID) signals.

Figure 19:
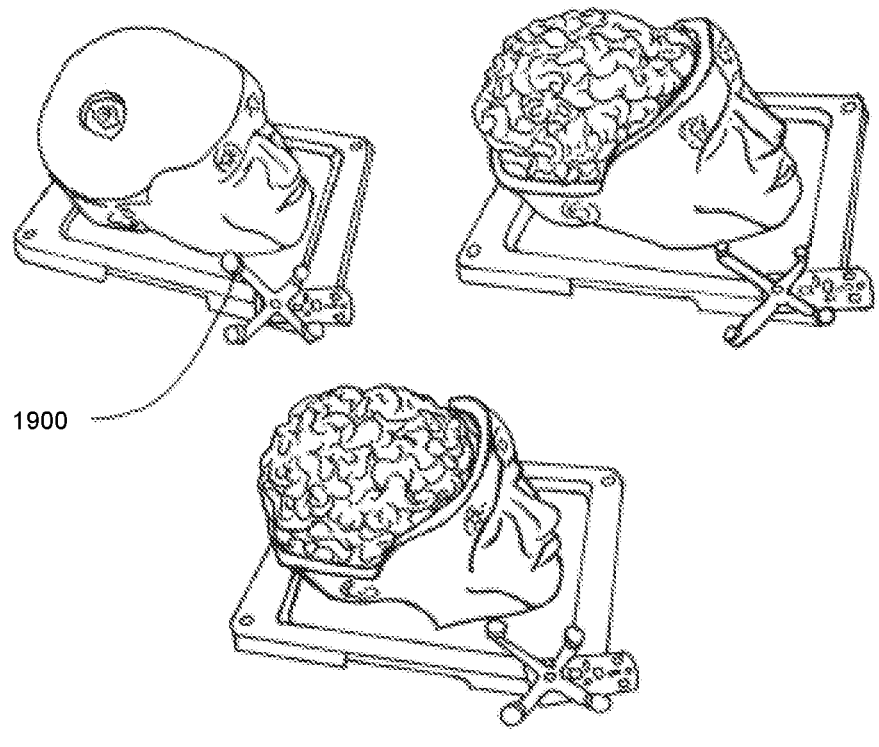
FIG. 19 is a diagram illustrating a mock head, a mock brain, and a mock head holder of a patient with a tracking marker reference.

Still referring to FIG. 4, these tools may be tracked relative to a second set of reflective or active points, or some other known point with respect to the patient's anatomy and the tracking system, such as the tracking detector itself, which define the system reference frame. For example, a rigid piece of stainless steel (patient reference) is rigidly attached to the head-holder 125 and has an arrangement of passive reflective fiducial markers 1900, as shown in FIG. 19. The tracking camera 120 will, once having identified the location of this patient reference, establish a coordinate system with the origin based at this patient reference 1900 and then report the position and the orientation of other tools with respect to this coordinate system.

Still referring to FIG. 4, although some of the preceding examples pertain to fiducial markers that are capable of performing a dual role of position/alignment sensing and instrument identification, these roles may be decoupled in some embodiments, such that one or more fiducial markers are provided for the tracking of a medical instrument and one or more additional identifying markers are provided for identifying a medical instrument. In such embodiments, the system employs one or more additional cameras in order to image the identifying markers; and the system comprises an image processing module for processing the images to obtain one or more measures associated with the identity of the medical instrument. In such an embodiment, the additional cameras are spatially registered to the reference frame of the tracking system in order to correlate the position of an identified marker within the image with the position of the medical device tracked by the tracking system, which may be performed by control and processing unit 400.

Figure 20:
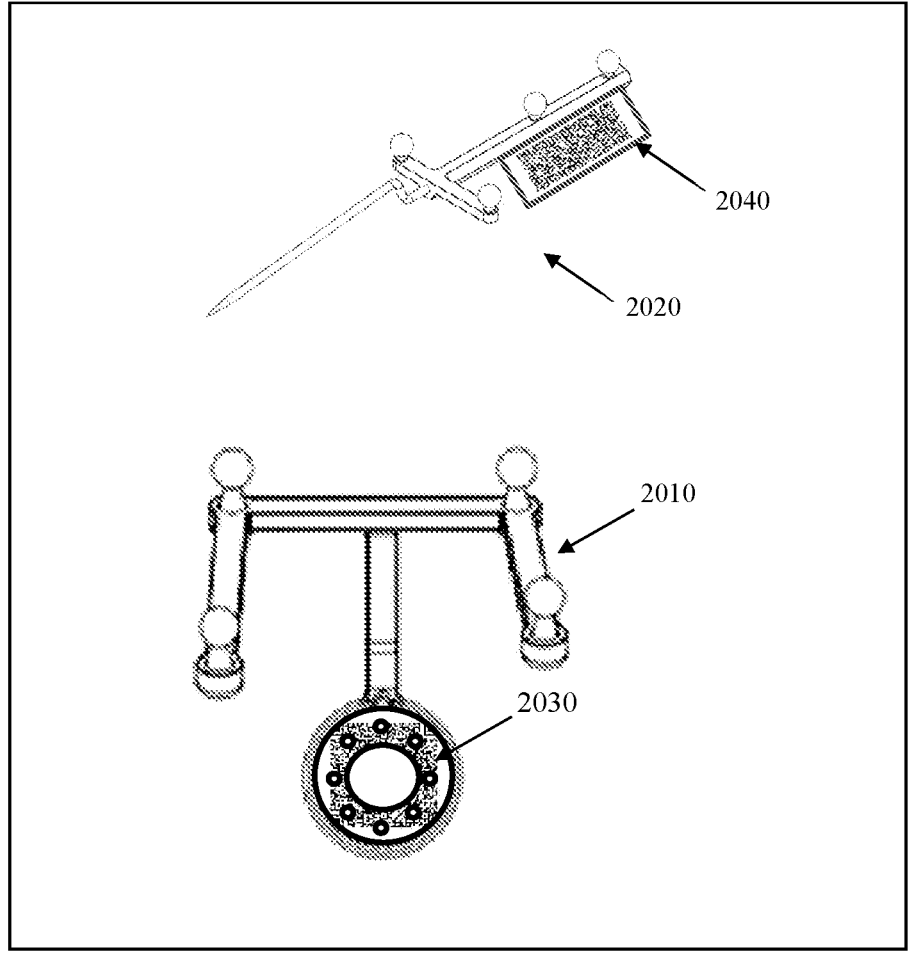
FIG. 20 is a diagram illustrating medical instruments with corresponding tracking templates and optical tracking markers.

Still referring to FIG. 4, in one illustrative implementation, a medical instrument is provided with a set of passive infrared fiducial markers for tracking and one or more two-dimensional barcodes for instrument identification. In some embodiments, two or more identifying markers are positioned at a plurality of locations to avoid shadowing and line-of-sight issues. Unlike tracking, which requires continuous detection of fiducial markers, identification of a medical instrument need only be performed once when the medical instrument enters the region of interest or surgical field, as once a medical instrument is identified, its identity can be continuously associated with its tracked location through its unique tracking marker. In another example embodiment, the images obtained by an additional camera are processed to identify a medical instrument, based on a known instrument shape, known markings, or known features that are imaged, for example. the templates 2040, 2030 respectively located on the medical instruments 2020, 2040, as shown in FIG. 20. These templates or instrument shapes are identified by using any of the methods described in the paper, Monocular Model-Based 3D Tracking of Rigid Objects: A Survey, section 4, Lepetit, Vincent, and Pascal Fua, Now Publishers Inc, 2005.

Still referring to FIG. 4, although the preceding examples disclose embodiments in which a medical instrument is both tracked and identified, in some embodiments, identification of a medical instrument is performed without tracking the medical instrument. For example, some medical instruments are employed without fiducial markers for tracking. Such non-tracked medical instruments are nonetheless identified by any of the preceding example methods or any other suitable identification methods. In another example implementation, a medical instrument is identified, based on input from an operator. The preceding examples of devices and methods for identifying a medical instrument are provided as a non-limiting set of illustrative embodiments. Additional or alternative devices or methods may be employed to identify a medical instrument without departing from the scope of the present disclosure.

Referring back to FIG. 3, after having identified a medical instrument in step 200, customized configuration parameters are obtained for adaptively configuring one or more devices that are employed during a medical procedure. The one or more devices for which configuration parameters are provided are selected from a wide variety of configurable devices that are employed during a medical procedure. For example, a device that is adaptively configured, according to the present disclosure, may be another medical instrument that is not connected, or connectable, to the identified medical instrument. In another example implementation, a device for which configuration parameters are provided, based on the identification of the medical instrument, comprises an auxiliary device, such as, but not limited to, an illumination device, video and sound recording devices, and imaging devices.

Figure 5A:
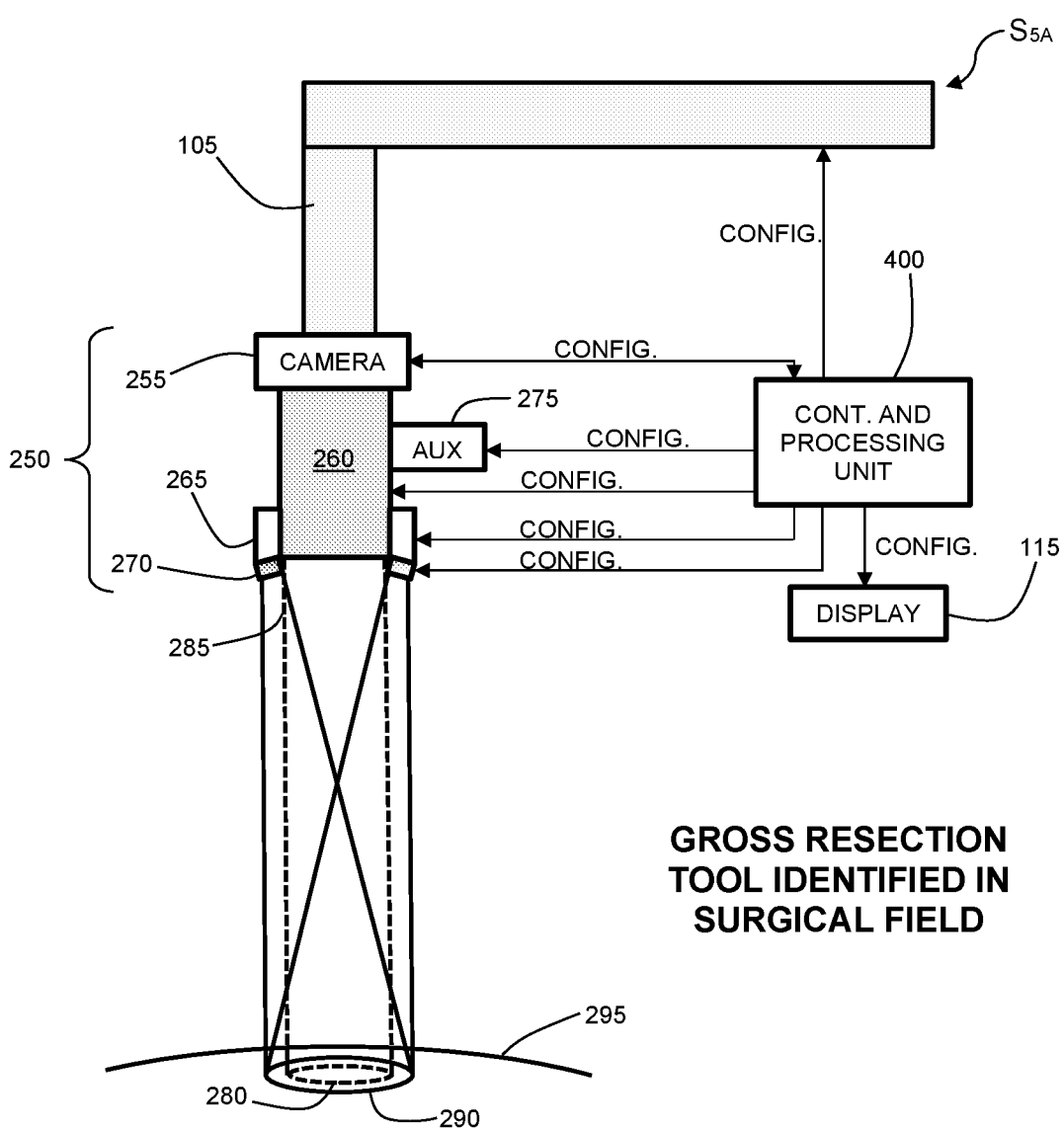
FIG. 5A is a diagram illustrating a surgical system, comprising an optical imaging system and associated control system, wherein at least one component of the optical system is adaptively reconfigurable, based on the identification of a medical instrument.

Referring to FIG. 5A, this diagram illustrates a surgical system $S_{5A}$, comprising an optical imaging system and an associated control system, wherein one or more components of the optical system 250 are adaptively reconfigurable, based on the identification of a medical instrument, in accordance with some embodiments of the present disclosure. In an example, the devices for which configuration parameters are provided comprise an illumination device and/or an optical imaging device. For example, a surgical system comprises the optical imaging system and an associated control system. A subset of the components of a surgical system are shown, but some components, e.g., a tracking system, are not shown in order to simplify the illustration. The system $S_{5A}$ comprises an optical system 250, the optical system 250 comprising: a camera 255, imaging optics assembly 260, illuminators 265, illumination focusing optics 270, and auxiliary imaging modality assembly 275. An image detected by the camera 255 is displayable on a display 115 (FIG. 1). The optical system 250 is supported by a robotic arm 105. The imaging optics assembly 260 is configured to image with a field of view 280, while illuminators 265 and illuminator focusing optics 270 project illumination beams 285 to form illumination region 290 on a tissue surface 295.

Still referring to FIG. 5A, with regard to illuminators 265, a wide variety of illuminator types are employed to provide intraoperative illumination. Examples of different types of illumination include a monochromatic or narrow band light source or laser source, a broadband source, such as a white light source, optionally having a spectrally selective element, such as an optical filter, a projector type source (which may optionally be employed for surgical guidance or for projecting customized light patterns onto the surgical field), a polarized light source implemented by polarizing filters, structured light projectors, photo-acoustic excitation lasers, ablation lasers, and therapeutic light sources used for photo-activation of therapeutic solutions. Illumination light is locally generated, or optionally externally generated, and directed to optical system 250 by using an optical conduit, such as a fiber optic bundle, a light pipe, or free space delivery. The illumination may be broad to fill the entire surgical field of view, e.g., at the end of an access port, or focused on a particular point. Each of these light delivery devices can be controlled by the control and processing unit 400.

Still referring to FIG. 5A, the control and processing unit 400 is interfaced with one or more components of optical system 250 in order to dynamically provide configuration parameters, based on the intraoperative identification of one or more medical instruments. The control and processing unit 400 is interfaced with camera 255, imaging optics assembly 260, illuminators 265, illumination focusing optics 270, and auxiliary imaging modality assembly 275. Upon detection of a medical instrument, the configuration data is accessed in order to determine customized configuration parameters for one or more components of the optical system; and the customized configuration parameters are employed to configure or reconfigure the one or more components. For example, a coarse resection tool (not shown) is identified; and customized configuration parameters are obtained for customizing one or more of camera 255, imaging optics assembly 260, illuminators 265, illumination focusing optics 270, auxiliary imaging modality assembly 275, robotic arm 105, and a user interface displayed on display 115, based on the identification of the coarse resection tool.

Still referring to FIG. 5A, the optical system 250 comprises a primary optical imaging modality that is provided by the camera 255, but the optical system 250 further comprises an auxiliary imaging modality assembly 275. As noted above, the auxiliary imaging modality assembly 275 comprises one or more optical ports, and a mechanism, such as an optical deflection device, e.g., a mirror, prism, reflector, filter, pellicle, window, or optical pick-off, that is selectively actuated to deflect the beam path along the port axis, thereby directing the optical beam to imaging and/or source optics associated with another imaging modality. For example, an auxiliary imaging modality assembly 275 comprises one or more ports for selectively employing an additional imaging modality, including, but not limited to, fluorescence imaging, hyperspectral imaging, optical coherence tomography, polarization-sensitive optical coherence tomography, polarization-sensitive imaging, and Raman imaging. The control and processing unit 400 provides one or more configuration parameters for selectively configuring the imaging system to employ one or more additional or alternative imaging modalities. The control and processing unit 400 further provides one or more configuration parameters for selectively configuring the one or more additional or alternative imaging devices that employ other imaging modalities.

Figure 5B:
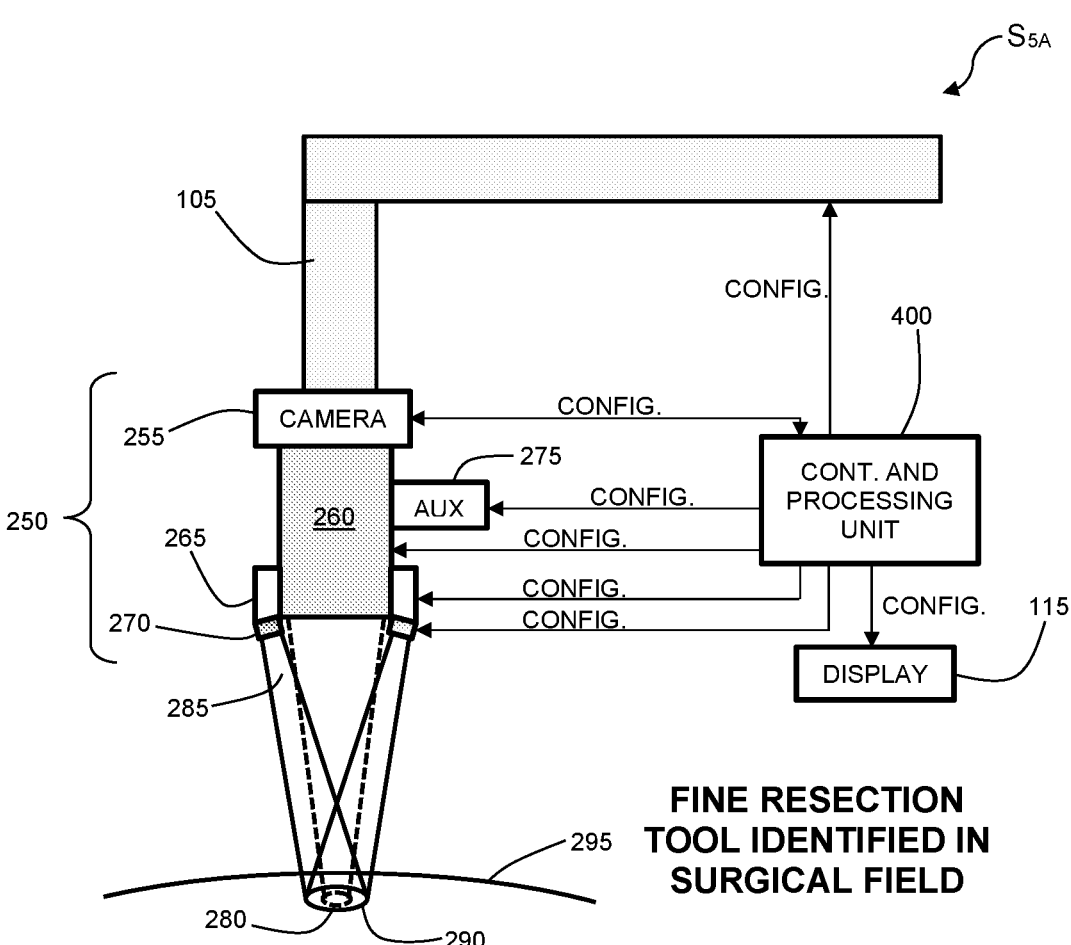
FIG. 5B is a diagram illustrating a surgical system, similar to the surgical system, as shown in FIG. 5A, reconfigured after identification of a different medical instrument within the surgical field.

Referring to FIG. 5B, this diagram illustrates a surgical system $S_{5B}$, similar to the system $S_{5A}$, as shown in FIG. 5A, reconfigured after identification of a different medical instrument within the surgical field, in accordance with an embodiment of the present disclosure. When the coarse resection tool is removed from the surgical field and a fine resection tool is brought within the surgical field, the absence of the gross section tool and the presence of the fine resection tool is detected, with the fine resection tool being identified by the surgical system $S_{5B}$ as above described. New customized configuration parameters are obtained; and the optical system 250 is reconfigured. In the example shown, configuration parameters for a number of components are modified due to the identification of the fine resection device. Specifically, the robotic arm 105 is repositioned according to updated configuration parameters to achieve a reduced working distance. The imaging optics assembly is reconfigured to provide a reduced field of view 280, and, therefore, has a higher magnification. The illumination focusing optics 270 are reconfigured to produce a reduced illumination region; and the illuminators 265 are reduced in intensity in order to preserve the intensity of illumination within the illumination region 290.

Still referring FIG. 5B, for example, the system is further reconfigured by providing configuration parameters for any one of more of room lights, e.g., dimming or increasing brightness, coarse resection tool reconfiguration, fine resection tool reconfiguration, adjustment of speed and/or power of the fine resection tool, modifying hanging protocols displayed on the navigation screen, e.g., display different sets of images and different views of those images, and adjust the angle or height of the surgical table. In one embodiment, fine resection tool is tracked by tracking system 120, and the customized configuration parameters configure robotic arm 105 to be actuated such that the field of view 280 of imaging optics assembly 260 is actively translated to overlap with the distal tip of the fine resection device based on closed-loop feedback from tracking system 120.

Referring to FIG. 5C, this table illustrates configuration data associating configuration parameters for a camera with the identity of various medical instruments, in accordance with an embodiment of the present disclosure. In one example implementation, the control and processing unit 400 is interfaced with camera 255 in order to adaptively provide configuration parameters associated with one or more of, but not limited to, imaging frame rate, gain, saturation, shutter speed, ISO, aperture size, on-chip binning, image size, digital zoom (ROI), and cooling temperature, e.g., if thermo-electric cooling is available. An example of configuration data that associates configuration parameters for camera 255 with one or more medical instruments is shown.

Referring to FIG. 5D, this table illustrates configuration data associating configuration parameters for an imaging optics assembly with the identity of various medical instruments, in accordance with an embodiment of the present disclosure. The control and processing unit 400 is additionally, or alternatively, interfaced with imaging optics assembly 260 in order to provide configuration parameters associated with one or more of, but not limited to, zoom (magnification), focal length, working distance, numerical aperture, polarization sensitivity, attenuation, filter wavelength, depth of field, image stabilization, and field of view. For example, the imaging optics assembly 260 comprises one or more actuators for varying these settings according to the configuration parameters that are provided. An example of configuration data that associates configuration parameters for imaging optics assembly 260 with one or more medical instruments is shown.

Referring to FIG. 5E, this table illustrates configuration data associating configuration parameters for an illuminator with the identity of various medical instruments, in accordance with an embodiment of the present disclosure. Control and processing unit 400 is additionally, or alternatively, interfaced with illuminators 265 in order to provide configuration parameters associated with one or more of, but not limited to, illumination intensity, illumination wavelength, illumination angle, pulsed or continuous operation, and number of active illuminators. For example, illuminators 265 comprises one or more actuators for varying the incidence angle of the illumination beams according to the configuration parameters that are provided. An example of configuration data that associates configuration parameters for illuminators 265 with one or more medical instruments is shown.

Referring to FIG. 5F, this table illustrates configuration data associating configuration parameters for illuminator focusing optics with the identity of various medical instruments, in accordance with an embodiment of the present disclosure. Control and processing unit 400 is additionally, or alternatively, interfaced with illumination focusing optics 270 in order to provide configuration parameters associated with one or more of, but not limited to, focal length, depth of field, illumination spot size, beam shape, working distance, polarization, filter wavelength, and attenuation. For example, illumination focusing optics 270 comprise one or more actuators for varying these settings according to the configuration parameters that are provided. An example of configuration data that associates configuration parameters for illumination focusing optics 270 with one or more medical instruments is shown.

Referring back to FIGS. 5A-5F, the control and processing unit 400 is additionally, or alternatively, interfaced with an auxiliary imaging modality assembly 275. For example, the auxiliary imaging modality assembly 275 comprises one or more optical ports and a mechanism, such as an optical deflection device, e.g., a mirror, prism, reflector, filter, pellicle, window, or optical pick-off, that may be selectively actuated to deflect the beam path along the port axis, thereby directing the optical beam to imaging and/or source optics associated with another imaging modality. For example, in one example implementation, the auxiliary imaging modality assembly 275 comprises one or more ports for selectively employing an additional imaging modality including, but not limited to, fluorescence imaging, infrared imaging, ultraviolet imaging, hyperspectral imaging, optical coherence tomography, polarization-sensitive optical coherence tomography, polarization-sensitive imaging, thermal imaging, photo-acoustic imaging, and Raman imaging. The control and processing unit 400, thus, provides one or more configuration parameters for selectively configuring the imaging system to employ one or more additional or alternative imaging modalities. The control and processing unit 400 also provides one or more configuration parameters for selectively configuring the one or more additional, or alternative, imaging modalities.

Still referring back to FIGS. 5A-5F, in some embodiments, one or more external imaging devices may be employed for multi-modal imaging. For example, multi-modal imaging is achieved by way of either direct optical imaging, or using the system to hold additional imaging probes, such as MRI, US, PET or X-ray (either in transmit or receive modes). In some embodiments, the turret of robotic arm 105 is actuated during the procedure to engage different modalities, as described above, much in the way multiple tools are selected in a CNC machining system. In other embodiments, multiple modalities, other than optical, e.g., ultrasound, MRI, OCT, PET, and CT, are supported by, or otherwise interfaced with, the automated arm, optionally in addition to one or more optical imaging/detection modalities.

Still referring back to FIGS. 5A-5F, in the case of photo-acoustic imaging, laser light is used to excite the tissue, while an ultrasound array positioned in the access port is employed to collect the emitted ultrasound signal. In addition, different wavelengths or spectral bands of light are utilized. For instance, Raman imaging can be used to investigate the chemical composition of tissue at a specific location of interest, e.g., point source imaging. Hyperspectral imaging is accomplished by scanning a detector across the region of interest or by collecting multi-spectral detector images at a selected location. In one example implementation, the hyperspectral image is overlaid on video images to provide different perspectives of exposed tissue regions. In another example embodiment, laser light, delivered by an optical device supported by the automated arm, is employed for the alignment and/or excitation of photo-reactive therapeutics. Any or all of the optical imaging modes, employed by a given system embodiment, may be accommodated by a fiber-optic delivery and receiving bundle that is attached to the turret of the robotic arm 105. Alternatively, or additionally, various ports or light guides are used to co-align the light delivery or reception.

Still referring back to FIGS. 5A-5F, in an alternative embodiment, optical system 250 has different acquisition modes. Some modes are listed as follows, but are not limited to additional modes not listed here. In one mode, images are acquired by sweeping through the different image acquisition modes to provide multiple serially obtained, e.g., almost simultaneously obtained, images of different types which are combined into an overlaid representation and displayed to the operator. The multi modal shifting is achieved, for example, by using a filter wheel on the optical system, thereby allowing the imaging modalities to change as the wheel is turned. The multi modal shifting is also achieved through beam splitting using optical lenses and directing the beams to different imaging devices. Although several different components are shown interfaced with control and processing unit 400, the control and processing unit 400 may be interfaced with any component, or any combination of components, and with other components that are not shown.

Still referring back to FIGS. 5A-5F, in an alternate embodiment, the optical system 250, under control of control and processing system 400, may automatically perform actions such as, but not limited to, autofocus of the optical view and auto adjustment of the illumination system for optimal viewing illumination, optimal tissue differentiation, and optimal modal detection. The optical system 250 can achieve these automatic functions through analysis of the various images acquired by the system, such as the optical camera image or others by control and processing system 400. The images can be analyzed for metrics such as white balance, contrast, and saturation. The metrics are then processed based on the type of view required, for example when illuminating for tissue differentiation the imaging processing method should employ the constraints of the system (geometric, intensity range, etc.) to obtain the illumination intensity and wavelengths which would provide a suitable, e.g., maximal, contrast metric. Other image analysis that could be done include image sharpness determination and optimization by analyzing specific focal zones.

Still referring back to FIGS. 5A-5F, alternatively, the optical system 250 could adjust zoom and focus by calculating the working distance between the camera 255 and the surgical area of interest by using position and orientation of the surgical tool and position and orientation of the optical system provided by the navigation system. In the case of port-based surgery, the port could be tracked and the zoom and focus be set based on the working distance between the camera and bottom of the port. In both of these cases, a lookup table could be created that relates working distance to a set of camera parameters: zoom, focus, aperture, and iris. This relationship could be determined empirically or analytically. The preceding examples illustrate embodiments in which configuration parameters are provided in a number of data structures pertaining to different devices that may be intraoperatively configured based on the identification of one or more medical instruments. The data structures were illustrated separately for heuristic purposes. In other implementations, the two or more data structures are combined. For example, a composite data structure is formed in which different devices are provided as different columns.

Referring back to FIGS. 5C-5F, configuration parameters may be provided for intraoperatively configuring a device based on the identification of a single medical instrument, or based on the identification of multiple medical instruments. The example data structures illustrate an example implementation in which configuration parameters are provided for each relevant combination of identified medical devices.

Referring to FIG. 5G, this table illustrates configuration data associating configuration parameters for a camera with a ranked list of medical instruments, in accordance with an embodiment of the present disclosure. In another example implementation, configuration parameters can be provided for multiple identified medical instruments according to a ranked or prioritized list of medical instruments. For example, an implementation of a data structure is provided in which configuration parameters are provided for camera 255 on a unique basis for each medical instrument that may be identified. The control and processing unit 400 may be programmed to interpret the data structure in a ranked configuration. If a single medical instrument is identified, in the absence of other medical instruments, then the configuration parameter set associated with the single medical instrument is employed to configure camera 255. For example, if only instrument 4 is identified at any given time during a medical procedure, in the absence of instruments 1, 2, 3, 5, and 6, then configuration parameter set 4 is employed to configure camera 255.

Still referring to FIG. 5G, however, if two or more medical instruments are intraoperatively identified, then configuration parameters associated with the highest ranked medical instrument are employed. For example, if medical instruments 3 and 5 are identified at a given time during a medical procedure, the configuration parameters used to configure camera 255 would be configuration parameter set 3, since medical instrument 3 outranks medical instrument 5. The specific implementation is merely one example implementation, and variants of this embodiment may be performed without departing from the scope of the present disclosure. For example, weighting factors or coefficients may be employed to realize a related ranked or prioritized embodiment.

Referring to FIG. 5H, this table illustrates configuration data associating configuration parameters for a camera with the identity of various medical instruments, including configuration parameters associated with the absence of a detected medical instrument, in accordance with an embodiment of the present disclosure. Although the preceding example implementations illustrate cases in which configuration parameters are provided based on the identification of one or more medical instruments, the configuration data may include a default set of configuration parameters that may be employed to configure the device when the identifiable medical instruments are not present. For example, this may be useful for ensuring that a given device reverts to a default configuration when one or more identified medical instruments are removed from the surgical field or region of interest.

Referring back to FIGS. 5C-5H, the example embodiments relate the identification of a medical instrument by its name or type, e.g., by its clinical, medical, or conventional name, with customized configuration parameters for adaptively and intraoperatively configuring a device, e.g., camera 255. The identification of an instrument by name or type is but one example implementation of an identification method; and many other methods may be employed to identify a medical instrument. For example, a medical instrument is indirectly identified with a textual, numeric, symbolic, or alphanumeric instrument identifier that is associated with its identity. In such an embodiment, configuration data comprises data elements associating one or more instrument identifiers with customized configuration parameters, wherein the instrument identifier is initially obtained from the pre-selected identification data, as above described.

Still referring back to FIGS. 5C-5H, in some embodiments, the medical instrument is identified beyond its name or type. For example, in one embodiment, the instrument is uniquely identified. In other words, a resection device would not simply be identified as a generic "resection device," but the resection device would be identified with a unique identifier that is only associated with the specific instrument that is used, such as an instrument identifier comprising a serial or inventory number associated with the resection device.

Still referring back to FIGS. 5C-5H, in one example implementation, a medical instrument is identified as being associated with a specific operator. For example, a medical instrument is commonly associated with a specific surgeon; and the instrument identifier comprises identifying information associating the medical instrument with the specific surgeon. In such an embodiment, the configuration data correlates the instrument identifier with configuration parameters that are preferred by the specific surgeon, such that, when the specific medical instrument is used and identified, the control and processing unit 400 provides the preferred configuration parameters to the relevant medical device or devices. In one embodiment, biometric sensors identify the user of the device. The biometric sensors are integrated into the surgical tool or are acquired via a separate device that is either continuously attached to the surgeon or separate from the surgeon, e.g., the surgeon activates his/her identity at a computer console. Example biometric identification techniques comprise: iris scan, fingerprint scan, voice identification, and cardiac patterns.

Still referring back to FIGS. 5C-5H, in one example implementation, the configuration data that is used to associate the identity of one or more medical devices with customized configuration parameters (for the interoperative configuration of one or more devices) depend on the location of the automated system. For example, a given medical instrument is used in two different operating rooms, each room having a separate automated system, wherein the two operating rooms are employed for performing different medical procedures. In such a case, the configuration data employed by one automated system may be different than the configuration data employed by the other automated system, such that the same medical instrument is employed in either room, but wherein different configuration parameters are associated with the medical instrument in each room.

Referring to FIG. 5I, this table illustrates configuration data associating configuration parameters for a camera with the identity of various medical instruments, wherein the configuration parameters are further associated with the type of medical procedure being performed, in accordance with an embodiment of the present disclosure. In another example implementation, the configuration data that is used to associate the identity of one or more medical devices with customized configuration parameters is further associated with a medical procedure. An additional column is shown that further associates the configuration parameters with a given medical procedure. According to this example embodiment, upon identification of a medical instrument, the control and processing unit 400 selects the appropriate customized configuration parameters for intraoperatively configuring one or more devices based on both the identity of the medical instrument and the procedure that is being performed. The control and processing unit 400 obtains information identifying the procedure being performed, based on operator input, automated detection (below described in detail), or pre-programmed information.

Referring to FIG. 5J, this a table illustrates configuration data associating configuration parameters for a camera with the identity of various medical instruments, wherein the configuration parameters are further associated with the phase of the medical procedure, in accordance with an embodiment of the present disclosure. In another example implementation, the configuration data that is used to associate the identity of one or more medical devices with customized configuration parameters is further associated with a given step or a given phase of a medical procedure. An additional column is shown that further associates the configuration parameters with a given phase of a medical procedure. According to this example embodiment, upon identification of a medical instrument, the control and processing unit 400 selects the appropriate customized configuration parameters for intraoperatively configuring one or more devices based on both the identity of the medical instrument and the procedure that is being performed. The control and processing unit 400 obtains information identifying the phase of the procedure being performed based on operator input, automated detection (below described in detail), or pre-programmed information. The preceding example embodiments, pertaining to the configuration of devices, based on the identification of one or more medical instruments, are illustrated within the context of device components associated with an optical system.

Referring to FIG. 5K, this a table illustrates configuration data associating configuration parameters for a robotic arm with the identity of various medical instruments, in accordance with an embodiment of the present disclosure. In one another example implementation, the device for which configuration parameters are provided comprises a robotic arm that is employed to position one or more tools or devices. Examples of configuration parameters for configuring a robotic arm include, but not limited to, positions and orientations of the arm, motor speeds, safety regions for collision avoidance, stiffness, home positions, tip speeds, acceleration profiles, working distance offset, position of the arm with respect to the surgeon, updated voice command library if the robot is controlled via voice commands, updated mapping of robot control pedals/buttons, enable/disable of automatic tracking modes, thresholds used to trigger automatic movement/alignment of the robot, safety delay time, movement patterns, payload weight that will require the arm to compensate accordingly to the new weight, movement for various types of lighting, and surgical phase.

Still referring to FIG. 5K, in another example implementation, the device for which configuration parameters are provided comprises a computer-controlled user interface. For example, as shown in FIG. 5A, display 115 comprises a user interface, such as a user interface associated with the output from optical system 250 and/or navigation. One or more input devices are employed to allow an operator to interact with the user interface; and examples are below provided. The configuration parameters that are associated with the one or more medical instruments may enable the automated re-configuration of the user interface based on the identification of one or more medical instruments. Examples of configuration parameters for configuring a user interface include, but not limited to, displayed windows, displayed icons, colors, one or more displayed or displayable menu items, intensity of one or more displayed items, relative size of displayed windows, relative positioning of one or more windows, display of images from one or more imaging modalities, selection of imaging modalities for overlay of images from two or more imaging modalities, and messages or warnings for the operator, selection of which tracked tool is used to control the view of imaging data, background music selection, default display options, e.g., are augmented graphics displayed, user interface skin/theme, mapping of control buttons, various data display or analysis options related to particular imaging modalities, and alerts corresponding to identification of particular spectral information related to identification of potential unhealthy tissues.

Figure 6A:
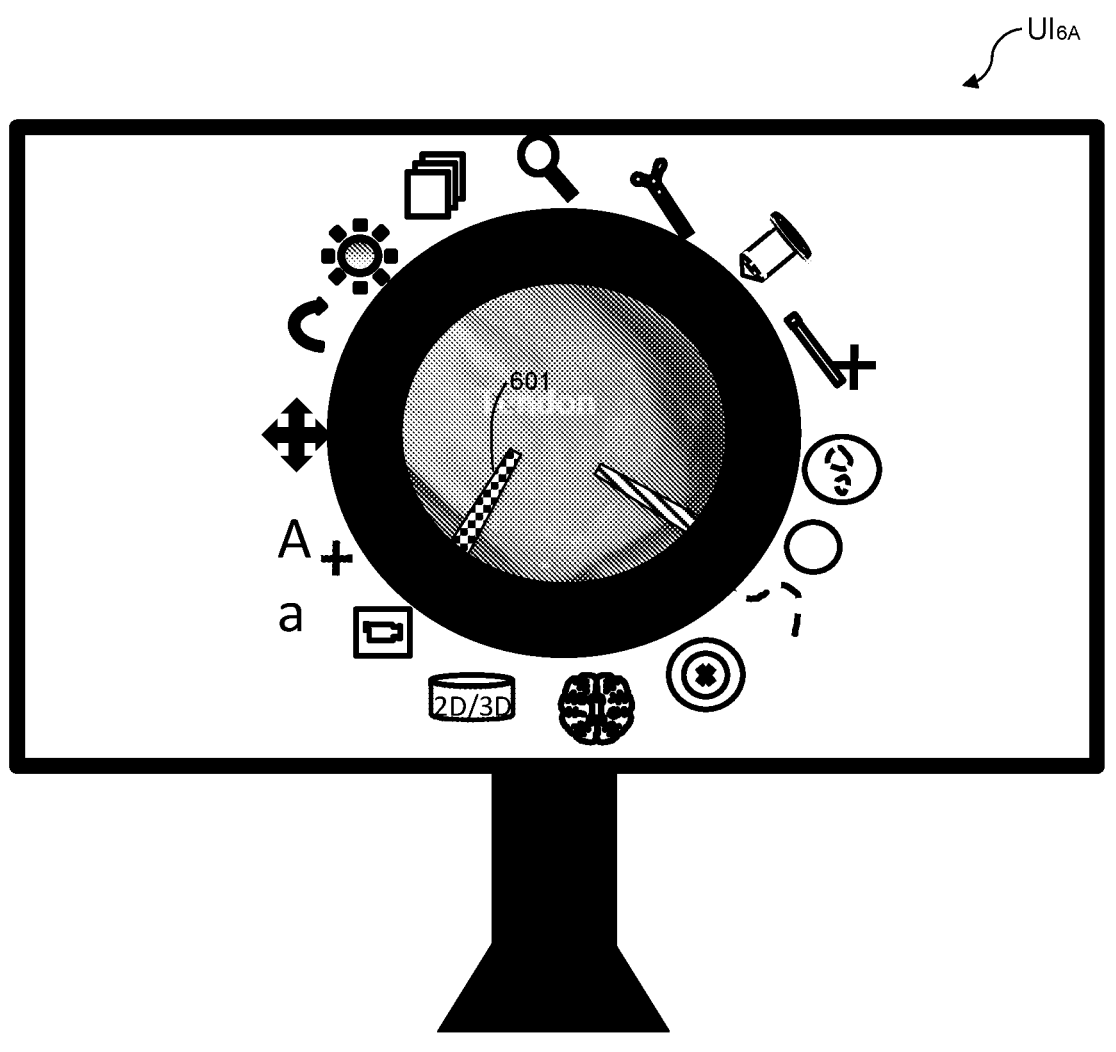
FIG. 6A is a diagram illustrating a user interface prior to the identification of a medical instrument.
Figure 6B:
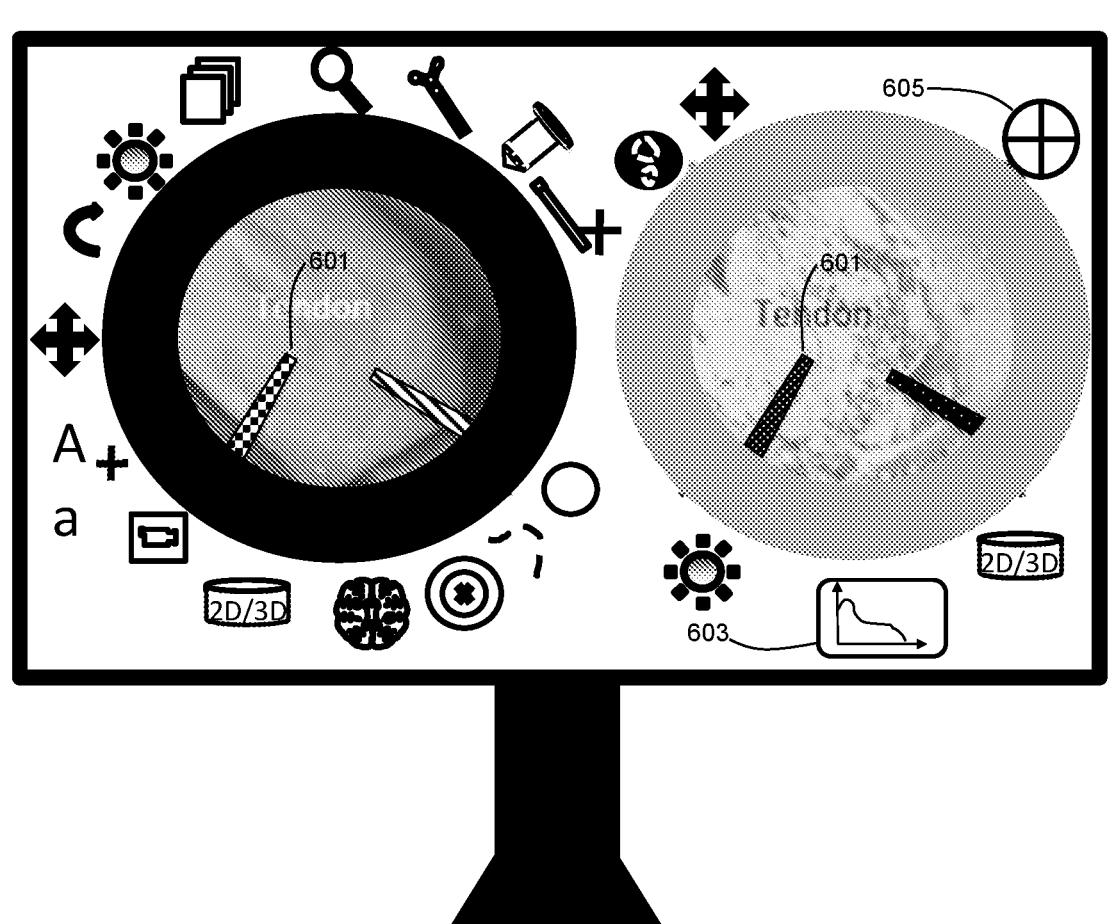
FIG. 6B is a diagram illustrating a user interface, comprising the user interface, as shown in FIG. 6A, being reconfigured after the identification of a medical instrument.

Referring to FIGS. 6A and 6B, together, these diagrams illustrate an example implementation of a user interface that is automatically configurable based on the identification of one or more medical instruments, in accordance with embodiments of the present disclosure. Referring to FIG. 6A, this diagram illustrates a user interface $UI_{6A}$ prior to the identification of a medical instrument, in accordance with an embodiment of the present disclosure. The user interface is shown prior to detection of the medical instrument, e.g., a fine resection tool 601. Referring to FIG. 6B this diagram illustrates a user interface $UI_{6B}$, comprising the user interface $UI_{6A}$, as shown in FIG. 6A, being reconfigured after the identification of a medical instrument, in accordance with an embodiment of the present disclosure. The user interface is shown after the detection of the medical instrument, e.g., the fine resection tool 601. In the latter case, the control and processing unit 400, having identified the medical instrument, has determined, based on the configuration data, configuration parameters for reconfiguring the user interface. After the identification of the medical instrument, e.g., the fine resection tool 601, the system has switched to a hyperspectral mode for providing images for better tissue differentiation. Accordingly, the GUI has adapted to this multimodal imaging by simultaneously displaying both the visible imaging and the hyperspectral imaging side by side as opposed to just the single view, as shown in FIG. 6A. The adapted GUI also provides additional control buttons specific to this multimodal display with hyperspectral imaging. For example, a button 603 allows the user to view a hyperspectral spectrum at a specific point on the display of the hyperspectral image if the user chose to do so. Another example is an alert 605 which changes colour if a particular spectral fingerprint is identified in the hyperspectral image which is related to an unhealthy tissue type, for example, a tumor tissue spectral fingerprint.

Still referring to FIGS. 6A and 6B, together, customized configuration parameters may be pre-selected prior to the commencement of the medical procedure, or may, alternatively, be provided, or modified, during the medical procedure. For example, a user interface is provided to facilitate input or modification of configuration data and/or identification data via a suitable input device. Examples of input devices are below described. The user interface may also be provided to optionally override one or more configuration parameters.

Figure 7A:
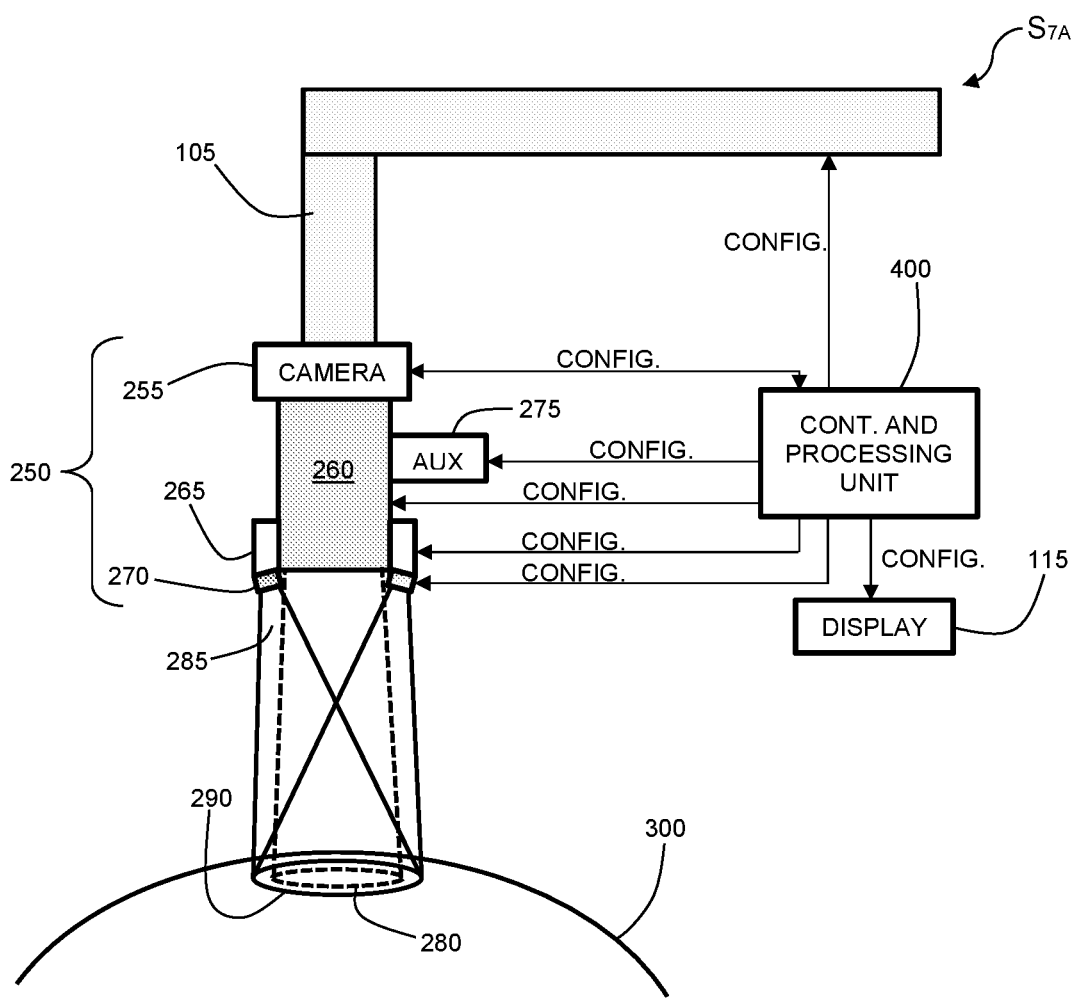
FIG. 7A is a diagram illustrating a surgical system, comprising an optical system, having a configuration prior to identification of an access port, wherein the configuration is intraoperatively changeable by using at least one new configuration parameter when the access port is identified.
Figure 7B:
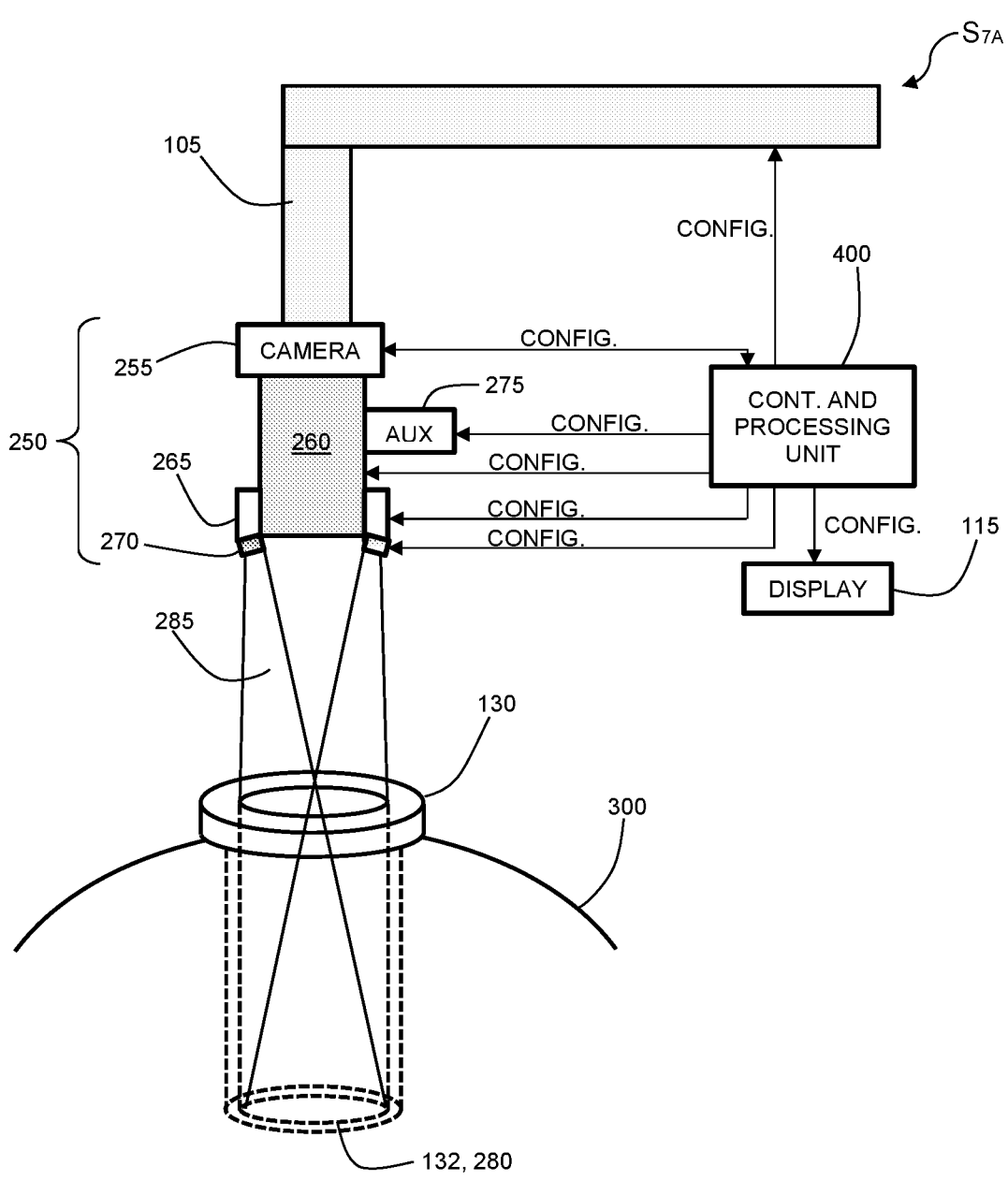
FIG. 7B is a diagram illustrating a surgical system, comprising an optical system, as shown in FIG. 7A, having a new configuration after identification of the access port, wherein the configuration is intraoperatively changed by using the at least one new configuration parameter when the access port is identified.

Referring to FIGS. 7A and 7B, together, these diagrams illustrate an example embodiment in which the control and processing unit 400 is employed to provide new configuration parameters for intraoperatively changing the configuration of the optical system 250 when an access port is identified, in accordance with embodiments of the present disclosure. Referring to FIG. 7A, this diagram illustrates a surgical system $S_{7A}$, e.g., comprising the optical system 250, having a configuration prior to identification of an access port, wherein the configuration is intraoperatively changeable by using at least one new configuration parameter when the access port is identified, in accordance with an embodiment of the present disclosure. The optical assembly 250 is shown in a configuration to image the top portion of a patient's skull 300. This initial configuration is determined, based on configuration parameters obtained, in turn, based on the identification of one or more medical instruments employed for performing a craniotomy (not shown), such as a craniotomy drill used specifically for removing a section of the skull for surgical access to the brain or a scalpel used to access the skull through the skin.

Still referring to FIG. 7A, for example, configuration parameters are provided that stipulate the diameter of illumination spot 290 and the field of view 280 provided by the imaging optics assembly 260. Additional configuration parameters are provided to specify a pre-selected working distance between the distal portion of the imaging optics assembly 260 and the surface of the skull 300; and these additional configuration parameters are employed to move the robotic arm 105 to a suitable position for performing the craniotomy while imaging. In such cases, both the optical system 250 and the patient's skull 300 are spatially referenced to enable the relative positioning of the optical system 250. Further examples of configuration parameters that are obtained, based on the identification of the medical instruments, include configuration parameters that specify a suitable illumination intensity, spectral profile, colour, or wavelength. As above noted, the identification of the medical instruments for performing the craniotomy is also employed to reconfigure the user interface displayed on the display 115.

Referring to FIG. 7B, this diagram illustrates a surgical system $S_{7B}$, e.g., comprising an optical system 250, as shown in FIG. 7A, having a new configuration after identification of the access port, wherein the configuration is intraoperatively changed by using the at least one new configuration parameter when the access port is identified, in accordance with an embodiment of the present disclosure. In the example neurological procedure presently considered, a surgical access port is inserted into the brain after having performed the craniotomy, as above described. An access port 130 is inserted into the patient's head, wherein a distal internal surface 132 of the access port 130 (or the distal aperture of the access port, depending on the type of access port that is used) is recessed deep within the brain, thereby providing surgical, diagnostic, and/or therapeutic access to brain internal tissue. The control and processing unit 400 identifies the access port 130, which is automatically performed, for example, based on fiducial markers or on other identifying indicia attached to the access port 130, via image processing of an image of the surgical field, or via input from an operator indicating that the access port 130 has been employed.

Still referring to FIG. 7B, the configuration data is then processed to obtain configuration parameters that are customized, based on the presence of the access port 130 within the surgical field; and the customized configuration parameters are employed to re-configure one or more components of the optical system 250. For example, the angle and/or angular width of illumination beams 285 are modified such that the distal inner surface or aperture 132 of access port 130 is illuminated, and the working distance and field of view of imaging optics assembly 260 are modified for imaging of the distal surface or aperture 132 of access port 130. Further examples of configuration parameters that may be obtained, based on the identification of the medical instruments, include configuration parameters that specify a suitable illumination intensity, spectral profile, colour, or wavelength for performing one or more port-based procedures. The identification of access port 130 may also be employed to reconfigure the user interface displayed on display 115. The configuration of the optical system is further modified by the introduction into the surgical field of one or more medical instruments having customized configuration parameters therewith associated.

Still referring to FIG. 7B, in some embodiments, the customized configuration parameters associated with the presence of access port 130 are employed to provide the delivery of homogenized light through the port to the surgical area of interest, thereby potentially permitting improved tissue differentiation between healthy brain tissue and unhealthy brain tissue by potentially reducing glare and reducing shadows which fall on the tissue due to ports. For example, the configuration parameters are provided on a continuous basis while the access port 130 is detected within the surgical field to actively control the position of the robotic arm 105 such that coaxial alignment between the axis of the imaging optics assembly 260 and the access port 130 is maintained. These configuration parameters are dynamically computed by the control and processing unit 400, based on real-time tracking of the orientation of the access port 130 via the tracking system 120.

Still referring to FIG. 7B, in one example embodiment, the configuration parameters associated with the orientation of optical system 250 are computed in order to achieve a desired level of homogeneity of illumination intensity for illumination within the access port 130. For example, optical modelling, such as non-sequential ray-tracing, is employed to calculate, for a given set of optical focusing conditions, a working distance for the illuminators that provides a suitable, or optimal, level of illumination homogeneity. The modelling comprises the angular intensity distribution of the source and the optical properties of the access port 130, such that reflections from the port walls are modelled.

Figure 7C:
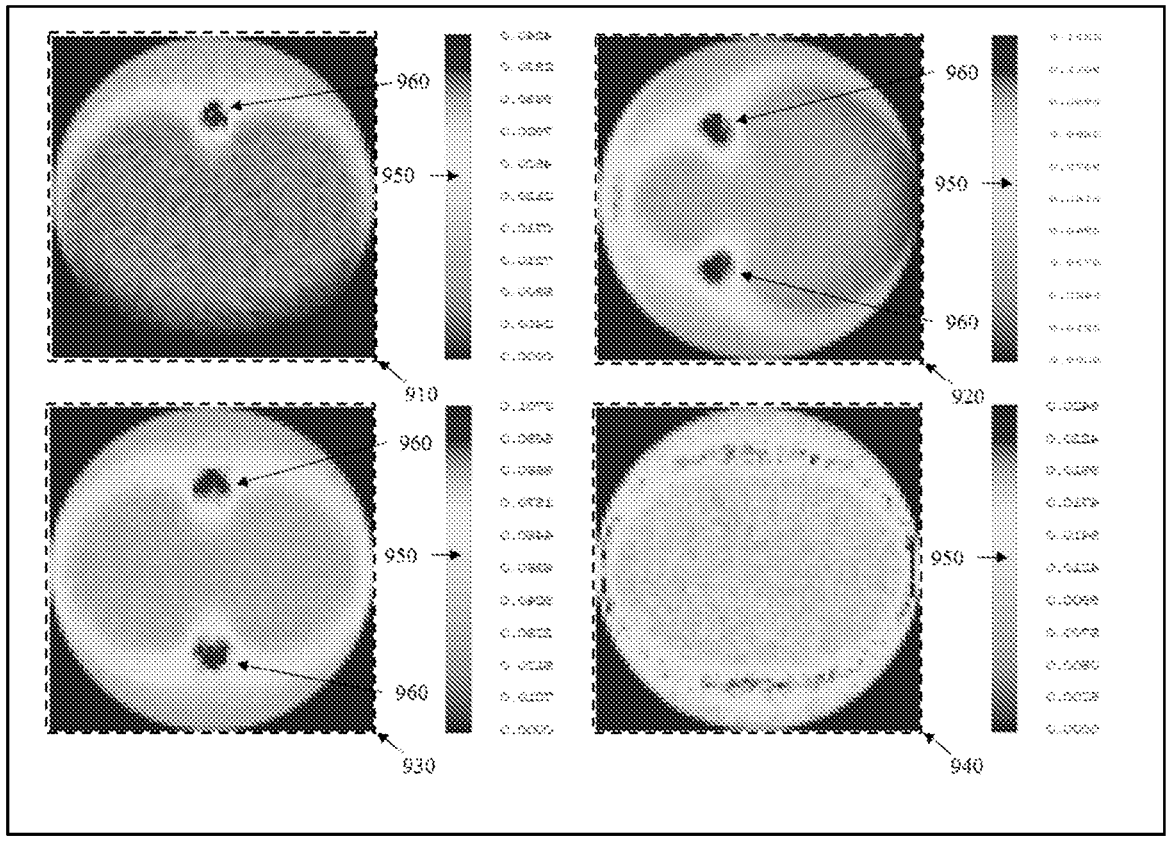
FIG. 7C is a diagram illustrating images relating to an implementation for the use of ray tracing to calculate a configuration parameter, specifying the working distance of the illuminators in order to achieve a pre-selected level of illumination homogeneity.

Referring to FIG. 7C, this diagram illustrates images relating to an implementation for the use of ray tracing to calculate a configuration parameter, specifying the working distance of the illuminators in order to achieve a pre-selected level of illumination homogeneity, in accordance with an embodiment of the present disclosure. Non-sequential ray tracing software (ZEMAX®) is employed to model the illumination intensity distribution at the distal surface 132 within the access port 130, based on the optical properties of the access port 130 as well as the properties of the illuminators 265.

Still referring to FIG. 7C, illumination intensity distributions are computed, based on four different models, each having a different illuminator configuration. The first model 910 shows the illumination of the region of interest at the distal end of the access port 130 by using a single illuminator at a distance of 35 cm from the bottom of the access port 130 and an offset 16.5 mm from the central axis of the access port 130. The second model 920 and the third model 930 show illumination of the region of interest by respectively using illumination from two illuminators. The pairs of sources in each model are oriented differently with respect to the other model. Both the second model and the third model have the same distance and pose parameters as the first model relative to the port, e.g., a 35-cm distance from the bottom of the port and each illuminator offset by 16.5 mm from the central axis of the access port 130.

Still referring to FIG. 7C, the final model 940 shows illumination from two sources with the same orientation as the sources in the second model 920 relative to the external imaging sensor with the same pose, but with a working distance of 65 cm. The intensity map on each region of interest (distal end of the port) illustrates the illumination level, wherein a mid-range 950 represents the ideal illumination level. Hot spots 960 exist in the first model 910, the second model 920, and the third model 930 which result in heavy glare at those positions and inadequate imaging for the surgeon, while the fourth model 940 provides the optimal lighting condition (homogenized and low glare delivery of illumination). Using the fourth model 940 as the optimal pose alignment, the automated mechanical arm would position the scope to achieve this particular illumination, thereby improving the operating view of the surgeon. The software can then determine a suitable spatial position and a suitable pose of the illumination source relative to the target, e.g., the access port, given the restrictions of the system to ensure optimal light delivery through the port to the region of interest. The illumination source is further optimally positioned after modelling the shadow cast by the surgical tools. In other words, the target region within the field of view is optimally illuminated while avoiding casting of shadows from the surgical tools. This circumstance is possible given that the three-dimensional pose of the surgical tools can be estimated by using fiducial tracking markers placed on the surgical tools.

Figure 8:
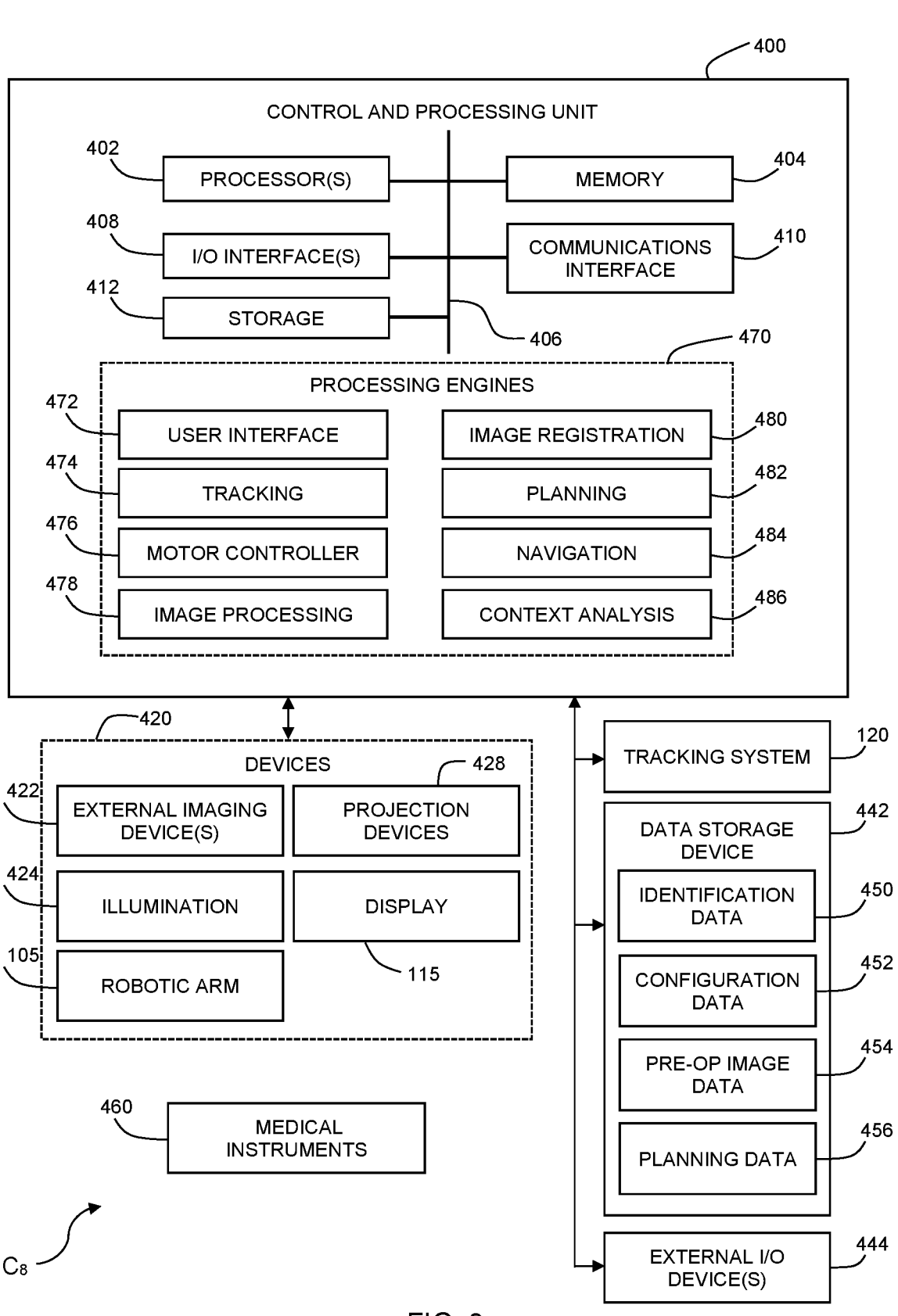
FIG. 8 is a block diagram illustrating a system configuration, comprising a control and processing unit and a number of external components.

Referring FIG. 8, this block diagram illustrates a system configuration C₈, comprising a control and processing unit 400 and a number of external components, in accordance with an embodiment of the present disclosure. The control and processing unit 400 comprises: one or more processors 402, a memory 404, a system bus 406, one or more input/output interfaces 408, a communications interface 410, and a storage device 412. The control and processing unit 400 is interfaced with other external devices, such as the tracking system 120, the data storage 442, and external user input and output devices 444, comprising, for example, one or more of a display, a keyboard, a mouse, a foot pedal, a microphone, and a speaker. The data storage 442 comprises any suitable data storage device, such as a local computing device or remote computing device, e.g., a computer, hard drive, digital media device, or server, having a database thereon stored. The data storage device 442 comprises identification data 450 for identifying one or more medical instruments 460 and configuration data 452 that associates customized configuration parameters with one or more medical instruments 460. The data storage device 442 further comprises at least one of preoperative image data 454 and medical procedure planning data 456. Although the data storage device 442 is shown as a single device, in other embodiments, the data storage device 442 comprises a plurality of storage devices.

Still referring FIG. 8, the medical instruments 460 are identifiable by the control and processing unit 400. The medical instruments 460 are connected to, and controlled by, the control and processing unit 400, or operated, or otherwise employed, independent of the control and processing unit 400. The tracking system 120 is employed to track one or more of the medical instruments and to spatially register the one or more tracked medical instruments to an intraoperative reference frame. The control and processing unit 400 is further interfaced with a number of configurable devices and further intraoperatively reconfigures one or more of such devices, based on configuration parameters that are obtained from configuration data 452. Examples of the devices 420 include one or more external imaging device 422, one or more illumination devices 424, a robotic arm 105, one or more projection devices 428, and one or more displays 115.

Still referring FIG. 8, embodiments of the present disclosure are implemented via the processor(s) 402 and/or the memory 404. For example, the functionalities described herein can be partially implemented via hardware logic in the processor 402 and partially implemented by using the instructions stored in the memory 404 as one or more processing engines 470. Example processing engines include, but are not limited to, a user interface engine 472, a tracking engine 474, a motor controller 476, an image processing engine 478, an image registration engine 480, a procedure planning engine 482, navigation engine 484, and a context analysis module 486. The system is not intended to be limited to the components shown. One or more components of the control and processing 400 may be provided as an external component or device. In one alternative embodiment, the navigation module 484 may be provided as an external navigation system that is integrated with the control and processing unit 400.

Still referring FIG. 8, some embodiments may be implemented by using the processor 402 without additional instructions stored in the memory 404. Some embodiments may be implemented by using the instructions stored in the memory 404 for execution by one or more general purpose microprocessors. Thus, embodiments of the present disclosure are not limited to a specific configuration of hardware and/or software. While some embodiments are implemented in fully functioning computers and computer systems, various embodiments are capable of being distributed as a computing product in a variety of forms and are capable of being applied, regardless of the particular type of machine or computer readable media used to actually effect the distribution.

Still referring FIG. 8, at least some aspects disclosed can be embodied, at least in part, in software. That is, the techniques may be carried out in a computer system or other data processing system in response to its processor, such as a microprocessor, executing sequences of instructions contained in a memory, such as a ROM, a volatile RAM, a non-volatile memory, a cache, or a remote storage device. A computer readable storage medium can be used to store software and data which when executed by a data processing system causes the system to perform various methods. The executable software and data may be stored in various places including, for example, a ROM, a volatile RAM, a nonvolatile memory, and/or a cache. Portions of this software and/or data may be stored in any one of these storage devices.

Still referring FIG. 8, the preceding example embodiments involve systems and methods in which a device is intraoperatively configured, based on the identification of a medical instrument. In other example embodiments, one or more devices may be automatically controlled and/or configured by determining one or more context measures associated with a medical procedure. A "context measure", as used herein, refers to an identifier, data element, parameter, or other form of information that pertains to the current state of a medical procedure. In one example, a context measure may describe, identify, or be associated with, the current phase or step of the medical procedure. In another example, a context measure may identity the medical procedure, or the type of medical procedure, that is being performed. In another example, a context measure may identify the presence of a tissue type during a medical procedure. In another example, a context measure may identify the presence of one or more fluids, such as biological fluids or non-biological fluids, e.g., wash fluids, during the medical procedure, and may further identify the type of fluid. Each of these examples relate to the image-based identification of information pertaining to the context of the medical procedure.

Figure 9:
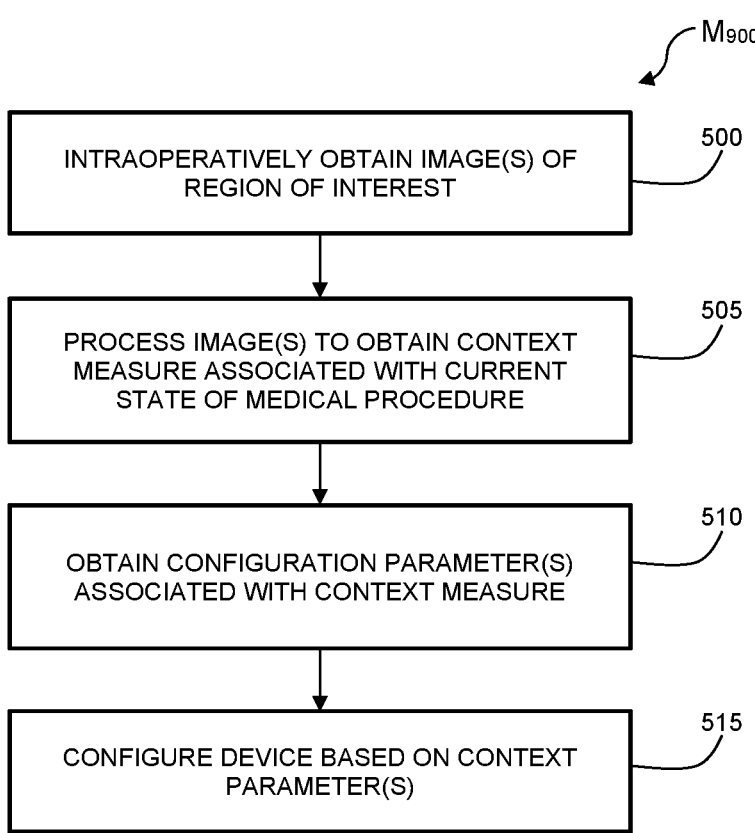
FIG. 9 is a flow chart illustrating a method of intraoperatively configuring one or more devices, based on the image-based detection of a context measure associated with a medical procedure.

Referring to FIG. 9, this flow chart illustrates a method M₉₀₀ of intraoperatively configuring one or more devices, based on the image-based detection of a context measure associated with a medical procedure, in accordance with an embodiment of the present disclosure. In step 500, one or more images are obtained during the medical procedure. The one or more images are then processed in step 505 to obtain, e.g., calculate, at least one context measure associated with the current state of the medical procedure. Examples of various context measures and methods of obtaining the context measures are below described. The one or more context measures are then employed to obtain one or more configuration parameters for adaptively and intraoperatively configuring at least one device that is employed during the medical procedure.

Still referring to FIG. 9, in one example implementation, optical image analysis is employed to obtain an image measure associated with a tissue type that is exposed, or otherwise detectable, at a present state of the medical procedure. One or more optical images are intraoperatively obtained and processed to determine the presence of one or more tissue types; and one or more context measures are provided that are associated with the detection of the one or more tissue types. The one or more context measures are then used to determine one or more customized configuration parameters. Various image processing methods are employed in order to identify the presence of a tissue type. For example, in one example implementation, tissue identification is performed via hyperspectral optical imaging. Hyper-spectral imaging is accomplished by scanning a spectrally-resolved optical detector across the region of interest and either collecting signals associated with multiple wavelengths at each scan point or collecting multi-spectral detector images. Various types of hyperspectral detectors and configurations are used.

Referring to FIG. 10A, this flow chart illustrates a method M$_{10A}$ of performing tissue identification via hyperspectral imaging, in accordance with an embodiment of the present disclosure. In step 520, hyperspectral image data is obtained by intraoperatively imaging a region of interest. The hyperspectral image data comprises per-pixel spectral data. The spectral data may be provided as a set of values, at wavelengths spanning a spectral range of interest that defines a digitized spectrum, or as discrete values, at a small set of wavelengths or wavelength bands, such as red-green-blue intensity data. In the example method, the per-pixel spectral data is processed, in step 525, to identify groups of adjacent pixels having a similar spectral response, thereby spectrally segmenting the image into one or more regions of similar spectral content. Pixels with similar spectral content are identified, based on the calculation of a spectral similarity measure between adjacent pixels.

Still referring to FIG. 10A, for example, a spectral similarity measure for two pixels is calculated by summing, over all wavelengths, the square of the difference between the values of the two intensity spectra (optionally after initially normalizing the two spectra), and dividing the result by the square of the average net intensity (summed over all wavelength values) of the two pixels. In such a case, two pixels are deemed to have similar spectral responses if their spectral similarity measure is less than a pre-selected threshold value. A suitable threshold value depends on the degree of spectral similarity that is sought, which depends on the type of medical procedure that is being performed.

Still referring to FIG. 10A, in one example implementation, when at least two adjacent pixels are found to have spectral similarity, the subsequent calculation of the spectral similarity measures for each additional adjacent pixel is performed by summing, over all wavelength values, the square of the difference between the values of (i) the intensity spectrum of the adjacent pixels and (ii) the average intensity spectrum of all other pixels already having been deemed to be similar, and dividing this result by the square of the average intensity of all other pixels having been deemed to be similar. The above similarity method is merely one example method; and other methods may be employed to obtain a similarity measure between pixels.

Still referring to FIG. 10A, if a region is identified as having spectral similarity, e.g., similarity within the pixels spanning the region, then the average spectral response for the pixels within the region is employed for tissue identification, as shown at step 530 of FIG. 10. For example, the average spectral response for the region is compared to one or more reference spectra, wherein each reference spectrum is associated with a given tissue type; for example, a particular spectrum is correlated with tumor tissue, white brain matter, or grey brain matter. The comparison is performed using a similarity measure as above described. In some embodiments, the comparison is performed only for one or more regions having a number of pixels that exceeds a minimum value, such that tissue identification is only performed for regions beyond a threshold size.

Still referring to FIG. 10A, the similarity measure between an average spectral response of an identified region and a given reference spectrum is employed to provide a confidence measure associated with tissue identification, wherein a higher confidence measure indicates a higher probability that the tissue within the identified region corresponds to the tissue type of the reference spectrum. In one example implementation, a region is associated with a tissue type if the confidence measure exceeds a preselected value. In cases in which two or more tissue types are identified, based on having confidence factors that exceed a threshold, the tissue is then identified, based on the tissue type having the higher confidence measure. The identified tissue type, or an identifier associated with the identified tissue type, provides a context measure associated with the current state of the medical procedure.

Still referring to FIG. 10A and referring back to FIG. 8, the image processing steps, above described, are performed by an image processing module 478 of the control and image processing module 400. Furthermore, the spectral similarity analysis, above described, is performed by the context analysis module 486. The preceding example method of performing hyperspectral tissue identification is but one method of processing hyperspectral image data in order to identify a tissue type and other methods may be employed without departing from the scope of the present disclosure. For example, methods of hyperspectral imaging are disclosed in PCT Patent Application No. PCT/CA2014/050268, titled "SURGICAL IMAGING SYSTEMS", filed on Mar. 14, 2014, which is incorporated herein by reference in its entirety.

Still referring to FIG. 10A, tissue identification is performed according to methods other than hyperspectral imaging. For example, fluorescence spectral image data or Raman spectral image data is obtained and processed, in a manner as above described, to identify one or more tissue types, based on similarity to reference spectra. For example, in the case of Raman imaging, tissue identification is performed by Raman imaging or by scanning a Raman point probe over multiple locations within a region of interest. In some embodiments, Raman imaging is combined with optical imaging in order to identify one or more tissue types.

Still referring to FIG. 10A and referring back to FIG. 8, after obtaining a context measure associated with the current state of the medical procedure (in this case, associated with an identified tissue type), the control and processing unit 400 may be employed to obtain configuration parameters for intraoperatively configuring one or more devices based on the context measure. The configuration parameters are obtained from pre-selected configuration data associating customized configuration parameters for one or more devices with different context measures. The customized configuration parameters are employed to adaptively configure the device during the medical procedure. This employment of customized configuration parameters is performed in a manner similar to the preceding embodiment in which the configuration parameters are obtained for configuring a device based on the identity of medical instruments.

Referring to FIG. 10B, this table illustrates configuration data that associates configuration parameters for illuminators 265 with one or more tissue types, in accordance with an embodiment of the present disclosure. For example, one or more tissue types are associated with a pathology, such as a tumor. An example of a configuration parameter for the illumination is the optical illumination spectrum. The spectrum is modified such that the illumination light either has greater depth penetration or enhances surface contrast based on the scattering and absorption properties of the tissue. This increase in either light penetration or surface contrast enables tissue features that are not visible under white light to be visible, and, as such, enables better tissue identification. Increased light penetration allows visualization of subsurface structures embedded in the tissue, while enhanced surface contrast allows visualization of fine surface features. Example illumination spectra parameters are provided for brain white matter, brain grey matter, and muscle. These three tissues strongly absorb light below 500 nm, 550 nm, and 650 nm, respectively, with lower absorption above these levels.

Still referring to FIG. 10B, in another example implementation, optical image analysis, such as the above described image analysis methods, is employed for identifying the intraoperative presence of one or more types of fluids. For example, the aforementioned example embodiment, involving hyperspectral tissue analysis, may be adapted to detect the presence of one or more fluids, based on a comparison to reference spectra from known fluids. For example, such a method is employed to detect the presence of biological fluids, such as blood and non-biological fluids, e.g., a saline fluid.

Still referring to FIG. 10B, in one example implementation, the intraoperative identification of the presence of a fluid is employed to improve imaging performance. A significant issue with current surgical optical systems and devices is glare caused by fluids that reflect illumination within a surgical cavity. The glare can cause imbalance in the dynamic range of an imaging camera, thereby causing the upper range of the camera's dynamic range to become saturated. In addition, glare can cause the illumination intensity across the frequency spectrum of an imager to be unbalanced, depending on the illumination and conditions of the medical procedure. Accordingly, in some embodiments, configuration parameters, associated with the intraoperative presence of a given fluid type, are provided for intraoperatively reconfiguring one or more components of an optical imaging system in order to improve imaging conditions. For example, configuration parameters are provided for modifying and/or improving image quality metrics, such as color and white balance.

Still referring to FIG. 10B, in another example implementation, optical image analysis is employed to obtain an image measure that is indirectly associated with the presence of one or more tissue types, fluids, or other material properties. For example, although the preceding example embodiments employed a method in which an average spectral response from an identified region is compared with a set of reference spectra associated with tissue or fluids, in other embodiments, the average spectral response, or another suitable imaging measure, may be compared with reference spectra that are not directly associated with a given tissue or fluid type.

Referring to FIG. 11A, this flow chart illustrates a method $M_{11A}$ of identifying the phase of a medical procedure based on hyperspectral imaging, in accordance with an embodiment of the present disclosure. In this embodiment, the reference spectra is associated with a phase or step of the medical procedure. Steps 540 and 545 are performed in a manner similar to steps 520 and 525 of the preceding method, as shown in FIG. 10A, wherein image data (such as hyperspectral image data) is intraoperatively acquired and processed to obtain one or more regions with a similar spectral response. In step 550, an average spectral response from an identified region is compared with reference spectra that are associated with different phases of the medical procedure. For example, one or more reference spectra are provided that are associated with a first phase of a medical procedure, while one or more other reference spectra are provided that are associated with a second phase of the medical procedure. For example, reference spectra may, instead, be obtained from previous medical procedures, such that a set of reference spectra are provided, wherein each reference spectra is associated with a given phase of the medical procedure. Finally, in step 555, the phase of the medial procedure is obtained, based on the similarity between the average spectral response and the reference spectra (methods of similarity analysis were described in the preceding example pertaining to tissue type analysis).

Still referring to FIG. 11A, in such an example embodiment, the context measure that is employed to determine one or more configuration parameters for intraoperative configuring a device is the identified phase of the medical procedure. The reference spectra, associated with different phases of the medical procedure, is produced according to several different methods. In one embodiment, the reference spectra may be obtained from previously performed surgical procedures. For example, spectra obtained at different phases of a number of prior medical procedures may be obtained and employed to provide reference spectra pertaining to the different phases of the medical procedure. In one example method, multiple spectra is obtained for each phase of the medical procedure and averaged to produce a representative average spectra for each phase of the medical procedure. In another example implementation, reference spectra, corresponding to different phases of the medical procedure, is produced, based on reference spectra of tissues and/or fluids that are expected to be exposed at different phases of the medical procedure.

Referring to FIG. 11B, this table illustrates configuration data that associates configuration parameters for a camera 255 with the phase of a medical procedure, in accordance with an embodiment of the present disclosure. An example of configuration data that associates configuration parameters for camera 255 with different phases of the medical procedure is shown. During the craniotomy, the camera may, or may not, be utilized by the surgeon, given the field of view is normally large enough for the surgeon to accurately perform the step without requiring assistance; hence, the camera will remain in an neutral state with no zoom. During cannulation, the robotic arm, holding the camera, disposes the camera in a position and an orientation relative to the port to provide a view of the graduation marks on the introducer. As the introducer, with the attached port, is penetrated into the brain to access the tumor, the graduation marks provide an indication of the depth of the instrument. As such, during this stage, a view requires, at a minimum, the ability to decipher the graduation marks on the port. During gross and fine resection, the camera is vital to the surgeon as the camera provides a view down the port where the surgeon is performing surgery and where the surgeon cannot view well with the surgeon's own eyes. At these stages, the camera is zoomed to different views, such as the entire distal end of the port as well as the particular tissue being resected during fine resection.

Figure 12:
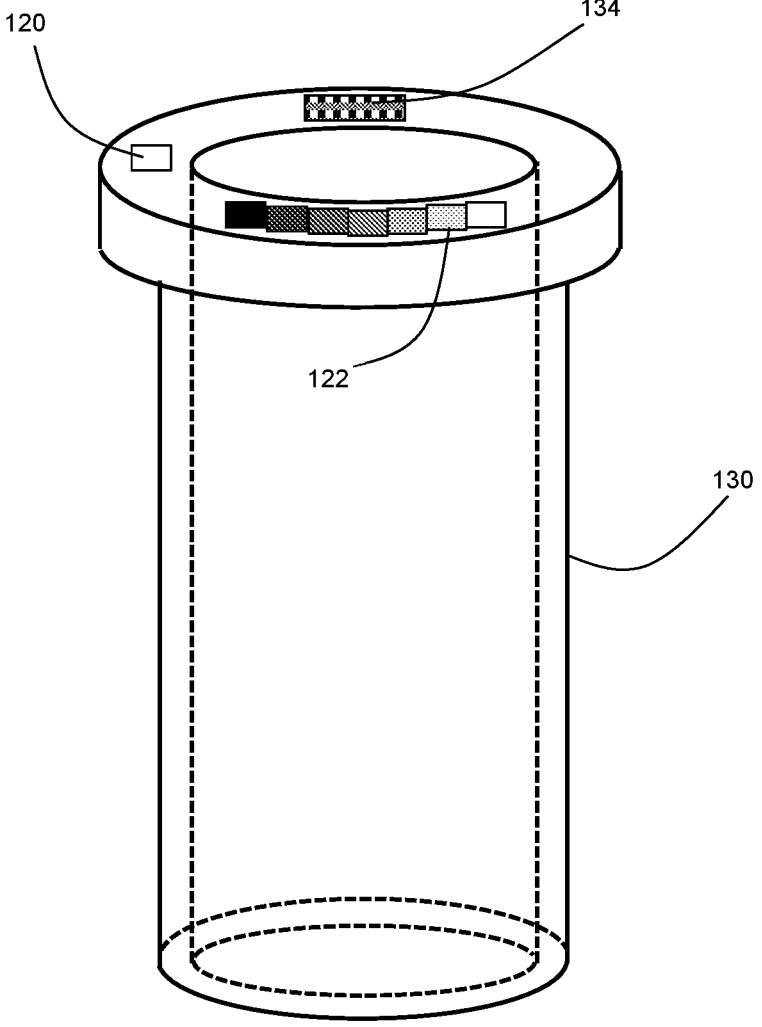
FIG. 12 is a diagram illustrating an access port having calibration features or targets that can be imaged and analyzed to automatically obtain one or more measures associated with color balance, white balance, dynamic range, and illumination uniformity.

Referring to FIG. 12, this diagram illustrates an access port 130 having calibration features or targets 134 that can be imaged and analyzed to automatically obtain one or more measures associated with color balance, white balance, dynamic range, and illumination uniformity, in accordance with an embodiment of the present disclosure. In one example, by using the calibration features or targets 134 on the access port 130 and using known properties of the optical system, intraoperative images, containing the calibration features 134, is analyzed to automatically obtain a measurement associated with color balance, white balance, dynamic range, and illumination uniformity (spatial uniformity). Several calibration features 134 are explained as follows. Item 120 is a white balance feature in which the processing system analyzes the image and uses this feature as the "true white" color and then adjusts its configuration parameters, such as its color mapping to confirm that the "white" color being depicted is the same "white" color as the calibration feature. Item 122 is a grey scale balance calibration feature, used in a similar manner to the one described above, for adjusting the imaging device configuration to match a grey balance range. Item 134 is an RGB color balance calibration feature.

Still referring to FIG. 12, the imaging device, when oriented to view down the port to the distal end, can use these calibration features 134 in the imaging focus periphery to obtain the optimal image for the surgery. In another embodiment, the calibration features 134 are oriented within the opening of the port on the sidewalls. This embodiment provides better calibration of the imaging device to match the imaging device with the interior of the port. Several published algorithms are employed to automatically adjust these image characteristics. For example, the algorithm published by Jun-yan Huo et. al. ("Robust automatic white balance algorithm using gray color points in images," IEEE Transactions on Consumer Electronics, Vol. 52, No. 2, May 2006) is employed to achieve automatic white balance of the captured video data. In other embodiments of the present disclosure, systems and methods are provided for adaptively and intraoperatively controlling multiple imaging modalities. An automated system employed during a medical procedure, as shown in FIG. 5A, comprises multiple imaging modalities that are selectively controlled during a medical procedure.

Figure 13A:
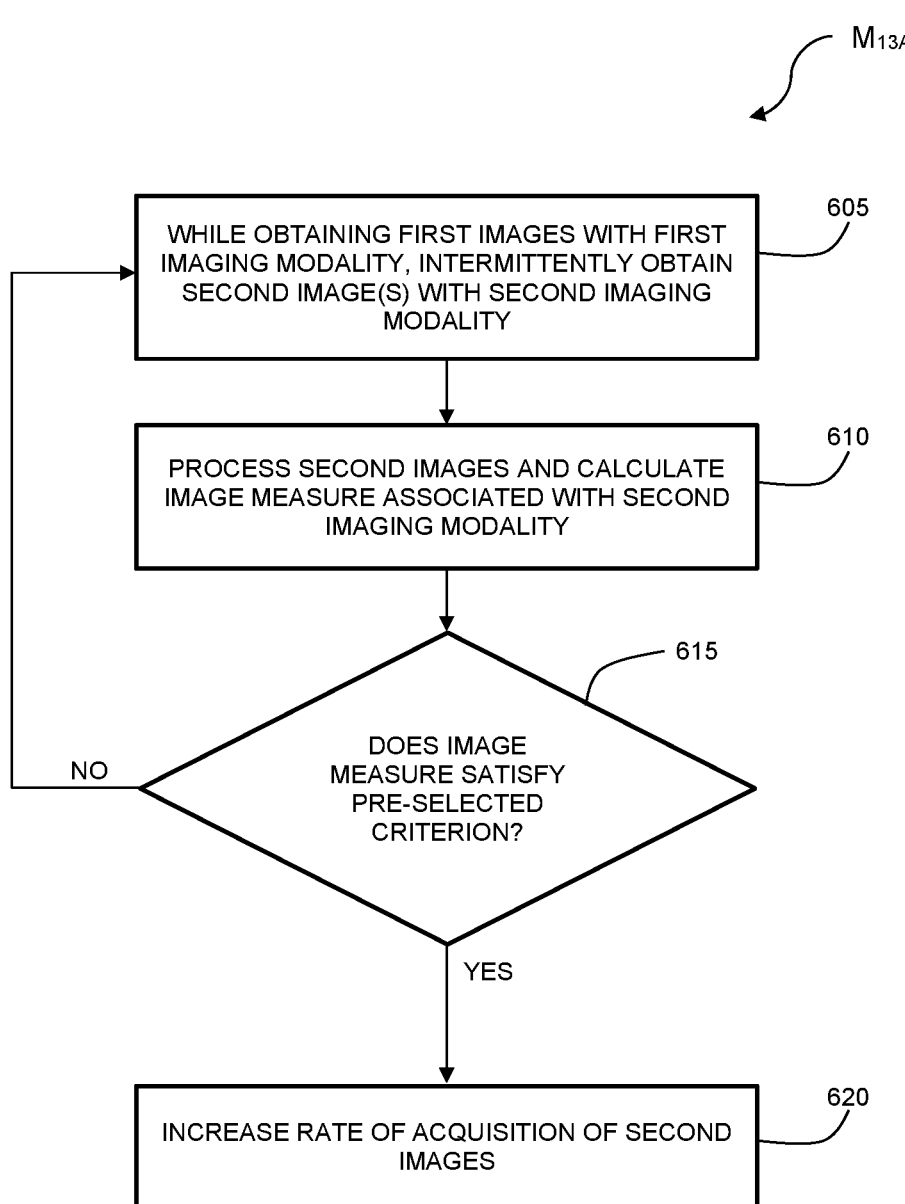
FIG. 13A is a flow chart illustrating a method of controlling a second imaging modality, based on intermittent sampling and processing of image data from the second imaging modality while obtaining images using a first imaging modality.

Referring to FIG. 13A, this flow chart illustrates a method $M_{13A}$ of controlling a second imaging modality, based on intermittent sampling and processing of image data from the second imaging modality while obtaining images using a first imaging modality, in accordance with an embodiment of the present disclosure. At least two imaging modalities are controllable by the control and processing unit 400, such that the at least two imaging modalities are selectively employed during a medical procedure. Such an embodiment provides intelligent and contextually relevant control of the second imaging modality relative to the first imaging modality.

Still referring to FIG. 13A, the first imaging modality and the second imaging modality need not be associated with two separate imaging devices; and, in some example implementations, an imaging device that is initially configured to obtain images by using a first imaging modality is adaptively and dynamically configured to obtain images with a second imaging modality by modifying the imaging device. For example, an optical imaging device may be dynamically switched to fluorescence mode via the introduction of one or more filters into the optical beam path. In another example, an intraoperative magnetic resonance imaging system may be dynamically modified to switch between different modes of operation, e.g., T1 weighted image vs. T2 weighted image, via changes to the transmit and receive sequence.

Still referring to FIG. 13A, images from a first imaging modality are intraoperatively obtained. For example, the first imaging modality employs visible imaging using white light illumination. While obtaining the images from the first imaging modality, a second imaging modality is intermittently employed in order to obtain images, as indicated at step 605. For example, the second imaging modality employs another type of optical imaging, such as fluorescence imaging. During this phase, the acquisition rate of the images from the second imaging modality may be lower than the acquisition rate of the images from the first imaging modality. In some non-limiting example implementations, the initial ratio of the acquisition rate of the first imaging modality to that of the second imaging modality is greater than or equal to approximately 2, 5, 10, 50, 100, $10^3$, $10^4$, $10^5$, or $10^6$.

Still referring to FIG. 13A, the images from the second imaging modality are processed in order to obtain an image measure that is employed to determine whether to continue imaging with the second imaging modality. Various examples of image measures, and methods of calculating such image measures, are below described in detail. In step 615, the image measure is compared with a pre-selected criterion (or criteria) in order to determine whether to continue imaging with the second imaging modality. If the image measure meets the pre-selected criterion and continuing imaging with the second imaging modality is determined to be suitable, the acquisition rate of images from the second imaging modality is increased at step 620. On the other hand, if the image measure does not meet the pre-selected criterion in step 615, one or more additional images are obtained using the second imaging modality; and the assessment is repeated until the pre-selected criterion is met.

Still referring to FIG. 13A, the image measure that is obtained to determine whether to increase the acquisition rate of the second imaging modality is obtained according to a wide range of methods. In one example embodiment, the image measure is associated with a performance measure of the second imaging modality. For example, the image measure involves a determination of a measure of signal-to-noise ratio of imaging with the second imaging modality, such that, when the imaging measure associated with the signal-to-noise ratio exceeds the pre-selected criterion in step 615, the acquisition rate of the second imaging modality is increased. Another example of a performance-related image measure is a measure of the intensity of the signal that is obtained with the second imaging modality. Yet another example of a performance-related image measure is the amount of signal within a given frequency range or spectral range. These performance measures are evaluated on a global basis by using one or more statistical measures or on a local or regional basis. For example, the pre-selected criterion evaluated in step 615 requires that a given performance threshold is satisfied by a pre-selected fraction of the pixels forming the image obtained via the second imaging modality. A plurality of images are obtained from the second imaging modality; and an image measure is obtained by processing the plurality of images (for example, via averaging the images).

Still referring to FIG. 13A, while the preceding paragraphs describe the use of a single image measure, multiple image measures and associated criterion are processed in order to determine whether to increase the acquisition rate of the second imaging modality. In one example implementation, when the acquisition rate of the second imaging modality is increased in step 620, the acquisition rate of the first imaging modality is reduced. In another example implementation, when the acquisition rate of the second imaging modality is increased in step 620, the acquisition rate of the first imaging modality is maintained. In another example implementation, when the acquisition rate of the second imaging modality is increased in step 620, the acquisition of images from the first imaging modality is either terminated or suspended.

Still referring to FIG. 13A, in one example embodiment, after having increased the acquisition rate of the second imaging modality, based on the determination that an image measure has met pre-selected criterion, steps 610 and 615 are performed to assess whether the image measure, associated with the second imaging modality, continues to meet the pre-selected criterion. In the event that the image measure fails to meet the pre-selected criterion, the acquisition rate of the second imaging modality is reduced; and the method is repeated (starting with step 605).

Still referring to FIG. 13A, in one example embodiment, additional actions are taken after having determined that the image measure, associated with the second imaging modality, satisfies the pre-selected criterion. For example, in a manner similar to the previously described embodiments, one or more devices that are used during the medical procedure are reconfigured, e.g., by obtaining new configuration parameters from configuration data associating the configuration of one or more devices with the assessment of the criterion in step 615. In one example implementation, a user interface that displays the images, obtained from the first imaging modality, are reconfigured to additionally, or alternatively, display the images from the second imaging modality.

Still referring to FIG. 13A, the additional images from the second imaging modality are displayed according to a wide variety of different configurations, such as displaying the images from the first and second imaging modalities in a side-by-side configuration or in an overlaid configuration (optionally after having registered the images from the first imaging modality with those of the second imaging modality).

Figure 13B:
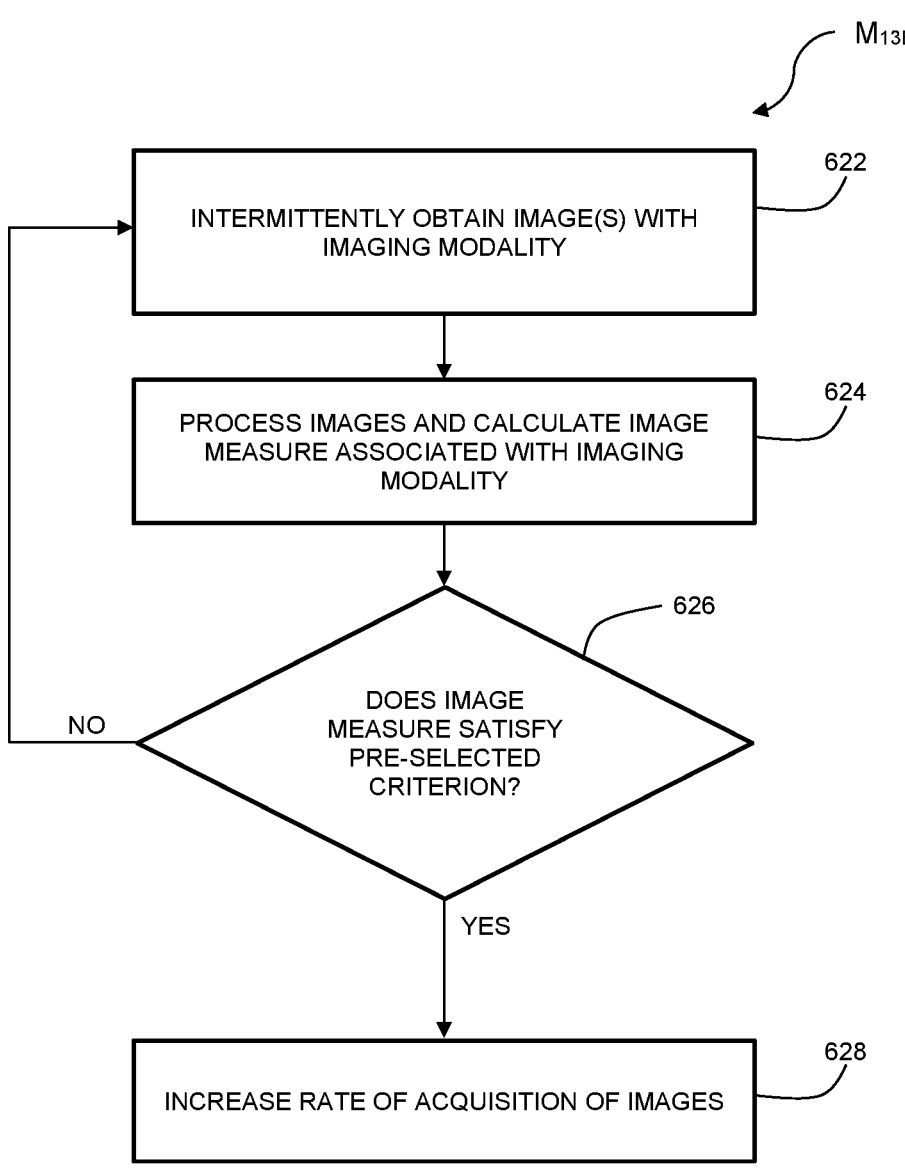
FIG. 13B is a flow chart illustrating an adaptive and interoperative method of controlling the acquisition rate of images pertaining to an imaging modality.

Referring to FIG. 13B, this flow chart illustrates an adaptive and interoperative method $M_{13B}$ of controlling the acquisition rate of images pertaining to an imaging modality, in accordance with an embodiment of the present disclosure. In some embodiments, a method, based on that shown in FIG. 13A, is implemented, based solely on the intermittent acquisition of images from one imaging modality. In step 622, an imaging modality is employed to intraoperatively obtain images. The images are intermittently obtained at an initial pre-selected frame rate. The one or more images are processed to obtain an image measure in step 624. In step 626, the image measure is compared to pre-selected criterion; and, if the criterion is met, the acquisition rate of the imaging modality is increased.

Figure 14:
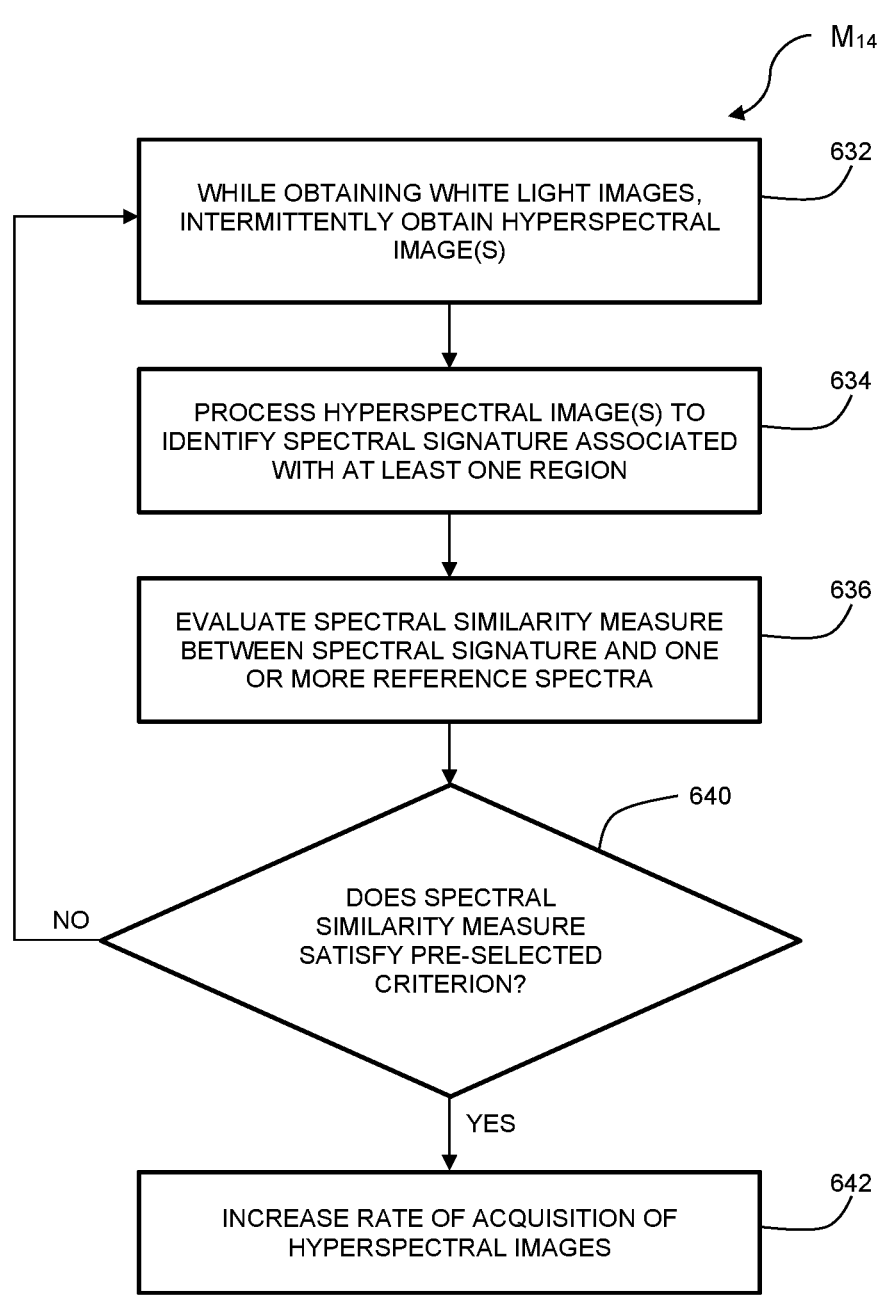
FIG. 14 is a flow chart illustrating a method of intraoperatively and adaptively controlling the acquisition of images from white light and hyperspectral imaging modalities.

Referring to FIG. 14, this flow chart illustrates an implementation of a method $M_{14}$ of intraoperatively and adaptively controlling the acquisition of images from white light and hyperspectral imaging modalities, in accordance with an embodiment of the present disclosure. These imaging modalities are merely provided as examples. White light images are intraoperatively obtained; and, in step 632, one or more hyperspectral images are intermittently obtained while obtaining the white light images. For example, one or more hyperspectral images are obtained at a prescribed initial acquisition rate, such as a rate between an image per minute and an image per second.

Still referring to FIG. 14 and referring back to FIG. 5A, hyperspectral images are obtained via a separate hyperspectral imaging device. In one example implementation, a hyperspectral imaging device shares one or more components with the white light imaging device. For example, as illustrated in FIG. 5A, imaging optics assembly 260 are shared by both the camera 255 (which, in the present example, would be employed for white light imaging) and by a hyperspectral detector that interfaces with the optical system 250 through the auxiliary imaging modality assembly 275. The one or more hyperspectral images that are obtained in step 632 are then processed to obtain an image measure that is employed to determine whether to increase the acquisition rate of hyperspectral images. The image measure is associated with a wide range of metrics, associated with the suitability or feasibility of performing hyperspectral imaging, including one or more of those metrics above described.

Still referring to FIG. 14, in the present example, the image measure is obtained by processing the hyperspectral image data in order to identify the presence of one or more spectral signatures in step 634. The processing of the hyperspectral images is performed as described above in relation to FIG. 11A, wherein one or more regions are identified having a spectral similarity among pixels. Briefly, per-pixel spectral data from the hyperspectral images are processed to identify groups of adjacent pixels having a similar spectral response, thereby spectrally segmenting the image into one or more regions of similar spectral content. Pixels with similar spectral content are identified based on the calculation of a spectral similarity measure between adjacent pixels. If a region is identified as having spectral similarity within the pixels spanning the region, then the average spectral response for the pixels within the region is employed as the spectral signature.

Still referring to FIG. 14, a spectral similarity measure is evaluated between an identified spectral signature and one or more reference spectra in step 636. For example, the spectral signature is compared to one or more reference spectra, wherein the reference spectra are each associated with a given tissue type, fluid type, chemical, or biological composition. For example, the spectral signature is compared with one or more pathological tissue types, such as different types of tumors. The comparison is performed using a similarity measure as above described. In some embodiments, the comparison is performed only for one or more regions having a number of pixels that exceeds a minimum value, such that similarity assessment is only performed for regions beyond a threshold size.

Still referring to FIG. 14, if the spectral similarity measure satisfies a pre-selected criterion for one of the reference spectra, e.g., exceeds a pre-selected threshold, in step 640, then the acquisition rate of the second imaging modality is increased at step 642. On the other hand, if the pre-selected criterion is not met, then the process is repeated and additional hyperspectral images are obtained in 632 and subsequently evaluated for spectral similarity with the reference spectra.

Figure 15:
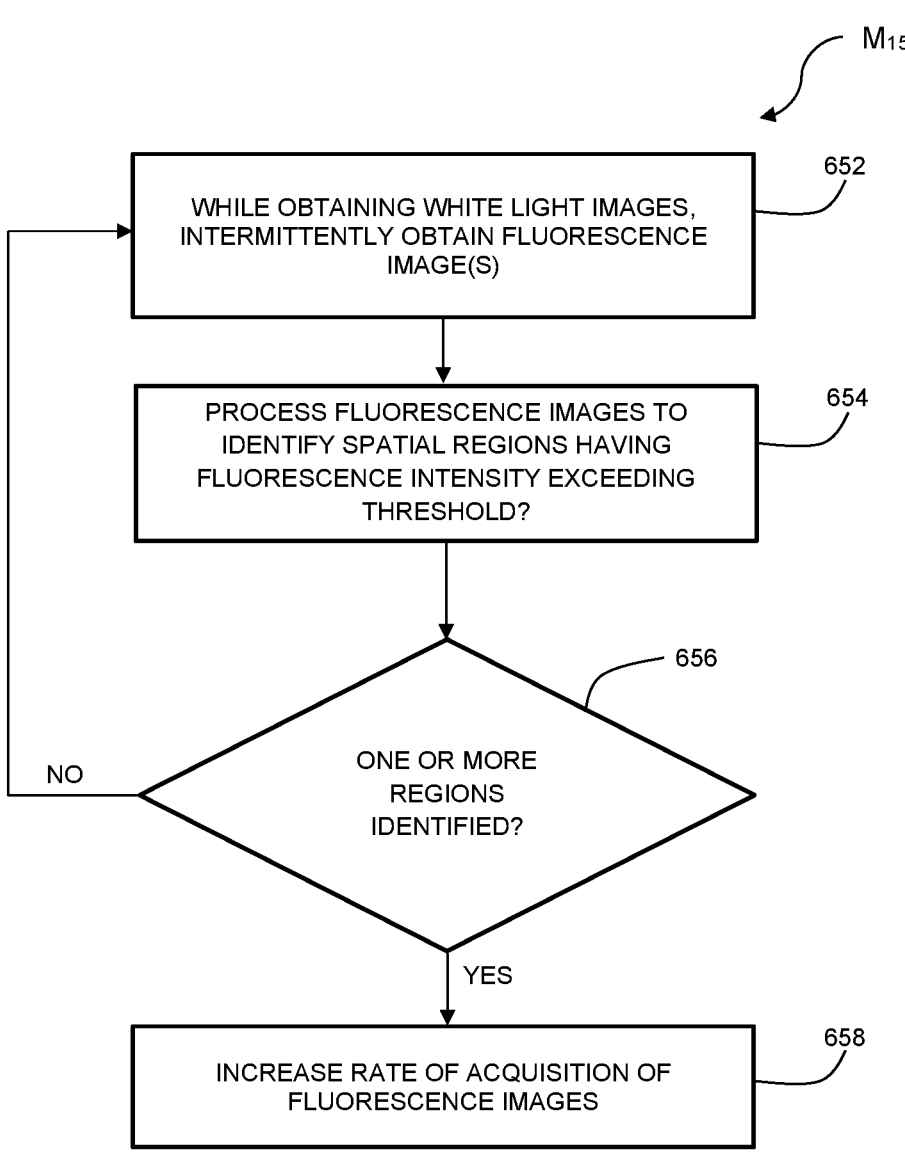
FIG. 15 is a flow chart illustrating a method of adaptively controlling the use of fluorescence imaging, based on the intermittent sampling of and processing of fluorescence images.

Referring to FIG. 15, this flow chart illustrates a method $M_{15}$ of adaptively controlling the use of fluorescence imaging, based on the intermittent sampling of and processing of fluorescence images, in accordance with an embodiment of the present disclosure. In another example implementation, the methods, as illustrated in FIGS. 13A and 13B, are employed to adaptively control the use of fluorescence imaging. For example, in one example implementation, the method, as illustrated in FIG. 13A, is performed, such that the first imaging modality comprises white light imaging and the second imaging modality comprises fluorescence imaging.

Still referring to FIG. 15, an example implementation of this method is shown. In step 652, one or more fluorescence images are intermittently obtained while obtaining while light images. Fluorescence image acquisition is interleaved with white light image acquisition in order to avoid crosstalk between the two modalities. The fluorescence images are processed to calculate an image measure associated with the intensity of the fluorescence signal. For example, the image measure is obtained by calculating the net fluorescence intensity for all image pixels.

Still referring to FIG. 15, alternatively, a spatially resolved measure of fluorescence intensity is calculated. For example, in step 654, the per-pixel fluorescence intensity data is processed to identify groups of adjacent pixels having a fluorescence intensity exceeding a pre-selected threshold value, thereby segmenting the image into one or more regions having a fluorescence intensity above the threshold value. In one example, an identified region is required to have a minimum number of pixels, such that only regions greater than a minimum area are considered. If one or more regions are identified in step 656, the rate of acquisition of fluorescence images is increased.

Still referring to FIG. 15, in other example implementations involving fluorescence imaging, other measures, associated with the fluorescence image, are additionally, or alternatively, obtained and compared to pre-selected criteria in order to determine whether to increase the fluorescence image acquisition rate. For example, a measure, associated with the signal-to-noise ratio of one or more fluorescence images, is obtained; and the fluorescence image acquisition rate is increased if the measure exceeds a pre-selected threshold. In another example, the fluorescence image is spectrally resolved, e.g., using hyperspectral fluorescence detection, and the hyperspectral image processing methods, as shown in FIG. 14, is employed.

Figure 16:
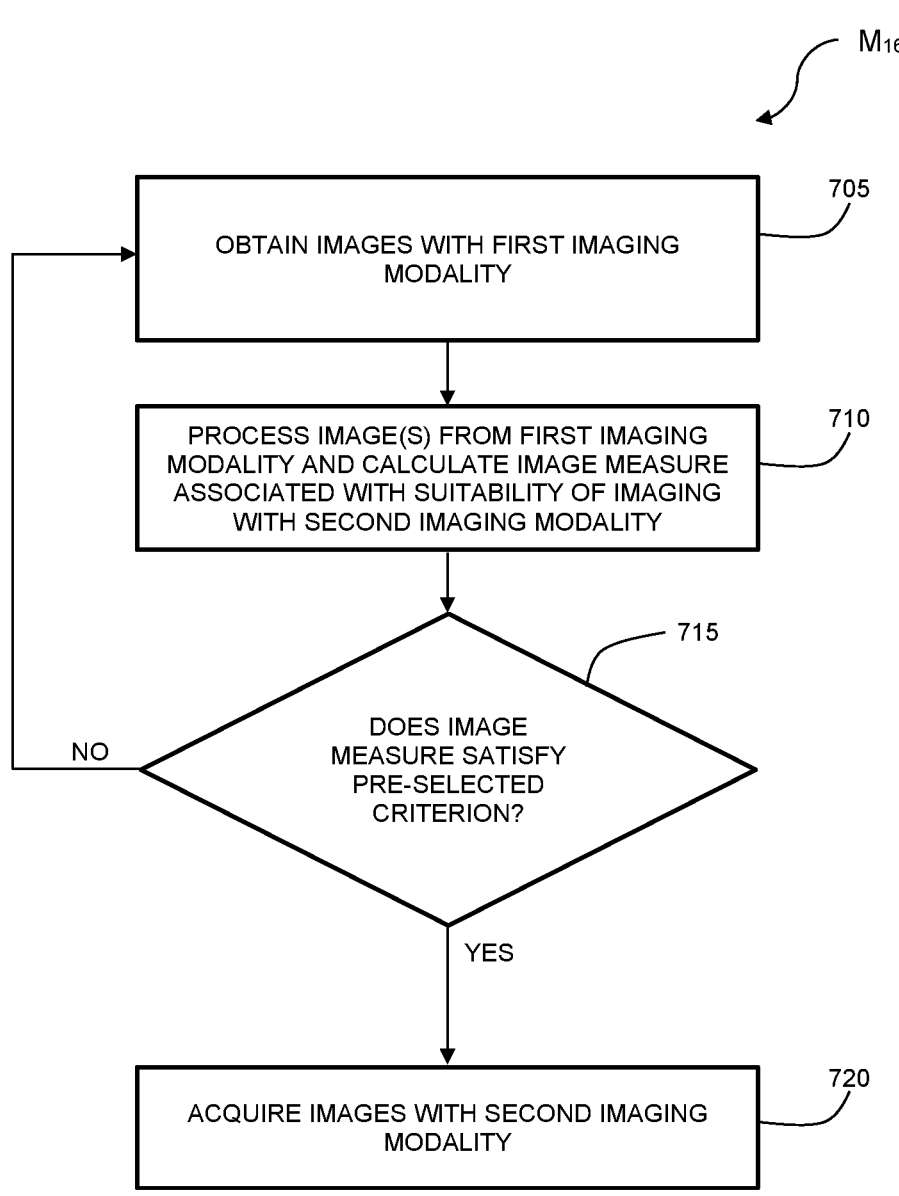
FIG. 16 is a flow chart illustrating a method of obtaining and processing images from a first imaging modality for triggering acquisition of images from a second imaging modality.

Still referring to FIG. 15 and referring ahead to FIG. 16, the preceding embodiments involve the intermittent and intraoperative sampling of images from an imaging modality and the processing of the images in order to determine whether to increase the acquisition rate of the images. In another example embodiment, images from a first imaging modality are obtained and processed in order to trigger the use of a second imaging modality.

Referring to FIG. 16, this flow chart illustrates a method $M_{16}$ of obtaining and processing images from a first imaging modality for triggering acquisition of images from a second imaging modality, in accordance with an embodiment of the present disclosure. In step 705, a first imaging modality is employed to intraoperatively obtain images. The images are then processed in step 710 in order to obtain an image measure associated with the feasibility or suitability of performing imaging with a second imaging modality.

Examples of such image measures are below described. The image measure is then compared to a pre-selected criterion in step 715; and, if the criterion is met, images are subsequently acquired with the second imaging modality in step 720.

Still referring to FIG. 16, as in the preceding embodiment, the first imaging modality and the second imaging modality need not be associated with two separate imaging devices. In some example implementations, an imaging device that is initially configured to obtain images using a first imaging modality is adaptively and dynamically configured to obtain images with a second imaging modality by modifying the imaging device. For example, an optical imaging device is dynamically switched to fluorescence mode via the introduction of one or more filters into the optical beam path. In another example, an intraoperative magnetic resonance imaging system is dynamically modified to switch between different modes of operation, e.g., T1 weighted image vs. T2 weighted image, via changes to the transmit and receive sequence.

Still referring to FIG. 16, as above described, the image measure is associated with the feasibility or suitability of imaging with the second imaging modality. The image measure is obtained according to a wide range of methods. For example, in some example implementations, the image measure is associated with an impairment of the performance of the first imaging modality, such that, when the image measure exceeds a pre-selected threshold, switching to the second imaging modality is beneficial. For example, as below described, the first imaging modality comprises an optical imaging modality that suffers a performance degradation in the presence of glare; and the second imaging modality is insensitive or less sensitive to glare. In such a case, when the image measure has a value that is associated with glare, the criterion in step 715 will trigger the acquisition of images using the second imaging modality.

Still referring to FIG. 16, in another example embodiment, an image measure is associated with the determination of context measure, as described in relation to the preceding embodiments. For example, an image measure that is obtained provides an indication of the current phase of a surgical procedure, as above described. In such a case, the pre-selected criterion that is evaluated in step 715 comprises a list of phases of the medical procedure for which the second imaging modality is desirable or suitable.

Still referring to FIG. 16, in another example embodiment, the image measure is associated with a performance measure of the second imaging modality. For example, the image measure involves a determination of a measure of signal-to-noise ratio of imaging with the second imaging modality, such that, when the imaging measure associated with the signal-to-noise ratio exceeds the pre-selected criterion in step 715, the acquisition rate of the second imaging modality is increased. Another example of a performance-related image measure is a measure of the intensity of the signal that is obtained with the second imaging modality. Yet another example of a performance-related image measure is the amount of signal within a given frequency range or spectral range. These performance measures are evaluated on a global basis using one or more statistical measures or on a local or regional basis. For example, the pre-selected criterion evaluated in step 640, as shown in FIG. 14, may require that a given performance threshold is satisfied by a pre-selected fraction of the pixels forming the image obtained via the second imaging modality. A plurality of images are obtained from the second imaging modality; and an image measure is obtained by processing the plurality of images (for example, via averaging the images).

Still referring to FIG. 16, while the preceding paragraphs describe the use of a single image measure, multiple image measures and associated criterion are processed in order to determine whether to increase the acquisition rate of the second imaging modality. In one example implementation, when the acquisition images with the second imaging modality is initiated in step 720, the acquisition rate of the first imaging modality is reduced. In another example implementation, when the acquisition images with the second imaging modality is initiated in step 720, the acquisition rate of the first imaging modality is maintained. In another example implementation, when the acquisition images with the second imaging modality is initiated in step 720, the acquisition of images from the first imaging modality is terminated or suspended. In one example embodiment, after having initiated the acquisition of the images from the second imaging modality, based on the determination that an image measure has met pre-selected criterion, steps 710 and 715 are performed to assess whether the image measure, associated with the second imaging modality, continues to meet the pre-selected criterion. In the event that the image measure fails to meet the pre-selected criterion, the acquisition of images with the second imaging modality is reduced or terminated; and the method is repeated (starting with step 705).

Still referring to FIG. 16, in one example embodiment, additional actions are taken after having determined that the image measure, associated with the second imaging modality, satisfies the pre-selected criterion. For example, in a manner similar to the previously described embodiments, one or more devices that are used during the medical procedure are reconfigured, e.g., by obtaining new configuration parameters from configuration data associating the configuration of one or more devices with the assessment of the criterion in step 615, as shown in FIG. 13A. In one example implementation, a user interface that displays the images obtained from the first imaging modality is reconfigured to additionally, or alternatively, display the images from the second imaging modality. The additional images from the second imaging modality are displayed according to a wide variety of different configurations, such as displaying the images from the first and second imaging modalities in a side-by-side configuration or in an overlaid configuration (optionally after having registered the images from the first imaging modality with those of the second imaging modality).

Figure 17:
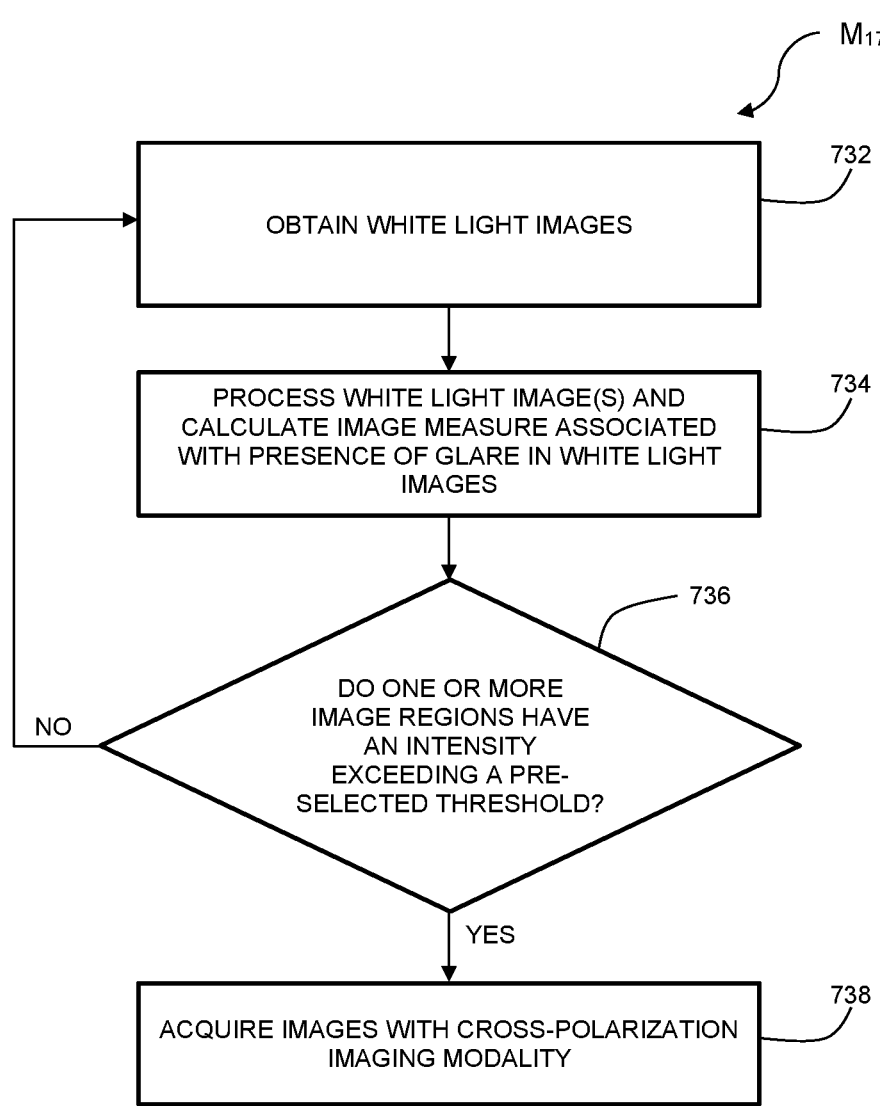
FIG. 17 is a flow chart illustrating a method of obtaining and processing white light images for triggering acquisition of images by using a hyperspectral imaging modality.

Referring to FIG. 17, this flow chart illustrates a method $M_{17}$ of obtaining and processing white light images for triggering acquisition of images, as shown in FIG. 16, by using a hyperspectral imaging modality, in accordance with an embodiment of the present disclosure. In this example implementation, the system automatically switches to a cross-polarized imaging device when a pre-selected criterion, associated with the detection of glare in the images from the white light imaging modality, is satisfied. As noted above, a significant issue with current surgical optical systems and devices is glare caused by fluids that reflect illumination within a surgical cavity. The glare can cause imbalance in the dynamic range of an imaging camera, thereby causing the upper range of the camera's dynamic range to become saturated. In addition, glare can cause the illumination intensity across the frequency spectrum of an imager to be unbalanced, depending on the illumination and conditions of the medical procedure.

Still referring to FIG. 17, white light images of a region of interest are initially obtained during a medical procedure at step 732. For example, such images are obtained by using the camera 255 of the optical system 250, as shown in FIG. 5A. In step 734, the white light images are processed to calculate an image measure associated with the presence of glare in the white light images. For example, this step is performed by identifying one or more of regions within the image (groups of adjacent pixels) having an intensity value above a pre-selected intensity, wherein the pre-selected intensity is indicative of glare conditions. If one or more of such regions are identified in step 736 (optionally where any given region has an area exceeding a pre-selected minimal area), then images are subsequently acquired using a cross-polarization imaging modality at step 738. The cross-polarization images are intermittently obtained while continuing to obtaining the white light images.

Still referring to FIG. 17, cross-polarized images are obtained via a separate cross-polarization imaging device or by modifying the optical device that is employed for white light imaging. For example, the device employed for white light imaging is modified by intraoperatively inserting, into the beam path of an illumination device, a first polarizer, and introducing, into the beam path of the optical imaging device, a second polarizer (an analyzer), wherein the first and second polarizers are oriented in a crossed configuration for performing polarization-sensitive imaging. In some example implementations, cross-polarization imaging is performed by using a high frequency polarization state actuation and deactivation device, a beam splitter, and an alternate camera, or a beam splitter with the same camera. In an example implementation in which a second imaging device is obtained for performing cross-polarized imaging, one or more cross-polarized images are concurrently obtained with the acquisition of white light images.

Still referring to FIG. 17, the additional images from the cross-polarization imaging modality are displayed according to a wide variety of different configurations, such as displaying the images from the white light and cross-polarization imaging modalities in a side-by-side configuration, in an overlaid configuration, or in a configuration in which the high-glare regions identified in the white light images are replaced with image data obtained from cross-polarization imaging.

Figure 18:
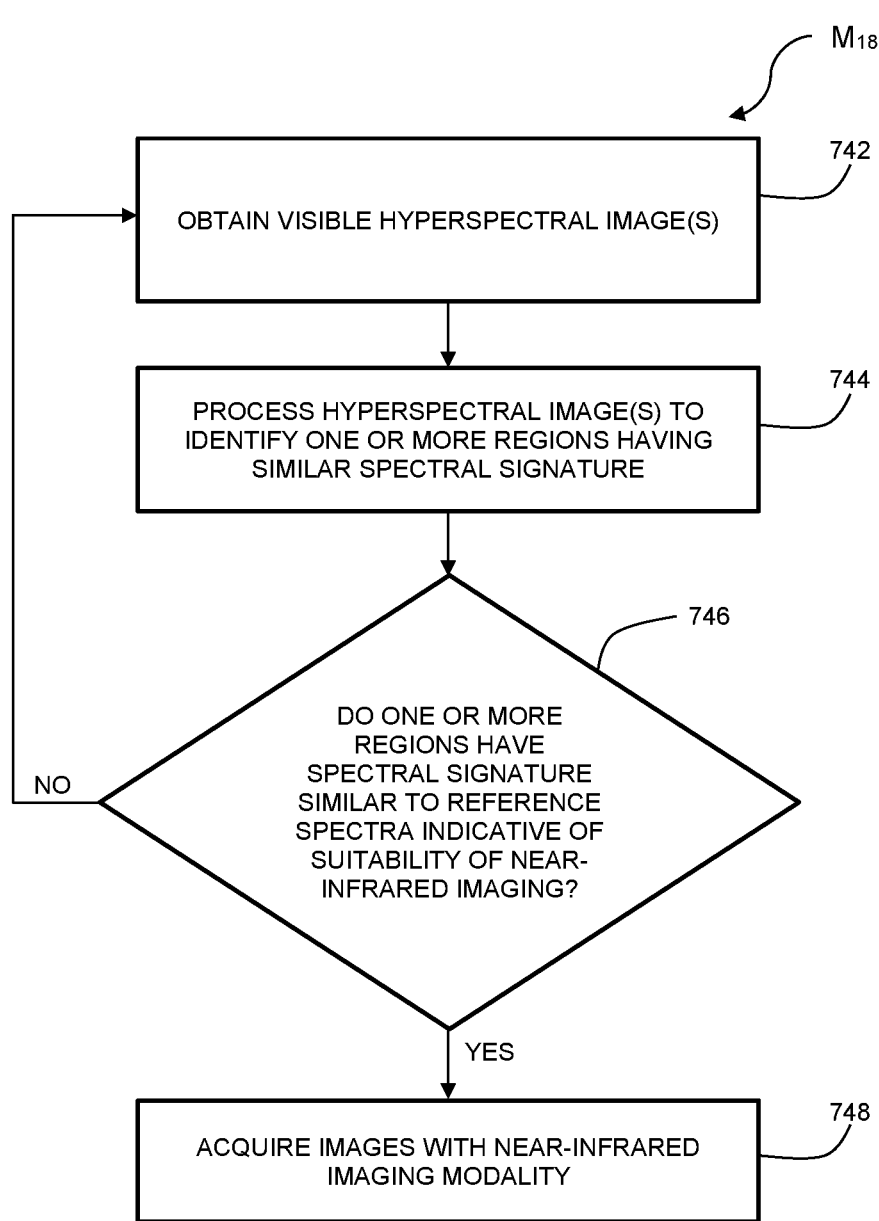
FIG. 18 is a flow chart illustrating a method of obtaining and processing hyperspectral images for triggering acquisition of images by using a near-infrared imaging modality.

Referring to FIG. 18, this flow chart illustrates a method $M_{18}$ of obtaining and processing hyperspectral images for triggering acquisition of images, as shown in FIG. 17, by using a near-infrared imaging modality. in accordance with an embodiment of the present disclosure. In this example implementation, the system automatically switches to a near-infrared imaging device when a pre-selected criterion, associated with the detection of a spectral signature in the hyperspectral images, is satisfied.

Still referring to FIG. 18, in step 742, one or more hyperspectral images are intraoperatively obtained. The one or more hyperspectral images are the processed, in step 744, in order to identify one or more spatial regions having a similar spectral signature. Example methods for identifying such regions and a characteristic spectral signature for a given region are above described in detail.

Still referring to FIG. 18, in step 746, the spectra signature from each identified region is compared to one or more reference spectra, wherein the reference spectra pertain to tissue types, fluids, material, or biological compositions that are known to be suitable or feasible for near-infrared imaging.

Still referring to FIG. 18, in another example, the spectral signature is processed to provide an image measure, associated with the relative spectral intensity within one or more spectral bands, wherein the spectral bands are known to be associated with materials that do not absorb near-infrared light. In other words, the spectral signature is processed to directly, or indirectly, identify the presence of a material that would support deeper image penetration via near-infrared imaging. The image measure is compared to pre-selected criterion in order to selectively trigger the use of the near-infrared imaging modality.

Still referring to FIG. 18, in one example implementation, multiple image measures are obtained and employed. For example, image measures, associated with the presence of both near-infrared absorbing substances and near-infrared transparent substances, are combined to determine whether to trigger the use of the near-infrared imaging modality. The spectral similarity is determined, for example, based on the calculation of a spectral similarity measure, as above described in detail. In the event that sufficient spectral similarity is found to occur between a spectral signature from the hyperspectral images and the reference spectra, then the acquisition of near-infrared images is triggered in step 748. The preceding example, involving the analysis of images from one imaging modality to trigger the acquisition of images from another imaging modality, are provided as non-limiting heuristic examples; and the method may be adapted to various combinations of imaging modalities without departing from the scope of the present disclosure. The additional images from the near-infrared imaging modality may be displayed according to a wide variety of different configurations, such as displaying the images from the hyperspectral and near-infrared imaging modalities in a side-by-side configuration, in an overlaid configuration, or in a configuration in which the regions identified in the hyperspectral images are replaced with image data obtained from near-infrared imaging.

Figure 21:
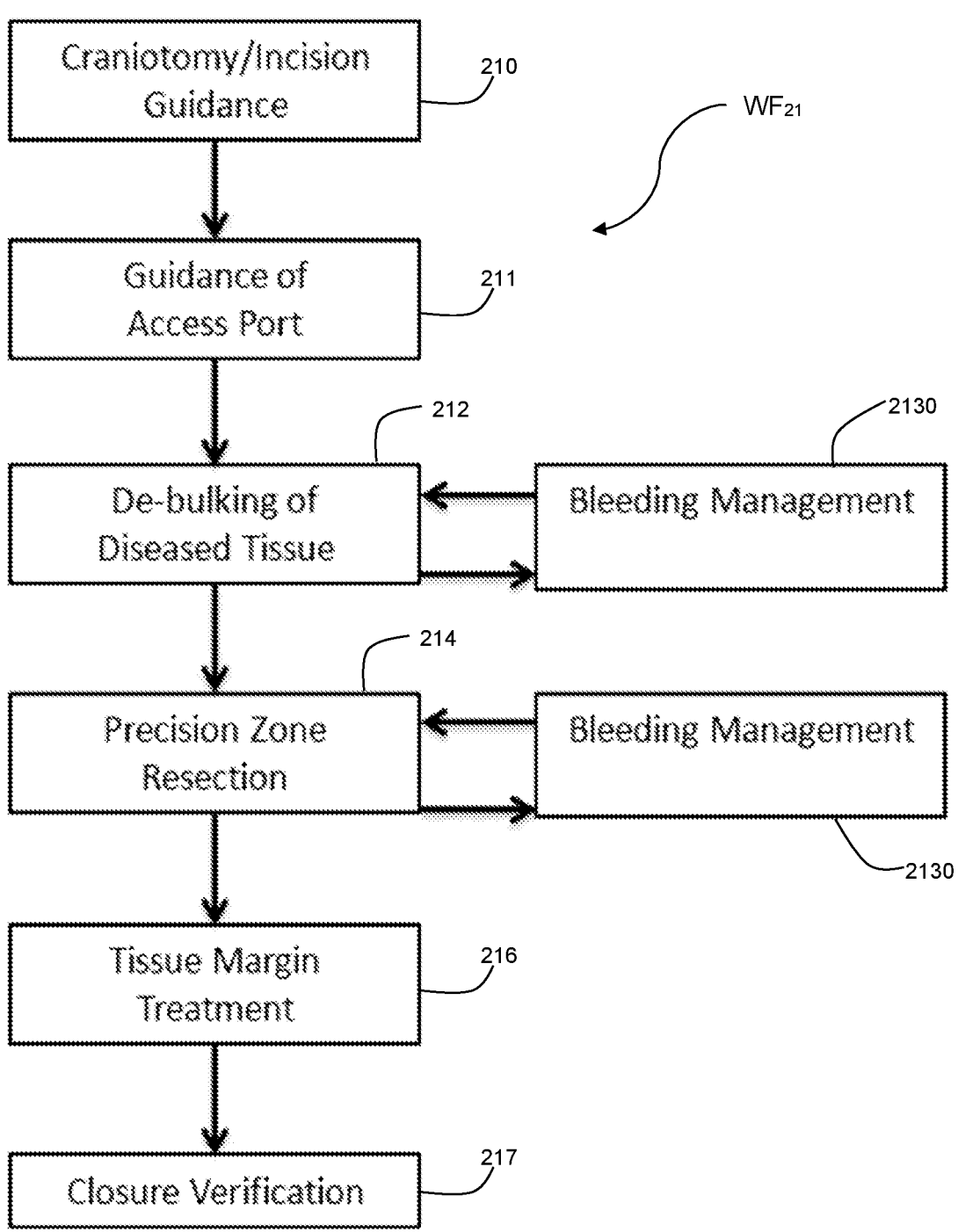
FIG. 21 is a flow chart illustrating workflow relating to the phases of a port based neurosurgery.

Referring to FIG. 21, this flow chart illustrates workflow $WF_{21}$ relating to the phases of a port-based neurosurgery, in accordance with an embodiment of the present disclosure. An exemplary port-based surgery flow, inclusive of the stages of surgery that a surgeon would undertake to complete the procedure, is shown. In each stage, applicable adaptive processes can run to streamline the procedure to provide more accurate and time efficient surgical procedures. These processes utilize various context measures ranging from some non-limiting examples being intraoperative imaging, temporal information, spatial positions of objects related to the surgery, medical instruments being used, intraoperative patient vitals (for example, breathing rate, blood pressure, etc.), etc. The following paragraph describes various adaptive processes that would be run with respect to the port-based procedure. Each stage of the surgery is identified using various context measures and are also provided below as non-limiting examples. Similar examples of configurations, based on context measures, are shown in FIG. 5J.

Still referring to FIG. 21, in the first stage 2100 of the surgery, the craniotomy/incision stage is identified by the navigation system's control and processing unit through the identification of either a scalpel or a neurosurgical drill being utilized by the surgeon through methods herein described. During this stage, an exemplary adaptive process involves adjusting a user interface (UI) that is being reconfigured to provide a digital display of the depth of the drill into the patient's skull as the surgeon is performing the craniotomy. The depth of the drill is calculated from the navigation system as the navigation system knows the spatial position and the pose of both the drill and the skull. Such examples of navigation system are described, in detail, in PCT Patent Application No. PCT/CA2014/050268, titled "SURGICAL NAVIGATION SYSTEM", and filed on Mar. 14, 2014, which is incorporated herein by reference in its entirety.

Still referring to FIG. 21, once the craniotomy has been completed, the next stage 2110 of the surgery is cannulation (Guidance of Access Port). This stage can be identified by, again, recognizing the tools being utilized, such as the ultrasound used to scan under the surface of the dura and the introducer which is inserted into the port and used to penetrate the brain to provide access to the tumor in a non-traumatic manner. Both tools are identified by using tracking mechanisms, as herein described. Another non-limiting context parameter that may be used to identify the stage of the surgery would be the time at which the surgery is occurring relative to the start of the surgery given this parameter was programmed into the control and processing unit 400. During the craniotomy, the control and processing unit 400 may be used to maneuver a robotic arm mounted with an imaging scope to view the cannulating introducer from an orthogonal angle so the graduation marks located on the introducer may be read, this adaptive process is above described.

Figure 24:
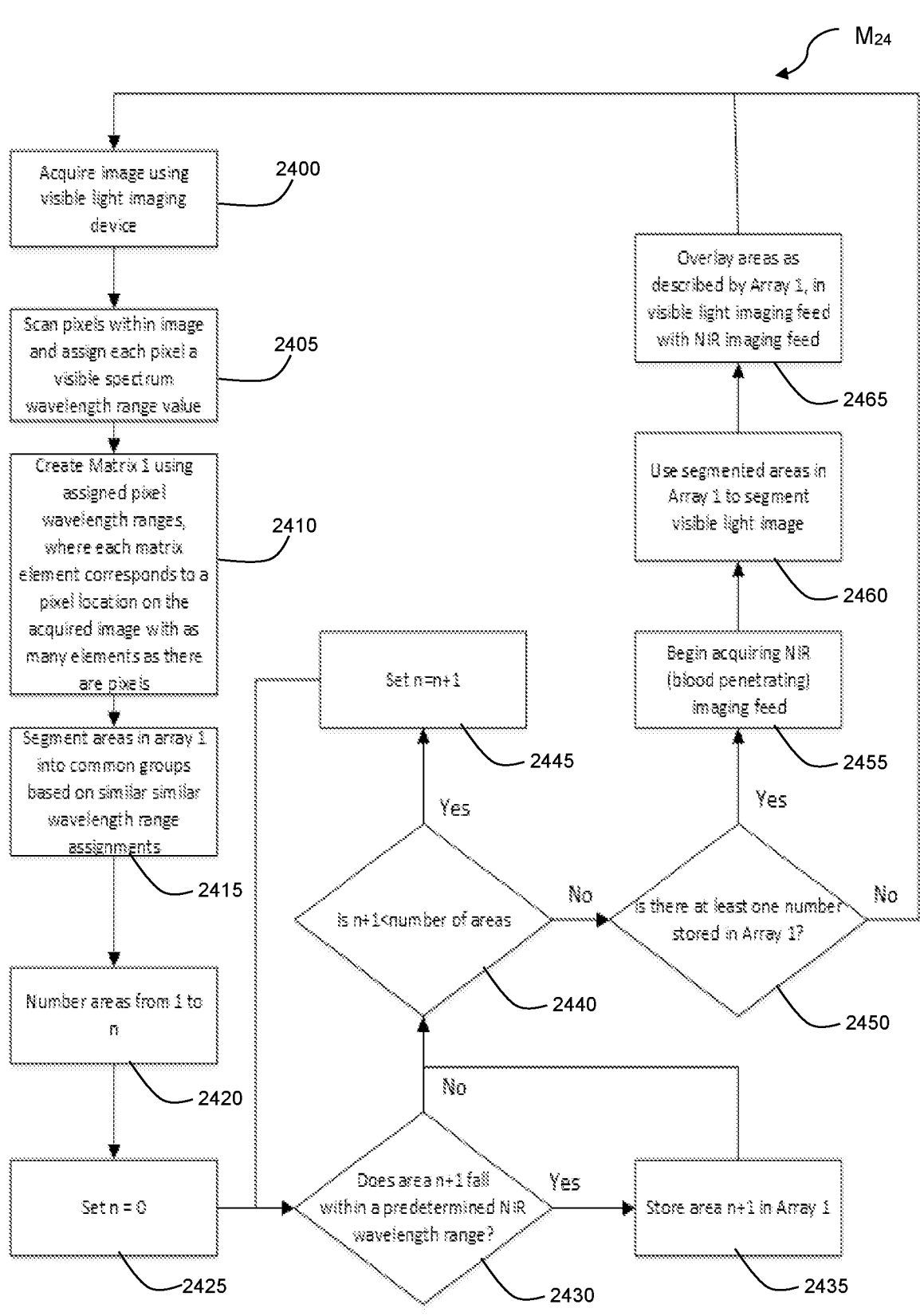
FIG. 24 is a flow chart illustrating a method relating to the analysis of images and activation of near infrared imaging.

Still referring to FIG. 21, the next stage 2120 in the procedure is gross resection (also referred to as De-bulking of Diseased Tissue) of the unhealthy tumor tissue. At this stage, the surgeon resects the mass bulk of the tumor from the patient through the access port. Again, one context parameter, used by the control and processing unit 400 to identify this stage of the surgery, relates to the removal of the introducer from the surgical field and the introduction of a resection tool. This stage 2120, as well as the next one, Precision Zone Resection 2140, referred to as fine resection, function in parallel with the Bleeding Management stages 2130, 2130. Through a periodic wavelength spectrum analysis of an imaging feed, as shown in FIG. 24 and below described in detail, acquired by using the visible imaging device mounted on the robotic arm (used to provide an enhanced view of the distal end of the port where the surgeon is performing the procedure), a bleed is identified by the control and processing unit 400.

Still referring to FIG. 21 and ahead to FIG. 23, an adaptive response to the identification of blood, occluding the view of the tissue of interest being operated on by the surgeon, comprises the overlay of NIR imaging on the occluded areas of the visible imaging (FIG. 23), as below described in detail. The context parameter that is used to identify the blood would be the blood's visible wavelength (color) spectrum. During the gross resection stage 2120, a periodic fluorescence analysis is performed on the imaging feed that is acquired by using the visible imaging device mounted on the end of a robotic arm, as above described. When a particular fluorescence spectrum that is correlated with tumor tissue is determined by the analysis, the system can adaptively configure the imaging device to begin imaging using the fluorescence camera to provide enhanced differentiation between the healthy and unhealthy brain tissue. In addition, the UI may simultaneously be configured to provide a view of the fluorescence image beside or overlaid on top of the visible light imaging.

Figure 23:
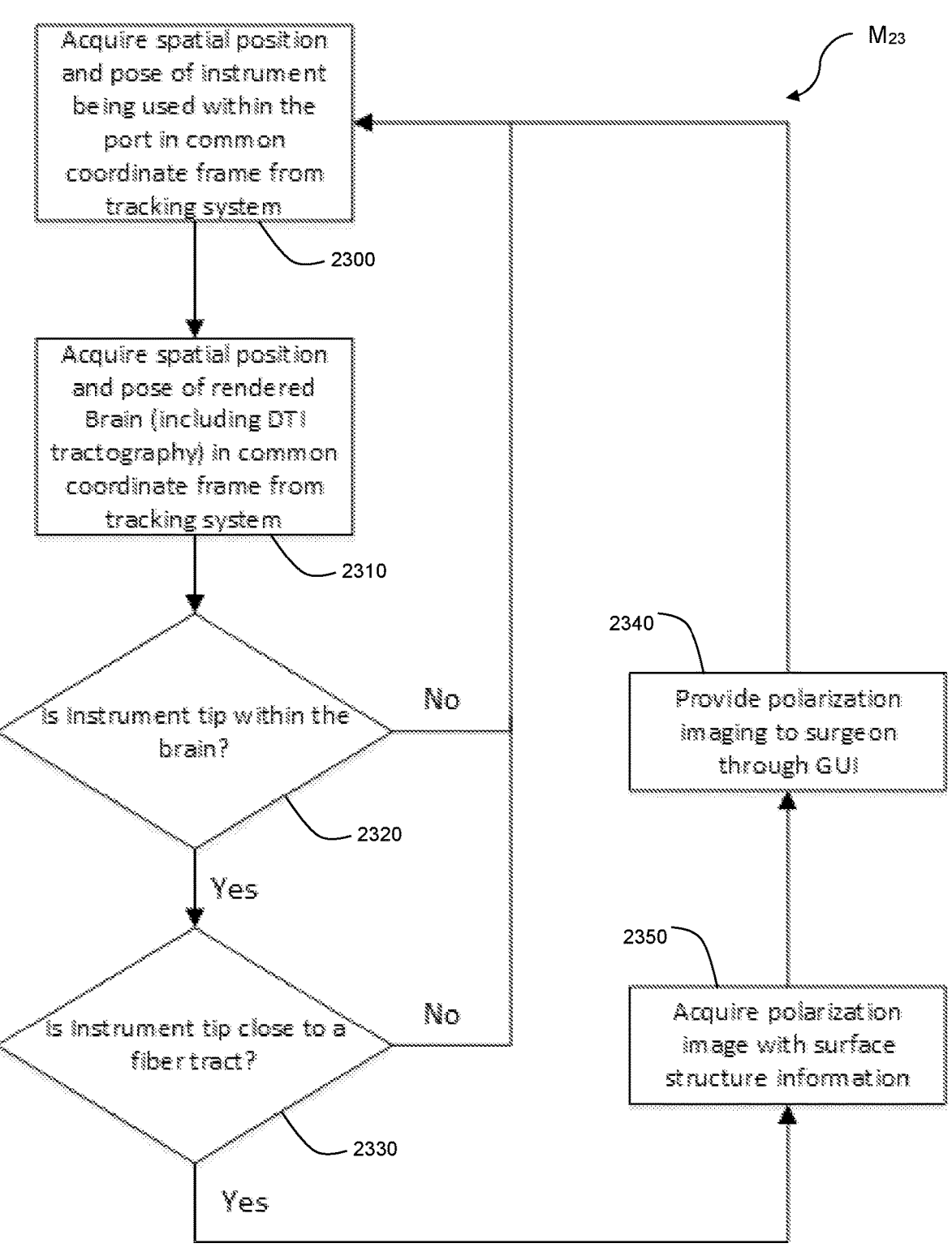
FIG. 23 is a flow chart illustrating a method relating to the analysis of spatial data and the activation of polarization imaging.

Still referring to FIG. 21 and ahead to FIG. 23, the next stage in the procedure is fine resection 2140. In this stage, the surgeon begins resecting the tumor at the boundaries of the healthy tissue. A context parameter, which is potentially used to determine this stage of the procedure, comprises the zoom of the visible imaging device, given that the surgeon indicates that some zoom above a particular threshold is required. Another context parameter could be when the location of the tool is close to the edge of the tumor on the rendered MRI scan of the patient. Given that the system knows the location of the tool relative to the patient's brain as a result of the registration of the 3D rendered MRI scan, when the system detects the tool is near a nerve tract, the system can adaptively configure the imaging device to begin acquiring polarization sensitive imaging (FIG. 23) as below described in detail.

Still referring to FIG. 21, this imaging provides more structural information than simply visible light imaging, as structure is inferred from the polarized light, the method of which is described in Wood, M. et al., Polarization Bire-fringence measurements for characterizing the myocardium, including healthy, infarcted, and stem-cell regenerated tissues, J. Biomed. Opt. 15 (4), 2010. The context measure in the aforementioned example mentioned would be the location of the tracked instrument (in this case a resection device) with respect to the registered patient brain and rendered MRI scan with DTI data. During the Therapeutic delivery stage 2160 of the procedure, therapeutic drugs are delivered to the region of interest where the tumor is located. A context measure that can be used to determine this stage of the procedure could, again, be the use of a medical instrument, and, in particular, a device used to deliver a therapeutic, such as a solution, to the site of interest. Given the medical instrument being used to deliver the therapeutic, the device, or potentially an additional instrument also being used at the surgical site of interest, is mounted with a point source imaging probe able to provide a spectral analysis of a particular point at which the point source imaging probe is aimed, the adaptive system utilizes the spectrum acquired, such as for an array of points to map onto those points, e.g., on the imaging feed, the particular spectra, or an analysis of the particular spectra, thereby assisting the surgeon in identifying where the therapeutic solution needs to be delivered. In addition, the system further identifies, to the surgeon, what particular solution could be utilized to most effectively provide therapy to those points if used in combination with a database system, for example, the one described in PCT Patent Application No. PCT/CA2014/050269, titled "INTRAMODAL SYNCHRONIZATION OF SURGICAL DATA" and filed on Mar. 14, 2014, which is incorporated herein by reference in its entirety. The final stage in the process 2170 is the closure verification of the craniotomy after the invasive portion of the procedure has been completed.

Still referring to FIG. 21 and FIG. 11B, in the preceding example embodiment, the current phase of a medical procedure is identified based on at least one of an intraoperative input by the user(s) and image analysis; and this context measure is employed to determine customized configuration parameters for intraoperatively configuring one or more devices. The above described example implementation employs spectra image analysis of the surgical field (or of a region of interest within the surgical field) to extract a representative average spectral response which may be compared with reference spectra associated with different phases of the medical procedure. In another example implementation, image analysis may be performed to identify one or more medical instruments that are being employed during a medical procedure, as described in detail above. However, rather than associating the identity of a given medical instrument directly with one or more configuration parameters, the identity of a medical instrument may be associated with a given phase of the medical procedure in which the medical instrument is commonly employed. Accordingly, the intraoperative identification of one or more medical instruments, based on image analysis, may be employed to provide a context measure identifying the current phase of a medical procedure, and configuration data, such as the example data provided in FIG. 11B, may be provided for the determination of one or more configuration parameters associated with the identified phase of the medical procedure.

Still referring to FIG. 21, in some embodiments, as described above, optical imaging may be performed to determine one or more context measures associated with the present state of the medical procedure. For example, optical imaging may be employed using one or more spectral regions including ultraviolet, visible, and infrared. In another example implementation, fluorescence imaging may be employed. Other examples of optical imaging modalities include polarization sensitive imaging, hyperspectral imaging, optical coherence imaging, and polarization-sensitive optical coherence imaging, and Raman imaging. Although the preceding examples describe methods in which one or more context parameters are obtained based on intraoperative optical imaging, intraoperative imaging may be performed using any imaging modality, including, but not limited to, intraoperative magnetic resonance imaging, intraoperative ultrasound imaging, intraoperative photoacoustic imaging, intraoperative CT, and intraoperative PET.

Figure 22:
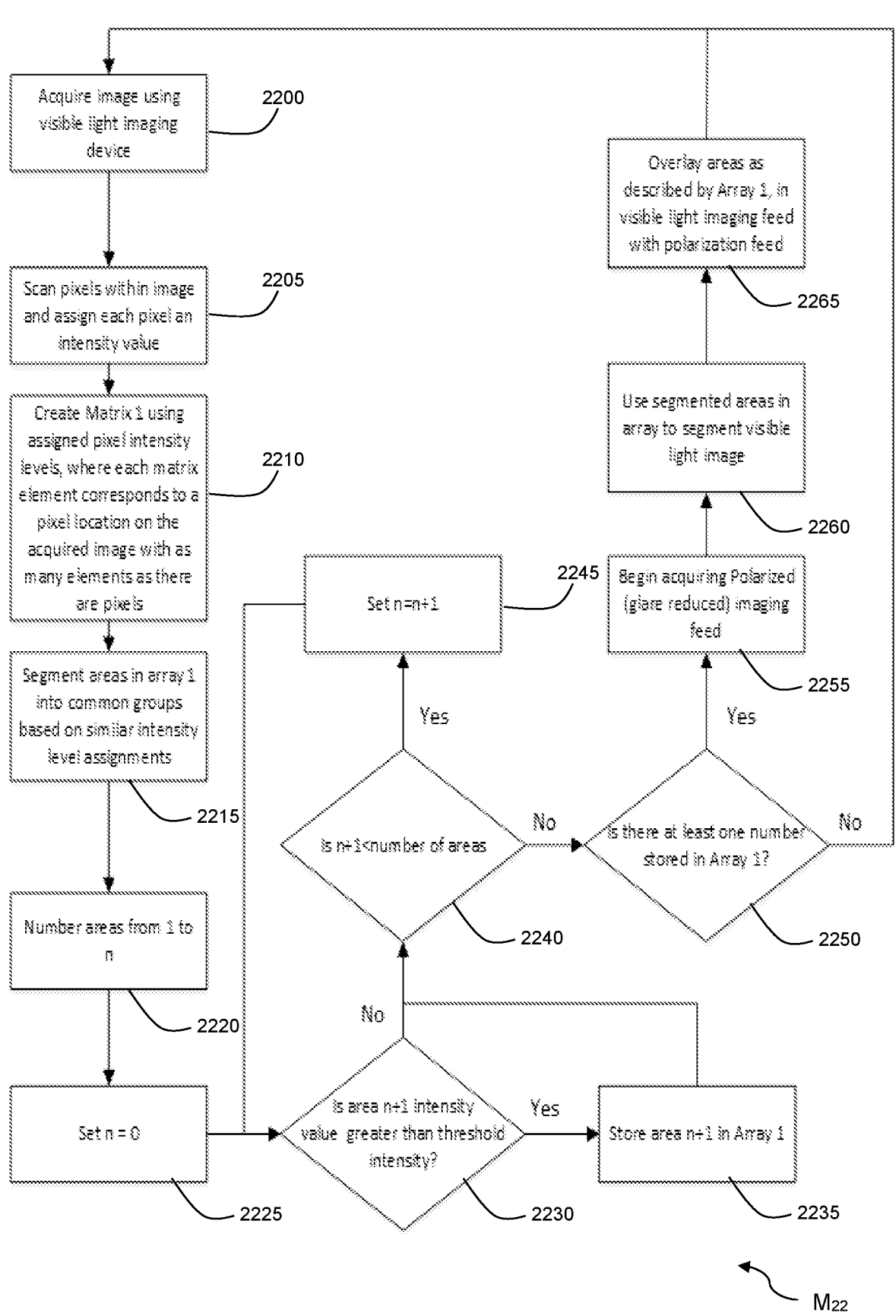
FIG. 22 is a flow chart illustrating a method relating to the analysis of images and activation of polarization imaging.

Referring to FIG. 22, this flow chart illustrates a method $M_{22}$ relating to the analysis of images and activation of polarization imaging, in accordance with an embodiment of the present disclosure. In one embodiment, the adaptive system is utilized to configure the imaging device (video scope) to reduce glare conditions at the surgical site of interest. The first step 2200 in this process is to acquire a visible light image from the imaging device (for example an external scope). The following step 2205 in the process is to scan the signal from each pixel within the region of interest on the acquired image, assigning each pixel an intensity value based on the dynamic range of the imaging device (in a port based surgery this would be the distal end of the port, where the surgical site is located and tumor resection is being performed by the surgeon). Using these values, the third stage in the process 2210 is to create a matrix using these pixels, where each element of the matrix corresponds to a pixel location on the image and the corresponding matrix element locations are conserved with respect to their pixel counterparts.

Still referring to FIG. 22, the next step 2215 in the process is identifying areas, defined by >x number of pixels in a row in the X direction and >y number of pixels in a row in the Y direction (X and Y being chosen values for a minimum area), of groups of pixels with similar intensities. Step 2220 comprises assigning each area a value from 1 to n, continuing with the flow chart. In step 2225, n=zero, so that in the following step 2230, the n=1 case is considered (since step 2230 involves assessing area number n+1). The following steps 2230, 2235, 2240, 2245 pertain to a loop that determines if each identified area (1 to n) intensity level is indicative of glare conditions. The glare condition can be chosen by a user and input into the adaptive system or predetermined by the adaptive system and is defined by an intensity threshold. The loop stores each area that is indicative of glare conditions, e.g., has an intensity above the given threshold, in an array.

Still referring to FIG. 22, the next step before continuing 2250 is checking whether any areas with glare conditions exist and, if not, the process returns to the first step 2200 and is repeated. If glare conditions exist, the next step 2255 indicates that polarized imaging should begin getting acquired by the imaging device (for example the external scope). In the next step 2260, the imaging stream acquired from the visible light imaging device is segmented according to the areas as defined by the array and located on the matrix. The final step 2265 comprises overlaying those identified areas by using the polarization imaging stream, acquired using the imaging device. This overlay effectively reduces the glare conditions for the surgeon as they perform the surgery.

Referring to FIG. 23, this flow chart illustrates a method M$_{23}$ relating to the analysis of spatial data and the activation of polarization imaging, in accordance with an embodiment of the present disclosure. The actuation of an example method of utilizing polarization sensitive imaging to determine surface structures is shown. One particular use of this type of imaging for deciphering surface structures that are representative of vital regions within a patient's brain, such as fiber tracts or surface structures within the patient's body such as tendons. The first step 2300 in this process is acquiring the spatial position of the instrument (such as a resection device) in the spatially registered intraoperative reference frame associated with the navigation system, e.g., using the tracking device within used by the navigation system. The second step 2310 is spatially registering the position of the preoperative 3D MRI image data in the common coordinate frame from the navigation system.

Still referring to FIG. 23, the following two steps 2320 and 2330 are used to determine whether the instrument comes close to a fiber tract, such as whether the instrument approaches a fiber tract in close proximity, e.g., within a pre-selected distance. If the instrument is not deemed close to a fiber tract, the process returns to the initial step 2300 and repeats. If the instrument is determined to be close to a fiber tract, the system control and processing unit 400 configures the imaging device to begin acquiring polarization sensitive imaging 2350 and displays the imaging to the surgeon 2340. This allows the surgeon to potentially decipher any brain tracts that may be damaged while performing resection and allows the surgeon to stay clear of those vital areas. The specific embodiments, above described, have been shown by way of example; and these embodiments may be susceptible to various modifications and alternative forms. The claims are not intended to be limited to the particular forms disclosed, but rather to cover all modifications, equivalents, and alternatives falling within the spirit and scope of the present disclosure.

Referring to FIG. 24, this flow chart illustrates a method M$_{24}$ relating to the analysis of images and activation of near infrared imaging, in accordance with an embodiment of the present disclosure. In an embodiment, a method of adaptively controlling a system is utilized to configure the imaging device (video scope) to reduce glare conditions. Unlike the intensity-based example, as shown in FIG. 22, the present example method employs spectral analysis for the detection of conditions, associated with blood occlusion, in the surgical site of interest. The first step 2400 in this process is acquiring a visible light image from the imaging device (for example an external scope). The following step 2405 in the process is scanning each pixel within the region of interest on the acquired image assigning each pixel a wavelength (color) spectrum value, based on the appropriate range of the visible light spectrum. Using these values, the third stage in the process 2410 is creating a matrix by using these pixels, wherein each element of the matrix corresponds to a pixel location on the image, and the corresponding matrix element locations are conserved with respect to their pixel counterparts. The next step 2415 in the process is identifying areas, defined by >x number of pixels in a row in the X direction and >y number of pixels in a row in the Y direction (X and Y being chosen values for a minimum area), of groups of pixels with similar wavelength spectrums. Step 2420 is assigning each area a value from 1 to n, continuing with the flow chart.

Still referring to FIG. 24, in step 2425, n is initially set to zero, so that in the following step 2230, the n=1 case is considered (since step 2430 involves assessing area number n+1). The following steps 2430, 2435, 2440, 2445 pertain to a loop that determines if each identified area (1 to n) intensity level is indicative of blood occlusion. The blood occlusion can be identified by comparing the assigned wavelength spectrum values to a known value for blood (corresponding to its color). The loop stores each area which is indicative of blood occlusion, e.g., has the same wavelength spectrum as blood, in an array. Before continuing the following step 2250 checking whether any areas with blood occlusion exist and, if not, the process returns to the first step 2400 and is repeated. If there is blood occlusion, the next step 2455 indicates that whether the image acquisition based on near-infrared (NIR) imaging should commence (for example by the imaging device acquiring NIR images with the external scope). In the next step 2460 the imaging stream acquired from the visible light imaging device is segmented according to the areas as defined by the array and located on the matrix. The final step 2465 is overlaying those identified areas using the NIR imaging stream acquired using the imaging device. This overlay effectively increases the ability of the surgeon to see through the blood as they perform the surgery.

Referring to FIG. 25, this schematic diagram illustrates a control and processing system 2500 interfaceable with at least one device, a tracking system, and a data storage device, in accordance with an embodiment of the present disclosure. The control and processing system 2500 comprising a processor 2501, configured by a set of instructions storable in relation to a nontransient memory device (not shown), to: identify the at least one device, via the tracking system operating with at least one of an electromagnetic system and a radiofrequency (RF) system, during a medical procedure; obtain at least one image of a region of interest associated with the medical procedure; process the at least one image to identify a context measure associated with a current state of the medical procedure; obtain at least one parameter for adaptively configuring the at least one device during the medical procedure, the at least one parameter customizable based on the context measure, the at least one parameter providable for the at least one device according to a prioritized list, and the at least one device reverting to a default configuration when at least one other device is removed from the region of interest; and configure the at least one device according to the at least one parameter.

Still referring to FIG. 25, in the system 2500, by example only, the context measure is associated with at least one of: a current phase of the medical procedure, a type of the medical procedure, presence of least one tissue type within the region of interest, presence of at least one fluid within the region of interest, and presence of at least one medical instrument within the region of interest. For example, the at least one fluid comprises a biological fluid, such as blood.

Still referring to FIG. 25, in the system 2500, the processor 2501 is further configured to process the at least one image by: acquiring hyperspectral image data from the region of interest; processing the hyperspectral image data to identify at least one region having a similar spectral response among a plurality of pixels; comparing an average spectral response from each at least one region, having the similar spectral response, to reference spectra associated with different phases of the medical procedure; and identifying the current phase of the medical procedure, based on similarity between an average spectral response and the reference spectra.

Still referring to FIG. 25, in the system 2500, the processor 2501 is further configured to process the at least one image to identify the current phase of the medical procedure by: processing the at least one image to identify at least one tissue type present within the region of interest; and determining the current phase of the medical procedure, based on the at least one tissue type. The processor is further configured to process the at least one image to identify the current phase of the medical procedure by: performing image analysis to identify at least one medical instrument, based on a known shape of the at least one medical instrument; and determining the current phase of the medical procedure, based on presence of the at least one medical instrument.

Still referring to FIG. 25, in the system 2500, by example only, the at least one image comprises at least one of: at least one optical image, at least one optical coherence tomography image, at least one magnetic resonance image, and at least one ultrasound image. For example, the at least one optical image is based on one of: detection in at least a visible spectrum, and detection in at least an infrared spectrum. The processor 2501 is further configured to process the at least one image by processing a plurality of images from a plurality of different imaging modalities.

Still referring to FIG. 25, in the system 2500, by example only, the at least one device comprises at least one of: a surgical tool, an auxiliary device, an illumination device, an imaging device, a robotic positioning device, and computer hardware for generating a user interface on a display. For example, the at least one device comprises at least one imaging device, the at least one parameter comprises at least of: a color balance, a brightness, a depth of field, a magnification, a field of view, a working distance, and an illumination condition, the at least one imaging device comprises at least one multimodal imaging device, and the at least one parameter comprises a selection of an imaging modality.

Referring to FIG. 26, this flow diagram illustrates a method M1 of providing a control and processing system 2500, as shown in FIG. 25, interfaceable with at least one device, a tracking system, and a data storage device, in accordance with an embodiment of the present disclosure. The method M1 comprises: providing a processor 2501, as indicated by block 2601; and configuring the processor 2501 by a set of instructions storable in relation to a nontransient memory device to: identify the at least one device, via the tracking system operating with at least one of an electromagnetic system and a radiofrequency (RF) system, during a medical procedure; obtain at least one image of a region of interest associated with the medical procedure; process the at least one image to identify a context measure associated with a current state of the medical procedure; obtain at least one parameter for adaptively configuring the at least one device during the medical procedure, the at least one parameter customizable based on the context measure, the at least one parameter providable for the at least one device according to a prioritized list, and the at least one device reverting to a default configuration when at least one other device is removed from the region of interest; and configure the at least one device according to the at least one parameter, as indicated by block 2602.

Still referring to FIG. 26, in the method M1, in configuring the processor 2501 to obtain the at least one parameter for adaptively configuring the at least one device during the medical procedure, the context measure is associated with at least one of: a current phase of the medical procedure, a type of the medical procedure, presence of least one tissue type within the region of interest, presence of at least one fluid within the region of interest, and presence of at least one medical instrument within the region of interest. In the method M1, configuring the processor 2501 to process the at least one image further comprises configuring the processor to: acquire hyperspectral image data from the region of interest; process the hyperspectral image data to identify at least one region having a similar spectral response among a plurality of pixels; compare an average spectral response from each at least one region, having the similar spectral response, to reference spectra associated with different phases of the medical procedure; and identify the current phase of the medical procedure, based on similarity between an average spectral response and the reference spectra. In the method M1, configuring the processor 2501 to process the at least one image further comprises configuring the processor to: process the at least one image to identify at least one tissue type present within the region of interest; and determine the current phase of the medical procedure, based on the at least one tissue type.

Still referring to FIG. 26, in the method M1, configuring the processor 2501 to process the at least one image further comprises configuring the processor to: perform image analysis to identify at least one medical instrument, based on a known shape of the at least one medical instrument; and determine the current phase of the medical procedure, based on presence of the at least one medical instrument. In the method M1, in configuring the processor 2501, the at least one image comprises at least one of: at least one optical image, at least one optical coherence tomography image, at least one magnetic resonance image, and at least one ultrasound image; and the at least one optical image is based on one of: detection in at least a visible spectrum, and detection in at least an infrared spectrum. In the method M1, configuring the processor 2501 further comprises configuring the processor to process the at least one image by processing a plurality of images from a plurality of different imaging modalities, wherein the at least one device comprises at least one of: a surgical tool, an auxiliary device, an illumination device, an imaging device, a robotic positioning device, and computer hardware for generating a user interface on a display, and wherein at least one of: the at least one device comprises at least one imaging device, the at least one parameter comprises at least of: a color balance, a brightness, a depth of field, a magnification, a field of view, a working distance, and an illumination condition, the at least one imaging device comprises at least one multimodal imaging device, and the at least one parameter comprises a selection of an imaging modality.

Referring to FIG. 27, this flow diagram illustrates a method M2 of adaptively configuring at least one device used during a medical procedure by way of a control and processing system 2500, as shown in FIG. 25, interfaceable with at least one device, a tracking system, and a data storage device, in accordance with an embodiment of the present disclosure. The method M2 comprising: providing the control and processing system 2500, as indicated by block 2700, by providing a processor 2501, as indicated by block 2701; and configuring the processor 2501 by a set of instructions storable in relation to a nontransient memory device to: identify the at least one device, via the tracking system operating with at least one of an electromagnetic system and a radiofrequency (RF) system, during a medical procedure; obtain at least one image of a region of interest associated with the medical procedure; process the at least one image to identify a context measure associated with a current state of the medical procedure; obtain at least one parameter for adaptively configuring the at least one device during the medical procedure, the at least one parameter customizable based on the context measure, the at least one parameter providable for the at least one device according to a prioritized list, and the at least one device reverting to a default configuration when at least one other device is removed from the region of interest; and configure the at least one device according to the at least one parameter, as indicated by block 2702; identifying the at least one device, via the tracking system operating with at least one of the electromagnetic system and the radiofrequency (RF) system, during the medical procedure, as indicated by block 2703; obtaining the at least one image of the region of interest associated with the medical procedure, as indicated by block 2704; processing the at least one image to identify the context measure associated with the current state of the medical procedure, as indicated by block 2705; obtaining the at least one parameter for adaptively configuring the at least one device during the medical procedure, the at least one parameter customizable based on the context measure, the at least one parameter providable for the at least one device according to a prioritized list, and the at least one device reverting to a default configuration when at least one other device is removed from the region of interest, as indicated by block 2706; and configuring the at least one device according to the at least one parameter, as indicated by block 2707.

What is claimed:

1. A control and processing system interfaceable with at least one device, a tracking system, and a data storage device, the control and processing system comprising;

a processor configured by a set of instructions storable in relation to a nontransient memory device to:

identify the at least one device, via the tracking system operating with at least one of an electromagnetic system and a radiofrequency (RF) system, during a medical procedure;

obtain at least one image of a region of interest containing blood associated with the medical procedure;

process the at least one image to identify a context measure associated with a current state of the medical procedure;

obtain at least one parameter for adaptively configuring the at least one device during the medical procedure, the at least one parameter customizable based on the context measure, the at least one parameter providable for the at least one device according to a prioritized list, and the at least one device reverting to a default configuration when at least one other device is removed from the region of interest; and wherein the processor is further configured to process the at least one image by: acquiring hyperspectral image data from the region of interest;

processing the hyperspectral image data to identify at least one region having a similar spectral response among a plurality of pixels; comparing an average spectral response from each at least one region, having the similar spectral response, to reference spectra associated with different phases of the medical procedure; and identifying the current phase of the medical procedure, based on similarity between an average spectral response and the reference spectra;

wherein the at least one optical image is based on one of: detection in at least a visible spectrum, and detection in at least an infrared spectrum; and configure the at least one device according to the at least one parameter.

2. The system of claim 1, wherein the context measure is associated with at least one of: a current phase of the medical procedure, a type of the medical procedure, presence of least one tissue type within the region of interest, presence of at least one fluid within the region of interest, and presence of at least one medical instrument within the region of interest.

3. The system of claim 2, wherein the at least one fluid comprises a biological fluid.

4. The system of claim 3, wherein the biological fluid comprises blood.

5. The system of claim 1, wherein the processor is further configured to process the at least one image to identify the current phase of the medical procedure by: processing the at least one image to identify at least one tissue type present within the region of interest; and determining the current phase of the medical procedure, based on the at least one tissue type.

6. The system of claim 1, wherein the processor is further configured to process the at least one image to identify the current phase of the medical procedure by: performing image analysis to identify at least one medical instrument, based on a known shape of the at least one medical instrument; and determining the current phase of the medical procedure, based on presence of the at least one medical instrument.

7. The system of claim 1, wherein the at least one image comprises at least one of: at least one optical image, at least one optical coherence tomography image, at least one magnetic resonance image, and at least one ultrasound image.

8. The system of claim 1, wherein the processor is further configured to process the at least one image by processing a plurality of images from a plurality of different imaging modalities.

9. The system of claim 1, wherein the at least one device comprises at least one of: a surgical tool, an auxiliary device, an illumination device, an imaging device, a robotic positioning device, and computer hardware for generating a user interface on a display.

10. The system of claim 1, wherein at least one of: the at least one device comprises at least one imaging device, the at least one parameter comprises at least of: a color balance, a brightness, a depth of field, a magnification, a field of view, a working distance, and an illumination condition, the at least one imaging device comprises at least one multimodal imaging device, and the at least one parameter comprises a selection of an imaging modality.

* * * * *